United States Patent
Dobosy et al.

(10) Patent No.: US 10,982,273 B2
(45) Date of Patent: Apr. 20, 2021

(54) RNASE H MUTANTS IN AN EMULSION

(71) Applicant: Integrated DNA Technologies, Inc., Skokie, IL (US)

(72) Inventors: Joseph Dobosy, Coralville, IA (US); Sarah Jacobi, North Liberty, IA (US); Richard Owczarzy, Coralville, IA (US); Mark Behlke, Coralville, IA (US); Jessica Lister, Coralville, IA (US)

(73) Assignee: Integrated DNA Technologies, Inc., Skokie, IL (US)

( * ) Notice: Subject to any disclaimer, the term of this patent is extended or adjusted under 35 U.S.C. 154(b) by 442 days.

(21) Appl. No.: 15/672,685

(22) Filed: Aug. 9, 2017

(65) Prior Publication Data

US 2018/0044716 A1    Feb. 15, 2018

Related U.S. Application Data

(60) Provisional application No. 62/372,436, filed on Aug. 9, 2016.

(51) Int. Cl.
| | |
|---|---|
| *C12Q 1/686* | (2018.01) |
| *C12N 9/22* | (2006.01) |
| *C12Q 1/6853* | (2018.01) |
| *C12Q 1/6858* | (2018.01) |
| *C12Q 1/6862* | (2018.01) |
| *C12N 15/52* | (2006.01) |

(52) U.S. Cl.
CPC ............. *C12Q 1/686* (2013.01); *C12N 9/22* (2013.01); *C12Q 1/6853* (2013.01); *C12Q 1/6858* (2013.01); *C12Q 1/6862* (2013.01); *C12Y 301/26004* (2013.01); *C12N 15/52* (2013.01)

(58) Field of Classification Search
None
See application file for complete search history.

(56) References Cited

U.S. PATENT DOCUMENTS

| | | |
|---|---|---|
| 5,403,711 A | 4/1995 | Walder et al. |
| 6,440,706 B1 | 8/2002 | Vogelstein et al. |
| 7,514,210 B2 | 4/2009 | Holliger et al. |
| 8,911,948 B2 | 12/2014 | Walder et al. |
| 2007/0020653 A1 | 1/2007 | Holliger et al. |
| 2012/0088246 A1 | 4/2012 | Opdyke et al. |
| 2013/0310269 A1 | 11/2013 | So |
| 2014/0162249 A9 | 6/2014 | Behlke et al. |

FOREIGN PATENT DOCUMENTS

| | | |
|---|---|---|
| JP | 2008-054599 A | 3/2008 |
| WO | 2013/142364 A1 | 9/2013 |
| WO | 2018/031625 A2 | 2/2018 |

OTHER PUBLICATIONS

Ausubel et al., "Introduction to Gene Editing and Manipulation Using CRISPR/CAS9 Technology," Current Protocols in Molecular Biology, 2016, 115:31.4.1-31.4.6.
Dobosy et al., "RNase H-dependent PCR (rhPCR): improved specificity and single nucleotide polymorphism detection using blocked cleavable primers," BMC Biotechnology 2011, 11:80.
Duck et al., "Probe amplifier system based on chimeric cycling oligonucleotides," BioTechniques, 1990, 9(2):142-148.
Hindson et al., "High-Throughput Droplet Digital PCR System for Absolute Quantitation of DNA Copy Number," Analytical Chemistry, 2011, 83(22):8604-8610.
Jones et al., "Low copy target detection by Droplet Digital PCR through application of a novel open access bioinformatic pipeline, 'definetherain'," Journal of Virological Methods, 2014, 202:46-53.
Manoj, P., "Droplet digital PCR technology promises new applications and research areas," Mitochondrial DNA, 2016, 27(1):742-746.
Pinheiro et al., "Evaluation of a Droplet Digital Polymerase Chain Reaction Format for DNA Copy Number Quantification," Analytical Chemistry, 2012, 84(2):1003-1011.
Rychlik et al., "Crystal Structures of RNase H2 in Complex with Nucleic Acid Reveal the Mechanism of RNA-DNA Junction Recognition and Cleavage," Molecular Cell 40, 2010, 658-670.
Sambrook et al., Molecular Cloning: A Laboratory Manual, 4th ed., Cold Spring Harbor Press, Cold Spring Harbor, New York (2012).
Tomita et al., "Loop-mediated isothermal amplification (LAMP) of gene sequences and simple visual detection of products," Nature Protocols, 2008, 3(5):877-882.
Vogelstein et al., "Digital PCR," Proceedings of the National Academy of Sciences USA, 1999, 96(16):9236-9241.
Warnon et al., "Colorimetric Detection of the Tuberculosis Complex Using Cycling Probe Technology and Hybridization in Microplates," BioTechniques, 2000, 28(6):1152-1160.
Weiner M. et al., "Site-directed mutagenesis of double-stranded DNA by the polymerase chain reaction," Gene, 1994, 151(1-2):119-123.
International Search Report and Written Opinion for Application No. PCT/US2017/046048 dated Feb. 28, 2018 (12 pages).
European Patent Office Extended Search Report for Application No. 17840187.3 dated Sep. 8, 2020 (10 pages).

*Primary Examiner* — Kagnew H Gebreyesus
(74) *Attorney, Agent, or Firm* — Michael Best & Friedrich LLP

(57) ABSTRACT

The invention is directed to methods and kits for performing an RNase H2-mediated cleavage reaction on a sample in an emulsion.

13 Claims, 12 Drawing Sheets

Specification includes a Sequence Listing.

Figure 5

```
                           S                                                R
P.fur     MKIGGIDEAGRGPAIGPLVVAYVVDEKNIEKLRNIGVKDSKQLTPHERKNLFSQITSIA    60
P.abyssi  MKVAGADEAGRGPVIGPLVIVAAVVEEDKIRSLTKLGVKDSKQLTPAQREKLFDEIYKVL    60
P.hori    MKVAGVDEAGRGPVIGPLVIGVAVIDEKNIERLRDIGVKDSKQLTPGQREKLFSKLIDIL    60
T.kod     MKIAGIDEAGRGPVIGPMVIAAVVVDENSLPKLEELKVRDSKKLTPKRREKLFNEILGVL    60
T.lit     MKLGGIDEAGRGPVIGPLVIAAVVVDESRMQELEALGVKNSRKLTPKRREELFEEIVQIV    60

L                         V
P.fur     DDYKIVIVSPEEIDNRSGTMNELEVEKFALALNSLQIKPALIYADAADVDANRFASLIER   120
P.abyssi  DDYSVVIVSPQDIDGRKGSMNELEVENFVKALNSLKVRPEVIYIDSADVKAERFAENIRS   120
P.hori    DDYVLLVTPKEIDERHHSMNELEAEKFVVALNSLRIKPQKIYVDSADVDPKRFASLIKA    120
T.kod     DDYVILELPPDVIGSREGTLNEFEVENFAKALNSLEVKPDVIYADAADVDEERFAREGE    120
T.lit     DDHVIIQLSPEEIDGRDGTMNELEIENFAKALNSLEVKPDVLYIDAADVKEKRFGDIIGE   120

P.fur     RLNYKAKIIAEHKADAKYPVVSAASILAKVVRDEEIEKLKKQYGDFGSGYPSDPKTKKWL   180
P.abyssi  RLAYEAKVVAEHKADAKYEIVSAASILAKVIRDREIEKLKAEYGDFGSGYPSDPRTKKWL   180
P.hori    GLKYEATVIAEHKADAKYEIVSAASIIAKVTRDREIEKLKQKYGEFGSGYPSDPRTKEWL   180
T.kod     RLNFEAEVVAKHKADDIFPVVSAASILAKVTRDPAVEKLKEEYGEIGSGYPSDPRTRAFL   180
T.lit     RLSFSPKIIAEHKADSKYIPVAAASILAKVTRDRAIEKLKELYGEIGSGYPSDPNTRRFL   180

P.fur     EEYYKRHNSFPPIVRRTWETVRKIEESIKAKKSQ----LTLDKFFKKP--   224   SEQ ID NO: 95
P.abyssi  EEWYSKHGNFPPIVRRTWDTAKKIEEKF--KRAQ----LTLDNFLKRFRN   224   SEQ ID NO: 125
P.hori    EEYYKQYGDFPPIVRRTWETARKIEERF--RKNQ----LTLDKFLK----   220   SEQ ID NO: 96
T.kod     ENYYREHGEFPPIVRKGWKTLKKIAEKVESEKKAEERQATLDRYFRKV--   228   SEQ ID NO: 97
T.lit     EEYYKAHGEFPPIVRKSWKTLRKIEEKLKAKKTQ----PTILDFLKKP--   224   SEQ ID NO: 98
```

RNASE H MUTANTS IN AN EMULSION

CROSS-REFERENCE TO RELATED APPLICATIONS

This patent application claims the benefit of U.S. Provisional Patent Application No. 62/372,436, filed Aug. 9, 2016.

BRIEF DESCRIPTION OF THE INVENTION

This invention relates to the use of mutant RNase H2 enzymes in an emulsion system.

REFERENCE TO SEQUENCE LISTING

This application is filed with a Computer Readable Form of a Sequence Listing in accordance with 37 C.F.R. § 1.821(c). The text file submitted by EFS, "013670-9038-US01_sequence_listing_updated_10-NOV-2020_ST25.txt," was created on Nov. 10, 2020, contains 165 sequences, has a file size of 147 Kbytes (151,511 bytes), and is hereby incorporated by reference in its entirety.

BACKGROUND OF THE INVENTION

Polymerase chain reaction (PCR) is a widely used biotechnology that allows researchers to amplify a single copy of DNA to generate large quantities of a desired product. Like many technologies, the PCR methodologies are continuously being modified to improve their efficacy. One of the challenges of PCR is the formation of "primer dimers," wherein the primers in the reaction unintentionally hybridize to each other along complementary bases. Primers that have dimerized are unable to hybridize to the target sequence on DNA, preventing amplification. Carefully designing primers reduces the likelihood of primer dimer formation; however, it is occasionally necessary to position primers at suboptimal locations in a target DNA sequence.

RNase H-dependent PCR (rhPCR) was developed in part to reduce primer dimer formation in PCR. In an rhPCR system, the primers are "blocked" with the inclusion of non-extendable groups at the 3'-end of the primer, such as a label or a C3 spacer. The primers include one or more ribonucleotide residues near the 3'-end of the primer, and an RNase H is used to cleave the primer at the RNA base region if there is perfect complementary between the primer and target. The cleaving of the primer with RNase H removes the blocking group and allows extension with a DNA polymerase. RhPCR therefore enhances the specificity of the priming/extension and reduces unwanted extension products such as the products that may result from primer-dimers.

Walder et al., described the use of an RNase H2 enzyme derived from the hyperthermophilic archaeon *Pyrococcus abyssi* (P.a.) (see, e.g., International Patent Application Publication WO 2013/142364). RNase H enzymes are endoribonucleases that cleave the phosphodiester bond in an RNA strand when it is part of an RNA:DNA duplex. P.a. RNase H2 is active at high temperatures with reduced activity at lower temperatures, allowing the PCR reaction to be setup at room temperature without premature cleaving of the ribonucleotide. RNase H2 is compatible with most PCR buffers, and when added directly to the PCR master mix, cleavage of the ribonucleotide residue occurs seamlessly with PCR amplification by the DNA polymerase (see, e.g., U.S. Pat. No. 8,911,948).

Improving the sensitivity and accurate quantification of amplified targets are additional areas of development in PCR technology. In particular, the combination of digital PCR and emulsion-based technologies has yielded a highly sensitive and quantitative PCR platform. In digital PCR (also known as "single molecule PCR" or "limiting dilution PCR"), a sample is sufficiently diluted and partitioned such that each partition contains on average a single copy or less of the target nucleic acid; the amplified target can additionally be quantified by including a probe in the reaction (see, e.g., Vogelstein et al., *Proc. Natl. Acad. Sci.* USA, 96: 9236-9241 (1999) and U.S. Pat. No. 6,440,706). In emulsion PCR, partitions are generated by creating a water-in-oil emulsion, wherein each droplet of water contains on average a single copy or less of a nucleic acid and the necessary reagents for performing PCR. Reaction volumes can be significantly reduced as compared to conventional 96-, 384-, or even 1536-well reactions. Emulsion PCR also permits high-throughput analysis of amplification products.

The combination of digital and emulsion based PCR platforms has yielded digital droplet PCR, which allows a nucleic acid sample to be partitioned into tens of thousands of droplets in an emulsion, with PCR amplification and quantification of the desired target occurring in each individual droplet. Digital droplet PCR provides sensitive and specific detection of single template molecules. As with all types of PCR, however, digital droplet PCR is also susceptible to primer dimer formation (see Hindson et al., *Anal Chem*, 83:8604-8610 (2011)).

The potential utility of rhPCR in a droplet digital format is extensive (see, e.g., U.S. Patent Application Publication 2013/0310269). There is a need, however for digital rhPCR methods with reduced side reactions and increased specificity. The present invention provides such methods.

BRIEF SUMMARY OF THE INVENTION

The present disclosure provides a method of performing an RNase H2-mediated cleavage of one or more nucleic acid sequences of interest, which comprises providing a sample comprising one or more nucleic acid sequences of interest; performing an RNase H2-mediated cleavage reaction on the one or more nucleic acid sequences, wherein the RNase H2-mediated cleavage reaction comprises: (i) a mutant *Pyrococcus abyssi* (P.a.) RNase H2 enzyme comprising an amino acid sequence selected from SEQ ID NO: 1, SEQ ID NO: 2, SEQ ID NO:7, SEQ ID NO:8, SEQ ID NO:13, SEQ ID NO:15, SEQ ID NO: 16, SEQ ID NO:17, SEQ ID NO:18, SEQ ID NO:20, SEQ ID NO: 70, SEQ ID NO: 71, SEQ ID NO: 73, SEQ ID NO: 74, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 90, and SEQ ID NO: 165; (ii) a mutant *Pyrococcus furiosis* (P. fur) RNase H2 enzyme comprising an amino acid sequence selected from SEQ ID NO: 126, SEQ ID NO: 127, SEQ ID NO: 128, SEQ ID NO: 129, and SEQ ID NO: 130; (iii) a mutant *Pyrococcus horikoshii* (P. hori) RNase H2 enzyme comprising an amino acid sequence selected from SEQ ID NO: 131, SEQ ID NO: 132, and SEQ ID NO: 133; (iv) a mutant *Thermococcus kodakarensis* (T. kod) RNase H2 enzyme comprising an amino acid sequence selected from SEQ ID NO: 134, SEQ ID NO: 135, and SEQ ID NO:136; or (v) a mutant *Thermococcus litoralis* (T. lit) RNase H2 enzyme comprising the amino acid sequence of SEQ ID NO: 137 or SEQ ID NO: 138; whereupon one or more nucleic acid sequences of interest are cleaved.

The present disclosure also provides a kit for cleaving one or more nucleic acid sequences of interest comprising (a) one or more reagents for performing an RNase H2-mediated cleavage reaction in an emulsion on a sample comprising one or more nucleic acid sequences of interest, (b) one or more mutant RNase H2 enzymes selected from: (i) a mutant *Pyrococcus abyssi* (P.a.) RNase H2 enzyme comprising an amino acid sequence selected from SEQ ID NO: 1, SEQ ID NO: 2, SEQ ID NO:7, SEQ ID NO:8, SEQ ID NO:13, SEQ ID NO:15, SEQ ID NO: 16, SEQ ID NO:17, SEQ ID NO:18, SEQ ID NO:20, SEQ ID NO: 70, SEQ ID NO: 71, SEQ ID NO: 73, SEQ ID NO: 74, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 90, and SEQ ID NO: 165); (ii) a mutant *Pyrococcus furiosis* (P. fur) RNase H2 enzyme comprising an amino acid sequence selected from SEQ ID NO: 126, SEQ ID NO: 127, SEQ ID NO: 128, SEQ ID NO: 129, and SEQ ID NO: 130; (iii) a mutant *Pyrococcus horikoshii* (P. hori) RNase H2 enzyme comprising an amino acid sequence selected from SEQ ID NO: 131, SEQ ID NO: 132, and SEQ ID NO: 133; (iv) a mutant *Thermococcus kodakarensis* (T. kod) RNase H2 enzyme comprising an amino acid sequence selected from SEQ ID NO: 134, SEQ ID NO: 135, and SEQ ID NO:136; and (v) a mutant *Thermococcus litoralis* (T. lit) RNase H2 enzyme comprising the amino acid sequence of SEQ ID NO: 137 or SEQ ID NO: 138, and (c) instructions for performing the RNase H2-mediated cleavage reaction.

The disclosure also provides a mutant RNase H2 enzyme selected from: (a) a mutant *Pyrococcus abyssi* (P.a.) RNase H2 enzyme comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO:7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22, SEQ ID NO: 70, SEQ ID NO: 71, SEQ ID NO: 73, SEQ ID NO: 74, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 90, or SEQ ID NO: 165); (b) a mutant *Pyrococcus furiosis* (P. fur) RNase H2 enzyme comprising the amino acid sequence of SEQ ID NO: 126, SEQ ID NO: 127, SEQ ID NO: 128, SEQ ID NO: 129, or SEQ ID NO: 130; (c) a mutant *Pyrococcus horikoshii* (P. hori) RNase H2 enzyme comprising the amino acid sequence of SEQ ID NO: 131, SEQ ID NO: 132, or SEQ ID NO: 133; (d) a mutant *Thermococcus kodakarensis* (T. kod) RNase H2 enzyme comprising the amino acid sequence of SEQ ID NO: 134, SEQ ID NO: 135, or SEQ ID NO:136; and (e) a mutant *Thermococcus litoralis* (T. lit) RNase H2 enzyme comprising the amino acid sequence of SEQ ID NO: 137 or SEQ ID NO: 138.

The present disclosure also provides mutant RNase H2 enzymes comprising one of the following: (a) an amino acid sequence comprising SEQ ID NO: 95 except for one or more of the following amino acid substitutions: A9S, R11K, P13S, E48R, M80L, A107V, P171G, S172I, D173E, E199Y, E199G, and/or F220L; (b) an amino acid sequence comprising SEQ ID NO: 96 except for one or more of the following amino acid substitutions: A9S, R11K, P13S, Q48R, M80L, A107V, P171G, S172I, D173E, E199Y, E199G, and/or F218L; (c) an amino acid sequence comprising SEQ ID NO: 97 except for one or more of the following amino acid substitutions: A9S, R11K, P13S, A107V, P171G, S172I, D173E, K199Y, K199G, K199E, and/or Y224L; or (d) an amino acid sequence comprising SEQ ID NO: 98 except for one or more of the following amino acid substitutions: A9S, R11K, P13S, M80L, A107V, P171G, S172I, D173E, K199Y, K199G, K199E, and/or F220L. The present disclosure also provides a kit for cleaving one or more nucleic acid sequences of interest comprising (a) one or more reagents for performing an RNase H2-mediated cleavage reaction in an emulsion on a sample comprising one or more nucleic acid sequences of interest, (b) one or more of the aforementioned mutant RNase H2 enzymes, and (c) instructions for performing the RNase H-mediated cleavage reaction.

The disclosure also provides a method of performing an RNase H2-mediated cleavage of one or more nucleic acid sequences of interest comprising (a) providing a sample comprising one or more nucleic acid sequences of interest and (b) performing an RNase H2-mediated cleavage reaction on the one or more nucleic acid sequences, wherein the RNase H2-mediated cleavage reaction comprises a *Thermococcus kodakarensis* (T. kod) RNase H2 enzyme comprising the amino acid sequence of SEQ ID NO: 97, whereupon one or more nucleic acid sequences of interest are cleaved.

BRIEF DESCRIPTION OF THE DRAWINGS

FIG. 5 is an alignment of the wild-type RNase H2 amino acid sequences from *P. furiosis, P. abyssi, P. horikoshii, T. kodakarensis,* and *T. literalis*. Mutations of interest that were identified in P.a. are listed above the sequences. Natural occurrences of these mutations In *T. kodakarensis* and *T. literalis* are indicated in bold and underline

*literalis*, and *P. furiosis*. An RNase P assay was run using either standard unblocked primers (U) or blocked (B) rhPrimers with 420 fmol (equivalent of 200 mU wild-type P.a.) of the indicated wild-type RNase H2.

Figure 7:
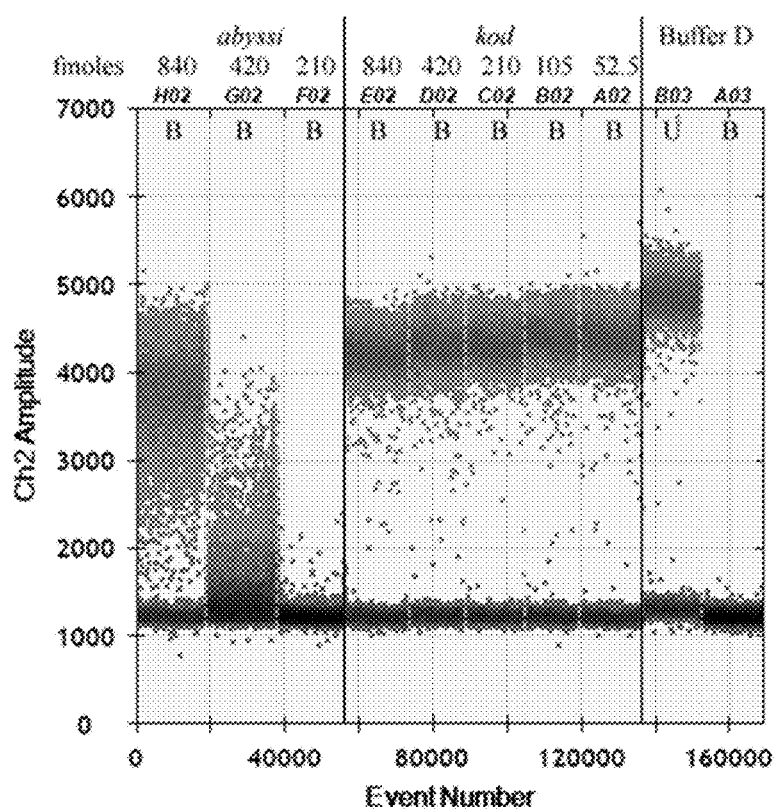

FIG. 7 is a plot from a QX-200™ DROPLET DIGITAL™ (DDPCR™) system (Bio-Rad Laboratories, Inc., Hercules, Calif.) showing a comparison of P.a. and T. kod wild-type RNase H2 titrations. An RNase P assay was run using either standard unblocked primers (U) or blocked (B) rhPrimers. The wild-type P.a. RNase H2 enzyme was titrated from 840 fmol to 210 fmol (400 mU to100 mU) and the wild-type T. kod. was titrated from 840 fmol to 52.5 fmol (equivalent of 400 mU to 25 mU of wild-type P.a.).

Figure 8:
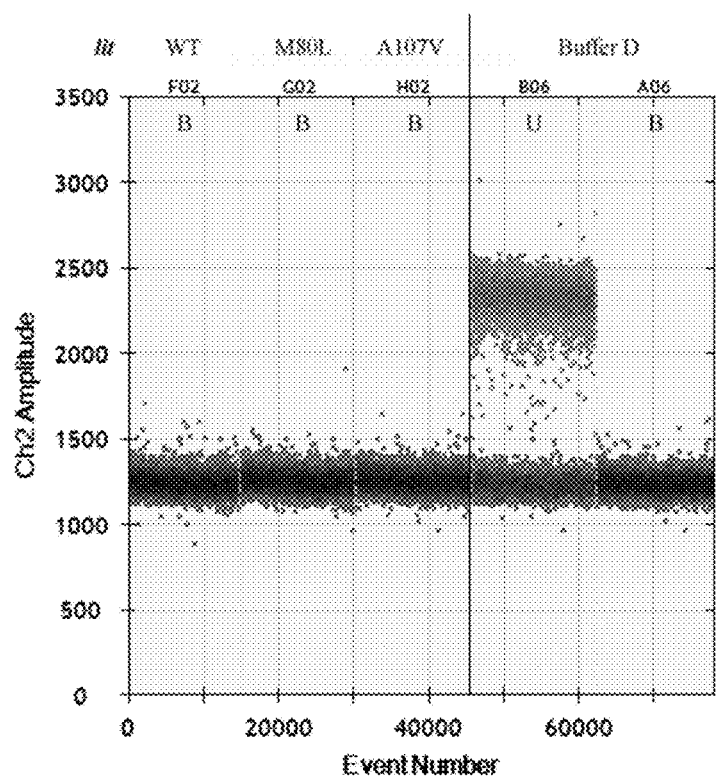

FIG. 8 is a plot from a QX-200™ DROPLET DIGITAL™ (DDPCR™) system (Bio-Rad Laboratories, Inc., Hercules, Calif.) showing a comparison of wild-type and mutant RNase H2 enzymes from *T. litoralis*. An RNase P assay was run using either standard unblocked primers (U) or blocked (B) rhPrimers and 420 fmol (equivalent of 200 mU wild-type P.a.) of the indicated mutant *T. litoralis* RNase H2 enzyme.

Figure 9:
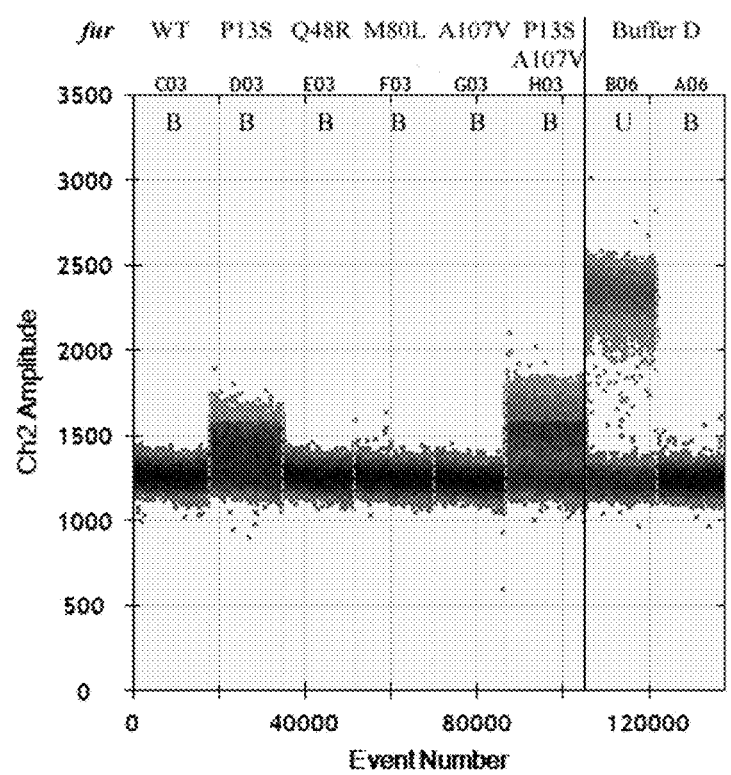

FIG. 9 is a plot from a QX-200™ DROPLET DIGITAL™ (DDPCR™) system (Bio-Rad Laboratories, Inc., Hercules, Calif.) showing a comparison of wild-type and mutant RNase H2 enzymes from *P. furiosis*. An RNase P assay was run using either standard unblocked primers (U) or blocked (B) rhPrimers and 420 fmol (equivalent of 200 mU wild-type P.a.) of the indicated mutant *P. furiosis* RNase H2 enzyme.

Figure 10:
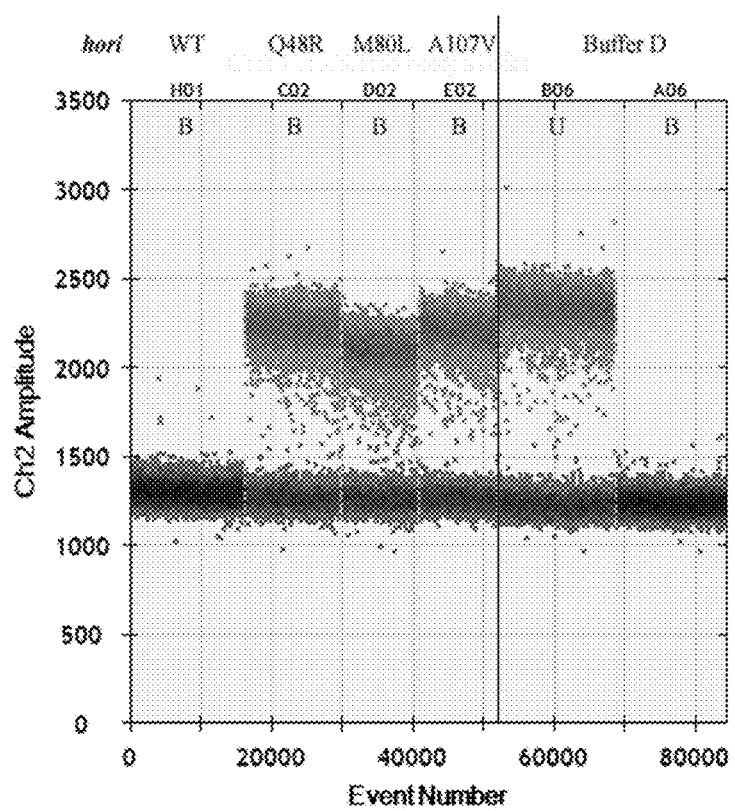

FIG. 10 is a plot from a QX-200™ DROPLET DIGITAL™ (DDPCR™) system (Bio-Rad Laboratories, Inc., Hercules, Calif.) showing a comparison of wild-type and mutant RNase H2 enzymes from *P. horikoshii*. An RNase P assay was run using either standard unblocked primers (U) or blocked (B) rhPrimers and 420 fmol (equivalent of 200 mU wild-type P.a.) of the indicated mutant *P. horikoshii* RNase H2 enzyme.

Figure 11:
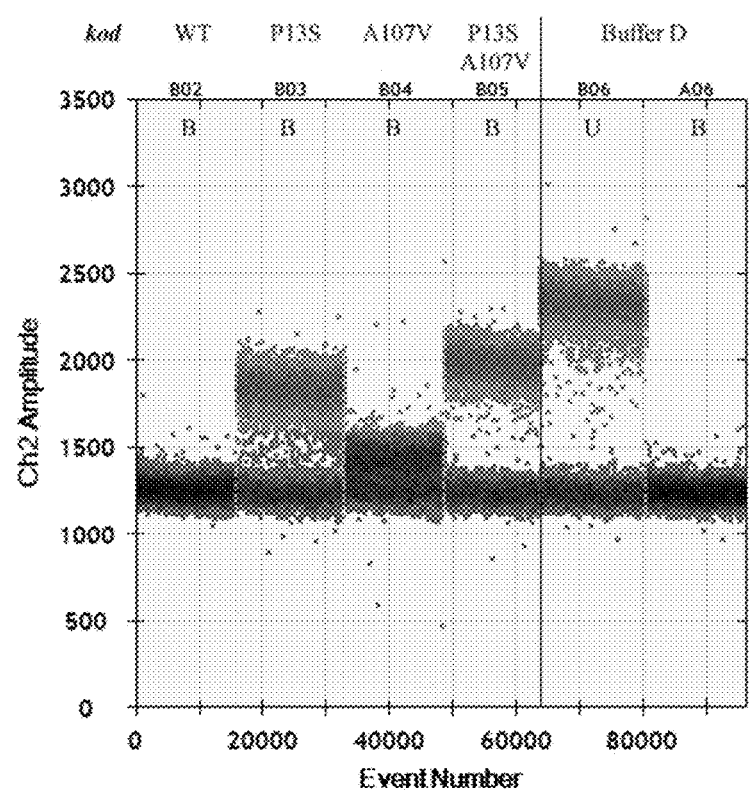

FIG. 11 is a plot from a QX-200™ DROPLET DIGITAL™ (DDPCR™) system (Bio-Rad Laboratories, Inc., Hercules, Calif.) showing a comparison of wild-type and mutant RNase H2 enzymes from *T. kodakarensis*. An RNase P assay was run using either standard unblocked primers (U) or blocked (B) rhPrimers and 4.2 fmol (equivalent of 2 mU wild-type P.a.) of the indicated mutant *T. kodakarensis* RNase H2 enzyme.

Figure 12:
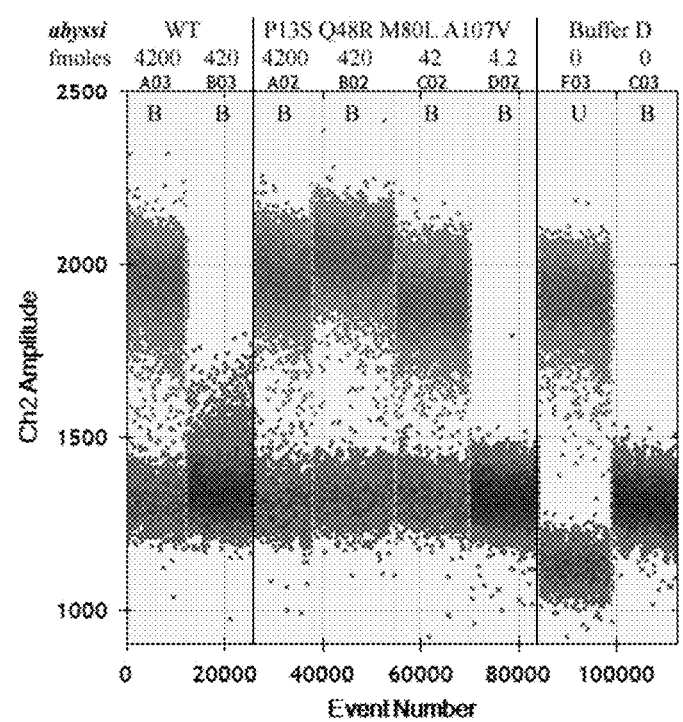

FIG. 12 is a plot from a QX-200™ DROPLET DIGITAL™ (DDPCR™) system (Bio-Rad Laboratories, Inc., Hercules, Calif.) showing a comparison of wild-type P.a. and P13S Q48R M80L A107V mutant P.a. RNase H2-titrations. An RNase P assay was run using either standard unblocked primers (U) or blocked (B) rhPrimers and 4200 fmol or 420 fmol (2000 mU to 200 mU) of the wild-type P.a. RNase H2 enzyme or a titration from 4200 fmol to 4.2 fmol (equivalent of 2000 mU to 2 mU of wild-type P.a.) of the P.a. P13S Q48R M80L A107V mutant RNase H2 enzyme.

DETAILED DESCRIPTION OF THE INVENTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention.

"Complement" or "complementary" as used herein means a nucleic acid, and can mean Watson-Crick (e.g., A-T/U and C-G) or Hoogsteen base pairing between nucleotides or nucleotide analogs of nucleic acid molecules.

"Fluorophore" or "fluorescent label" refers to compounds with a fluorescent emission maximum between about 350 and 900 nm.

"Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Primer dimers" refers to the hybridization of two oligonucleotide primers. "Stringent hybridization conditions" as used herein means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of an oligonucleotide complementary to a target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

The terms "nucleic acid," "oligonucleotide," or "polynucleotide," as used herein, refer to at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequences. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods and can contain non-nucleotide modifications such as spacers or labels. A particular nucleic acid sequence can encompass conservatively modified variants thereof (e.g., codon substitutions), alleles, orthologs, single nucleotide polymorphisms (SNPs), and complementary sequences as well as the sequence explicitly indicated.

"Polymerase Chain Reaction (PCR)" refers to the enzymatic reaction in which DNA fragments are synthesized and amplified from a substrate DNA in vitro. The reaction typically involves the use of two synthetic oligonucleotide primers, which are complementary to nucleotide sequences in the substrate DNA which are separated by a short distance of a few hundred to a few thousand base pairs, and the use of a thermostable DNA polymerase. The chain reaction consists of a series of 10 to 40 cycles. In each cycle, the substrate DNA is first denatured at high temperature. After cooling down, synthetic primers which are present in vast excess, hybridize to the substrate DNA to form double-stranded structures along complementary nucleotide sequences. The primer-substrate DNA complexes will then serve as initiation sites for a DNA synthesis reaction catalyzed by a DNA polymerase, resulting in the synthesis of a new DNA strand complementary to the substrate DNA strand. The synthesis process is repeated with each additional cycle, creating an amplified product of the substrate DNA.

A "cycling probe" reaction or "cycling probe technology (CPT)" is an isothermal signal amplification method for the detection of specific target DNA sequences. A chimeric probe DNA-RNA-DNA, and a thermostable RNase H enzyme, are the two main components of this assay. In the presence of a target sequence, a DNA/RNA hybrid is formed and RNase H specifically catalyzes the cleavage of the RNA portion of the hybrid. Since cleaved fragments are small, they dissociate spontaneously from the target sequence at the reaction temperature. The target is then recycled and available for hybridization with another probe; the reaction is inherently cyclic without external manipulations (see, e.g., U.S. Pat. No. 5,403,711, Warnon et al., *BioTechniques*, 28: 1152-1160 (2000); and Duck et al., *BioTechniques*, 9: 142-147 (1990)). Unlike PCR, products accumulate in a linear fashion.

"Loop-mediated isothermal amplification" or "LAMP" is an isothermal nucleic acid amplification method that is carried out at a constant temperature and does not require a thermal cycler, in contrast to PCR. In LAMP, a large amount of DNA is synthesized, yielding a large pyrophosphate ion by-product. Pyrophosphate ion combines with divalent metallic ion to form an insoluble salt. Adding manganous ion and calcein, a fluorescent metal indicator, to the reaction solution allows a visualization of substantial alteration of the fluorescence during the one-step amplification reaction, which takes approximately 30-60 minutes (see, e.g., Tomita et al., Nature Protocols, 3: 877-882 (2008)).

"Primer," as used herein, refers to an oligonucleotide capable of acting as a point of initiation for DNA synthesis under suitable conditions. Suitable conditions include those in which hybridization of the oligonucleotide to a template nucleic acid occurs, and synthesis or amplification of the target sequence occurs, in the presence of four different nucleoside triphosphates and an agent for extension (e.g., a DNA polymerase) in an appropriate buffer and at a suitable temperature.

"Probe" and "fluorescent generation probe" are synonymous and refer to either a) a sequence-specific oligonucleotide having an attached fluorophore and/or a quencher, and optionally a minor groove binder or b) a DNA binding reagent, such as, but not limited to, SYBR® Green dye.

"Quencher" refers to a molecule or part of a compound, which is capable of reducing the emission from a fluorescent donor when attached to or in proximity to the donor. Quenching may occur by any of several mechanisms including fluorescence resonance energy transfer, photo-induced electron transfer, paramagnetic enhancement of intersystem crossing, Dexter exchange coupling, and exciton coupling such as the formation of dark complexes.

2. RNaseH2 Cleavage Reaction

Described herein are methods for performing an RNase-mediated cleavage of one or more nucleic acid sequences of interest, which comprise providing a sample comprising one or more nucleic acid sequences of interest; and performing an RNase-mediated cleavage reaction on the one or more nucleic acid sequences. The term "RNase-mediated cleavage reaction" refers to a reaction in which an RNase enzyme catalyzes the breakage of at least one of the covalent sugar-phosphate linkages that forms the sugar-phosphate backbone of RNA. The RNase-mediated cleavage reaction may be performed as part of any method which requires RNase-mediated nucleic acid cleavage, such as, for example, an RNase H-dependent PCR (rhPCR) reaction, a loop-mediated isothermal amplification (LAMP) reaction, cycling probe technology (CPT), or any emulsion-based assay. An RNase-mediated cleavage reaction may also be used to detect homology directed repair (HDR) of double-strand DNA breaks (e.g, as a result of targeted endonuclease activity) in an RNase H-dependent PCR reaction.

3. Digital PCR System

In one embodiment, the RNase H2-mediated cleavage reaction is performed as part of a method for amplifying one or more nucleic acids of interest which comprises performing an RNase H-dependent PCR (rhPCR) reaction on a sample that contains one or more nucleic acids of interest in a digital PCR system. The one or more nucleic acid sequences of interest to be amplified also can be referred to as a "target," "target sequence," "target region," or "target nucleic acid," all of which are synonymous and refer to a region or sequence of a nucleic acid which is to be amplified, sequenced, or detected.

The term "RNase H PCR (rhPCR)" refers to a PCR reaction which utilizes "blocked" oligonucleotide primers and an RNase H enzyme. "Blocked" primers contain a blocking group that prevents extension of the primer by a polymerase, and blocked primers contain at least one chemical moiety (such as, but not limited to, a ribonucleic acid residue or a 2'fluoro base) within the primer or other oligonucleotide, such that when the blocked primer hybridizes to the template or target nucleic acid, the blocking group is removed by cleavage by an RNase H enzyme that recognizes and cleaves at the chemical moiety. Following RNase H cleavage, amplification of the target DNA can occur.

In one embodiment, the 3' end of a blocked primer can comprise the blocking group rDDDDMx, wherein relative to the target nucleic acid sequence, "r" is an RNA residue, "D" is a complementary DNA residue, "M" is a mismatched DNA residue, and "x" is a C3 spacer. A C3 spacer is a short 3-carbon chain attached to the terminal 3' hydroxyl group of the oligonucleotide, which further inhibits the DNA polymerase from binding before cleavage of the RNA residue.

The methods described herein can be performed using any suitable RNase H enzyme that is derived or obtained from any organism. Typically, RNase H-dependent PCR reactions are performed using an RNase H enzyme obtained or derived from the hyperthermophilic archaeon *Pyrococcus abyssi* (P.a.), such as RNase H2. Thus, in one embodiment, the RNase H enzyme employed in the methods described herein desirably is obtained or derived from *Pyrococcus abyssi*, preferably an RNase H2 obtained or derived from *Pyrococcus abyssi*. In other embodiments, the RNase H enzyme employed in the methods described herein can be obtained or derived from other species, for example, *Pyrococcus furiosis, Pyrococcus horikoshii, Thermococcus kodakarensis*, or *Thermococcus litoralis*.

In one embodiment, the RNase H-dependent PCR reaction is performed in a digital PCR system (i.e., digital rhPCR). "Digital PCR" refers to a PCR reaction which is carried out on a single selected starting template, wherein a number of individual templates are each isolated into separate reaction areas (see, e.g., Vogelstein et al., *PNAS*, 96: 9236-9241 (1999) and U.S. Pat. No. 6,440,706). As such, digital PCR allows for the detection and precise quantification of, for example, low-level pathogens, rare genetic sequences, quantification of copy number variants, and rare mutations (see, e.g., Manoj, P., *Mitochondrial DNA*, 27(1): 742-6 (2016)). In digital PCR, the reaction area can be, for example, a well, chamber, bead, or water-in-oil emulsion. Digital PCR reactions will yield a negative result if no starting molecule is present or a positive result if the targeted starting template is present. Analyzing the number of positive reactions allows for the quantification of the starting template. Accordingly, a large number of reaction areas can be used for a single digital PCR experiment. Any suitable digital PCR system can be used in the inventive method, many of which are known in the art and commercially available from sources such as, for example, the QX200™ DROPLET DIGITAL™ PCR system (Bio-Rad Laboratories Inc., Hercules, Calif.), the RAINDROP™ Digital PCR system (Raindance Technologies, Inc., Billerica, Mass.), the QUANTSTUDIO® 3D digital PCR system (ThermoFisher Scientific, Waltham, Mass.), and the DIGITAL ARRAY™ integrated fluid circuit (IFC) system (Fluidigm Corporation, South San Francisco, Calif.).

In one embodiment, the digital PCR system can be a droplet digital PCR system. The term "droplet digital PCR" refers to a digital PCR system in which the reaction area is a droplet of water in a well. Preferably, the digital PCR system is an emulsion droplet digital PCR system. The term "emulsion droplet digital PCR" refers to a digital PCR system in which the reaction area is a droplet that is formed in a water-oil emulsion. Techniques for performing droplet digital PCR and emulsion droplet digital PCR are known in the art and include, but are not limited to, those described in Hindson et al., *Anal Chem*, 83:8604-8610 (2011); Pinheiro et al., *Anal Chem*, 84:1003-1011 (2012); and Jones et al., *J. Virological Methods*, 202: 46-53 (2014). Droplet digital PCR systems and emulsion droplet digital PCR systems also are commercially available from sources such as, for example, the QX200™ DROPLET DIGITAL™ PCR system (Bio-Rad Laboratories, Inc., Hercules, Calif.).

The RNase H-dependent PCR reaction described herein can be performed using any suitable combination of primer and probe oligonucleotide sequences, the choice of which will depend on the sequence of the target nucleic acid to be amplified. In one embodiment, the RNase H-dependent PCR reaction is performed using one set of blocked primers and one set of unblocked primers. Suitable probes include, for example, dual-labeled probes, multi-fluorophore or multi-quencher (or combinations thereof) such as dual-quencher ZEN probes (Integrated DNA Technologies, Inc.), MGB TaqMan probes, and dual-labeled non-MGB TaqMan probes (see Hindson et al., *Anal Chem.*, 83:8604-8610 (2011)), and molecular beacon probes (see U.S. Pat. No. 6,440,706). The dual labeled probes are cleaved by polymerases with 5'-exonuclease activity. While the aforementioned probes typically are longer than 16 nucleotides, a probe used in connection with the inventive method can be of any suitable size. For example, a probe can be about 25-30 nucleotides in length, about 50-80 nucleotides in length, or about 100-150 nucleotides in length. Examples of specific primer and probe sequences that can be used in the inventive method are set forth below in the Examples.

In one embodiment, a combination of two or more probes can be used when two or more target nucleic acid sequences are amplified by the inventive method. For example, two probes can be used to identify two targets in droplets, such that four populations can exist within a particular PCR reaction: no target present (Probe1−/Probe2−), one of two targets present (Probe1+/Probe2− or Probe1−/Probe2+), or both of targets present (Probe1+/Probe2+). The choice of an appropriate combination of probes specific for a particular combination of target nucleic acid sequences is well within the skill in the art, and such probes can be designed and generated using routine methods known in the art.

As discussed above, a skilled artisan will appreciate that a probe oligonucleotide can comprise a fluorophore and/or a quencher attached thereto. The probe used in the inventive method can comprise any suitable fluorophore and/or quencher attached thereto. Suitable fluorophores include, for example, 5-FAM (also called 5-carboxyfluorescein, also known as Spiro(isobenzofuran-1(3H), 9'-(9H)xanthene)-5-carboxylic acid, 3',6'-dihydroxy-3-oxo-6-carboxyfluorescein), 5-Hexachloro-Fluorescein, ([4,7,2',4',5',7'-hexachloro-(3',6'-dipivaloylfluoresceinyl)-6-carboxylic acid]), 6-Hexachloro-Fluorescein, ([4,7,2',4',5',7'-hexachloro-(3',6'-dipivaloylfluoresceinyl)-5-carboxylic acid]), 5-Tetrachloro-Fluorescein, ([4,7,2',7'-tetra-chloro-(3',6'-dipivaloylfluoresceinyl)-5-carboxylic acid]), 6-Tetrachloro-Fluorescein, ([4,7,2',7'-tetrachloro-(3',6'-dipivaloylfluoresceinyl)-6-carboxylic acid]), 5-TAMRA (5-carboxytetramethylrhodamine); Xanthylium, 9-(2,4-dicarboxyphenyl)-3,6-bis(dimethyl-amino), 6-TAMRA (6-carboxytetramethylrhodamine), 9-(2,5-dicarboxyphenyl)-3,6-bis(dimethylamino), EDANS (5-((2-aminoethyl)amino)naphthalene-1-sulfonic acid), 1,5-IAEDANS (5-((((2-iodoacetyl)amino)ethyl)amino)naphthalene-1-sulfonic acid), Cy5 (Indodicarbocyanine-5); Cy3 (Indo-dicarbocyanine-3), and BODIPY FL (2,6-dibromo-4,4-difluoro-5,7-dimethyl-4-bora-3a,4a-diaza-s-indacene-3-proprionic acid), Quasar®-670 dye (Biosearch Technologies), Cal Fluor® Orange dye (Biosearch Technologies), ATTO Dyes (Atto-Tec GmbH), Rox dyes, Max dyes (Integrated DNA Technologies), and derivatives thereof.

Prior to amplification of a target nucleic acid, a quencher prevents the fluorophore signal from being detected. Any suitable quencher can be used in the invention, such as, for example, DABCYL, BLACK HOLE™ Quenchers (such as, BHQ-1®, BHQ-2®, and BHQ-3®), IOWA BLACK® FQ, and IOWA BLACK® RQ, all of which are commercially available from a variety of sources. During amplification of the target nucleic acid by DNA polymerase, the fluorophore and/or quencher can be cleaved and separated, allowing the detection of the fluorophore signal. The fluorescence intensity is proportional to the amount of amplified product and allows for quantification of a target nucleic acid.

4. Mutant RNase H Enzyme

The method described herein involves an RNase H2-dependent cleavage reaction which comprises a mutant RNase H enzyme, such as a mutant RNase H2 enzyme obtained or derived from *Pyrococcus abyssi* (P.a.), *Pyrococcus furiosis* (P. fur), *Pyrococcus horikoshii* (P. hori), *Thermococcus kodakarensis* (T. kod), or *Thermococcus litoralis* (T. lit). By "mutant" is meant that the amino acid sequence of the RNase H2 described herein comprises a deletion, insertion, or substitution of one or more amino acid residues as compared to a wild-type or naturally occurring RNase H2 amino acid sequence. Mutant enzymes may be designed by suitable techniques known in the art, such as by standard site-directed mutagenesis methods (also called site-specific mutagenesis or oligonucleotide-directed mutagenesis) (see, e.g., Weiner M. et al., *Gene*, 151:119-123 (1994)). Site-directed mutagenesis may be performed using one or more oligonucleotide primers, with each primer bearing at least one mutated nucleic acid residue relative to the wild-type RNase H2 sequence. In one embodiment, each primer for site-specific mutagenesis can contain at least three nucleic acid mutations. In another embodiment, the mutations occur at consecutive nucleic acid residues. Mutant enzymes may be expressed in a suitable host, such as bacteria, and purified by any suitable technique known in the art, such as those described in, for example, Sambrook et al., *Molecular Cloning: A Laboratory Manual*, 4th ed., Cold Spring Harbor Press, Cold Spring Harbor, N.Y. (2012); and Ausubel et al., *Current Protocols in Molecular Biology*, John Wiley & Sons, New York (2016). In one embodiment, for example, a nucleic acid sequence encoding a mutant RNase H enzyme generated by site-specific mutagenesis can be expressed in *E. coli*, purified by NiNTA chromatography, and re-suspended in Buffer F (20 mM Tris-HCl pH 8.4, 100 mM KCl, 0.1 M EDTA, 0.1% TRITON X-100™, and 50% glycerol), as described in, e.g., U.S. Pat. No. 8,911,948.

The activity of a mutant RNase H enzyme can be evaluated based on the amplification efficiency of a known starting quantity of a template in an RNase H2-dependant PCR reaction (rhPCR). In one embodiment, for example, the starting template can be the human RNASE P gene, and activity of a particular mutant RNase H enzyme can be measured using an RNase P (RNP) assay. An "RNase P (RNP) assay" is a method of evaluating enzymatic activity by quantifying amplification of RNASE P. An RNP assay utilizes two oligonucleotide primers in combination with a probe, and allows for the addition of an enzyme, such as, for example, RNase H2. Other RNase H2 assay methods are well known to those of skill in the art.

Examples of mutant P.a. RNase H2 enzyme amino acid sequences that can be used in connection with the methods described herein include, but are not limited to, SEQ ID NO: 1, SEQ ID NO: 2, SEQ ID NO: 3, SEQ ID NO: 4, SEQ ID NO: 5, SEQ ID NO: 6, SEQ ID NO:7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 70, SEQ ID NO: 71, SEQ ID NO: 73, SEQ ID NO: 74, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 90, and SEQ ID NO: 165, or an amino acid sequence that is at least 90% identical (e.g., 90%, 91%, 92%, 93%, 94% identical), and preferably at least 95% identical (e.g., 95%, 96%, 97%, 98%, 99%, or 100% identical) to any of the foregoing amino acid sequences. More preferably, the mutant P.a. RNase H2 enzyme comprises the amino acid sequence of SEQ ID NO: 1, SEQ ID NO: 2, SEQ ID NO:7, SEQ ID NO:8, SEQ ID NO:13, SEQ ID NO:15, SEQ ID NO: 16, SEQ ID NO:17, SEQ ID NO:18, or SEQ ID NO:20, SEQ ID NO: 70, SEQ ID NO: 71, SEQ ID NO: 73, SEQ ID NO: 74, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 90, and SEQ ID NO: 165.

Examples of mutant *Pyrococcus furiosis* RNase H2 enzyme amino acid sequences that can be used in connection with the methods described herein include, but are not limited to, SEQ ID NO: 126, SEQ ID NO: 127, SEQ ID NO: 128, SEQ ID NO: 129, and SEQ ID NO: 130. Examples of mutant *Pyrococcus horikoshii* RNase H2 enzyme amino acid sequences that can be used in connection with the methods described herein include, but are not limited to, SEQ ID NO: 131, SEQ ID NO: 132, and SEQ ID NO: 133. Examples of mutant *Thermococcus kodakarensis* RNase H2 enzyme amino acid sequences that can be used in connection with the methods described herein include, but are not limited to, SEQ ID NO: 134, SEQ ID NO: 135, and SEQ ID NO:136. Examples of mutant *Thermococcus litoralis* RNase H2 enzyme amino acid sequences that can be used in connection with the methods described herein include, but are not limited to, SEQ ID NO: 137 and SEQ ID NO: 138.

In another embodiment, a mutant *Pyrococcus furiosis* RNase H2 enzyme can comprise an amino acid sequence comprising SEQ ID NO: 95 except for one or more of the following amino acid substitutions: A9S, R11K, P13S, E48R, M80L, A107V, P171G, S172I, D173E, E199Y, E199G, and/or F220L. In another embodiment, a mutant *Pyrococcus horikoshii* RNase H2 enzyme can comprise an amino acid sequence comprising SEQ ID NO: 96 except for one or more of the following amino acid substitutions: A9S, R11K, P13S, Q48R, M80L, A107V, P171G, S172I, D173E, E199Y, E199G, and/or F218L. In another embodiment, a mutant *Thermococcus kodakarensis* RNase H2 enzyme can comprise an amino acid sequence comprising SEQ ID NO: 97 except for one or more of the following amino acid substitutions: A9S, R11K, P13S, A107V, P171G, S172I, D173E, K199Y, K199G, K199E, and/or Y224L. In a further embodiment, a mutant *Thermococcus litoralis* RNase H2 enzyme can comprise an amino acid sequence comprising SEQ ID NO: 98 except for one or more of the following amino acid substitutions: A9S, R11K, P13S, M80L, A107V, P171G, S172I, D173E, K199Y, K199G, K199E, and/or F220L. As discussed above, the mutant RNase H2 enzyme also can comprise an amino acid sequence that is at least 90% identical (e.g., 90%, 91%, 92%, 93%, 94% identical), and preferably at least 95% identical (e.g., 95%, 96%, 97%, 98%, 99%, or 100% identical) to any of the foregoing amino acid sequences.

In addition to digital PCR systems, such as digital droplet PCR (ddPCR) and emulsion droplet digital PCR, the mutant RNase H enzymes described herein can be used in other nucleic acid amplification and detection assays, including, but not limited to, "hot start" assays (e.g., hot start PCR), Cycling Probe Technology (CPT), rolling circle amplification (RCA), helicase dependent amplification (HDA), oligonucleotide ligation assay (OLA), ligation chain reaction (LCR), polynomial amplification, and DNA sequencing.

"Hot start" PCR is a modified form of PCR which avoids a non-specific amplification of DNA by inactivating the Taq polymerase at lower temperatures. Specifically, hot start assays employ a modified oligonucleotide that is unable to participate in the PCR reaction until it hybridizes to a complementary nucleic acid sequence, and is cleaved to generate a functional 5'- or 3'-end. Hot start protocols provide enhanced specificity as compared to corresponding assays which utilize standard unmodified DNA oligonucleotides. In addition, the requirement for reversibly inactivated DNA polymerases or DNA ligases is eliminated. In one embodiment, the hot start component can be a thermostable RNase H or other nicking enzyme that gains activity at the elevated temperatures employed in the reaction. Other assays that can be performed with the mutant RNase H enzymes described herein include, e.g., primer extension assays (including PCR, DNA sequencing, and polynomial amplification), cycling probe reactions, sequencing by ligation, and sequencing by generation of end-labeled fragments.

In OLA, a set of two or more oligonucleotides in combination with a thermostable Taq DNA ligase are used to discriminate single-nucleotide polymorphism alleles. One probe is an allele-specific probe that hybridizes to a target DNA so that the 3' base is situated directly over the SNP nucleotide, and the other probe hybridizes to the template upstream of the SNP polymorphic site providing a 5' end for the ligation reaction. Only when the allele-specific probe matches the target DNA can ligation occur. In LCR, for each of the two DNA strands, two partial probes are ligated to form one probe; thus LCR uses two enzymes: a DNA polymerase and a thermostable DNA ligase. In other embodiments, where readout depends upon a PCR assay to amplify the product of a ligation event, any blocking group may be placed in the domain of the oligonucleotide of the invention that is removed by RNase H cleavage. In such embodiments, the precise position of the blocking group in the RNase H cleavable domain may be adjusted to alter specificity for cleavage and precise placement of the blocking group relative to the cleavable RNA bases may alter the amount of enzyme needed to achieve optimal cleavage rates.

For ligation assays (e.g., OLA and LCR), a modification which inhibits polymerase extension and/or ligation activity may be located at or near either the 3'- or 5'-end of the oligonucleotide. In other embodiments, a modification which inhibits polymerase extension and/or ligation activity, if used, is preferably placed within the domain that is 3' to the cleavable RNA base in the region that is removed by probe cleavage. In other embodiments, C3 spacers may be positioned close to the RNA base in the oligonucleotide probes described herein to improve specificity that is helpful for improving mismatch discrimination.

5. Sample

The methods described herein desirably are practiced on a sample comprising one or more nucleic acid sequences.

"Sample" or "biological sample" or "specimen" are synonymous and refer to a sample obtained from a subject. The sample can comprise a nucleic acid, for example a deoxyribonucleic acid (DNA) and/or a ribonucleic acid (RNA). The sample may be obtained from a subject as defined herein, which is preferably a mammal, and more preferably a human (e.g., a human comprising a rare allele or mutation). The subject may also include non-human animals, for example, all mammalian and non-mammalian vertebrates (such as, but not limited to, non-human primates, sheep, dogs, cats, cows, pigs, horses, rodents, poultry, amphibians, and reptiles). The sample can be, for example, a biological fluid (e.g., blood, urine, semen, saliva, cerebrospinal fluid, amniotic fluid, etc.), a tissue biopsy, curettage, fine needle aspirate, and ex vivo cell or tissue culture.

6. Kit for Cleaving a Target Sequence(s)

The invention described herein also comprises a kit for cleaving a target sequence in an RNase H2-dependent cleavage reaction in an emulsion, such as an RNase H-dependent PCR (rhPCR) reaction (e.g., an emulsion droplet digital PCR system), a loop-mediated isothermal amplification (LAMP) reaction, or cycling probe technology (CPT) as described herein. The kit desirably comprises a mutant RNase H2 enzyme, such as those described herein, in combination with one or more reagents for performing an RNase H2-mediated cleavage reaction on a sample. Examples of suitable reagents for inclusion in the kit include, for example, a wild-type RNase H2 enzyme (for a control), a blocking agent, a labeling agent, one or more primers, a buffer, a metaphase spread, and the like. Many such reagents are described herein or otherwise known in the art and commercially available.

7. Examples

The following examples further illustrate the invention but should not be construed as in any way limiting its scope.

Example 1

This example demonstrates the failure of wild-type P.a. RNase H2 enzyme to perform in an emulsion droplet digital PCR (ddPCR) assay.

An RNase P assay (RNP assay) was first used to evaluate the activity of the wild-type P.a. RNase H2 enzyme in a digital rhPCR system. In an RNP assay, the target nucleic acid is a known quantity of the human RNASE P gene. The RNP assay was conducted with a dilution series of the wild-type RNase H2 enzyme using the QX-200™ DROPLET DIGITAL™ (DDPCR™) system (Bio-Rad Laboratories, Inc., Hercules, Calif.). This system provides absolute quantification of target nucleic acid molecules (DNA or RNA) for EVAGREEN® (Bio-Rad Laboratories) or probe-based digital PCR applications.

RNASE P nucleic acid samples were prepped for PCR by adding a master mix containing a probe and either unblocked or blocked RNP primers. Unblocked primers, which do not require cleavage by RNase H2 to become functional, were used as controls. Blocked primers included a ribonucleotide residue that prevents primer dimer formation, and this residue must be cleaved by RNase H2 in order for product amplification to occur in a PCR system. The specific probe and primer nucleotide sequences used in the assay are set forth in Table 1. In Table 1, DNA nucleotides are shown in uppercase, and RNA nucleotides are shown in lowercase. HEX (6-carboxy-2',4,4',5',7,7'-hexachlorofluorescein) is a fluorescent dye, and FQ is IOWA BLACK® FQ fluorescent quencher. X is a C3 propanediol spacer utilized to prevent primer extension prior to RNase H2 cleavage of the primer.

TABLE 1

RNase P Primers and Probe Sequences

| Oligonucleotide | Oligonucleotide Sequence | SEQ ID NO. |
|---|---|---|
| Unblocked RNP Primer1 | GCGGAGGGAAGCTCATCAG | 23 |
| Unblocked RNP Primer2 | CCCTAGTCTCAGACCTTCCCAA | 24 |
| RNP Probe (HEX) | HEX-CCACGAGCTGAGTGCGTCCTGTCA-FQ | 25 |
| Blocked RNP Primer1 | GCGGAGGGAAGCTCATCAGuGGGGG-x | 26 |
| Blocked RNP Primer2 | CCCTAGTCTCAGACCTTCCCAAgGGACA-x | 27 |

For each 20 µl reaction volume, either 4200 fmol (210 nM or 2000 mU), 3150 fmol (157.5 nM or 1500 mU), 2100 fmol (105 nM or 1000 mU), or 420 fmol (21 nM or 200 mU) of the wild-type RNase H2 enzyme was added to a mix containing 1× ddPCR Supermix for Probes (no dUTP) (Bio-Rad), 900 nM of blocked or unblocked RNP primers, 250 nM probe, and 5×10$^4$ copies GBLOCK® RNase P template (Integrated DNA Technologies (IDT), Coralville, Iowa). Reactions containing unblocked primers served as controls to ensure viability of the digital rhPCR system.

Figure 1:
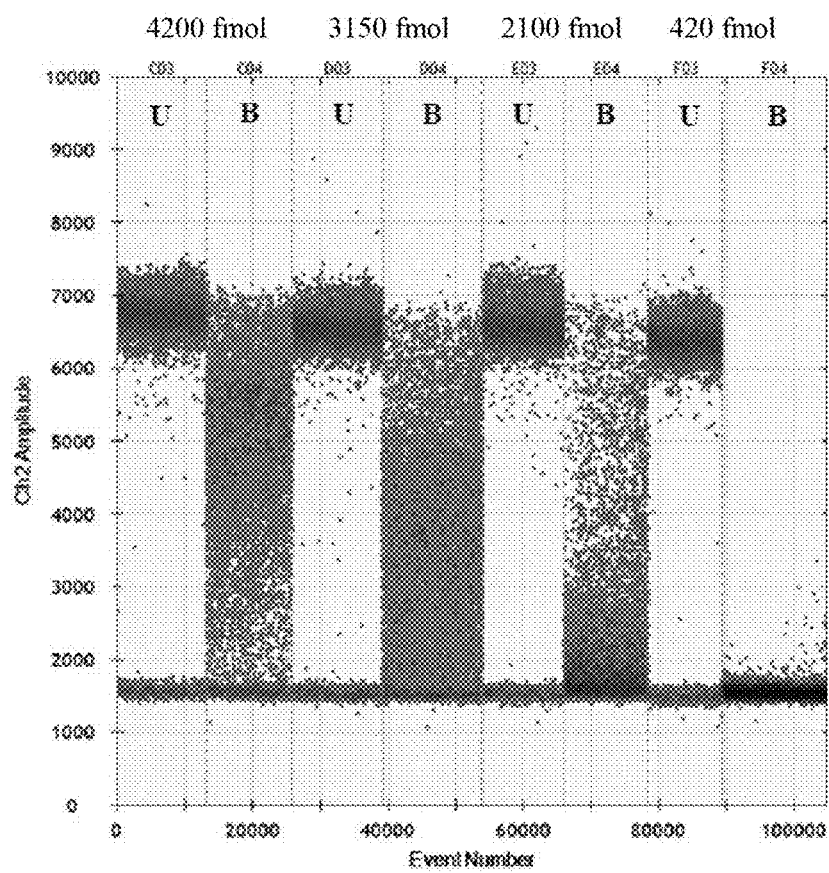
FIG. 1 is a plot from a QX-200™ DROPLET DIGITAL™ (DDPCR™) system (Bio-Rad Laboratories, Inc., Hercules, Calif.) showing a wild-type *Pyrococcus abyssi* (P.a.) RNase H2 titration in a droplet digital rhPCR system. An RNase P (RNP) assay was run using either unblocked (U) primers, or blocked (B) rhPrimers with 4200, 3150, 2100, or 420 fmol of wild-type P.a. RNase H2. Fluorescence intensity (Y-axis) was plotted for each droplet (event number, X-axis).

The samples were then emulsified using the BIO-RAD® AUTOMATED DROPLET GENERATOR™ (Bio-Rad) system, which generates up to 20,000 uniform nanoliter-sized water-in-oil droplets within each sample. Within the droplets, the target DNA was randomly distributed, and each droplet served to partition the reactions. The fraction of PCR-positive droplets was used to quantify the target nucleic acid according to the Poisson distribution. Digital rhPCR was then performed using the primers and probes listed in Table 1, and each of the 20,000 droplets was analyzed for an increase in fluorescence intensity on a BIO-RAD® QX-200™ DROPLET DIGITAL™ Reader. An increase in fluorescence intensity indicated a positive reaction, while no fluorescence indicated that amplification of the target nucleic acid did not occur. The fluorescence intensity was then plotted for each droplet (event number), using the QUANTASOFT™ v1.7 software (Bio-Rad). The results are shown in FIG. 1. Reactions with unblocked primers (U) exhibited tight bands with high fluorescent expression, indicative of successful amplification of the template DNA. In contrast, reactions with blocked primers (B) exhibited a characteristic "rain" effect with 4200 fmol, 3150 fmol, and 2100 fmol of wild-type RNase H2, indicative of poor amplification of the template DNA. This was a direct result of poor wild-type RNase H2 activity in the emulsion, which causes the primers to remain blocked and reduces the efficacy of the amplification reaction. Amplification did not occur at all with blocked primers at 420 fmol of wild-type P.a. RNase H2.

These results confirm that wild-type P.a. RNase H2 is not effective in an emulsion droplet digital PCR system.

Example 2

This example describes the use of mutant P.a. RNase H2 enzymes in an emulsion droplet digital PCR (ddPCR) assay.

To determine whether a mutated P.a. RNase H2 enzyme could exhibit improved performance as compared to the wild-type P.a. RNase H2 in an emulsion-based digital PCR assay, a series of 22 mutants were created with respect to the wild-type enzyme by standard site-directed mutagenesis methods (see Weiner et al., Gene, 151:119-123 (1994)) using the oligonucleotide primers in Table 2. Mutant RNase H enzyme sequences were codon optimized for expression in E. coli using the Integrated DNA Technologies Codon Optimization web tool (www.idtdna.com/CodonOpt). Each mutant enzyme contained at least one amino acid substitution. As shown in Table 2, each mutant was designated according to the amino acid residue number where the substitution occurred, preceded by the original amino acid, and proceeded by the substituted amino acid.

TABLE 2

| Mutant ID | Amino acid change | Mutant Amino Acid Sequence SEQ ID NO: | Sense Mutagenesis Oligonucleotide SEQ ID NO: | Antisense Mutagenesis Oligonucleotide SEQ ID NO: |
|---|---|---|---|---|
| 1 | A9S | 1 | 28 | 29 |
| 2 | R11K | 2 | 30 | 31 |
| 3 | R11Q | 3 | 32 | 33 |
| 4 | G12A | 4 | 34 | 35 |
| 5 | G12T | 5 | 36 | 37 |
| 6 | G12C | 6 | 38 | 39 |
| 7 | P13S | 7 | 40 | 41 |
| 8 | P13T | 8 | 42 | 43 |
| 9 | P13E | 9 | 44 | 45 |
| 10 | V14L | 10 | 46 | 47 |
| 11 | V14F | 11 | 48 | 49 |
| 12 | G169A | 12 | 50 | 51 |
| 13 | P171G | 13 | 52 | 53 |
| 14 | S172T | 14 | 54 | 55 |
| 15 | S172G | 15 | 56 | 57 |
| 16 | S172I | 16 | 58 | 59 |
| 17 | S172H | 17 | 60 | 61 |
| 18 | D173E | 18 | 62 | 63 |
| 19 | K149R | 19 | 64 | 65 |
| 20 | A9S R11K | 20 | 28, 30 | 29, 31 |

TABLE 2-continued

| Mutant ID | Amino acid change | Mutant Amino Acid Sequence SEQ ID NO: | Sense Mutagenesis Oligonucleotide SEQ ID NO: | Antisense Mutagenesis Oligonucleotide SEQ ID NO: |
|---|---|---|---|---|
| 21 | R11A | 21 | 66 | 67 |
| 22 | S172Q | 22 | 68 | 69 |

The RNase H mutants were expressed in E. coli, purified by NiNTA chromatography, and re-suspended in Buffer F (20 mM Tris-HCl pH 8.4, 100 mM KCl, 0.1 M EDTA, 0.1% Triton X-100, and 50% glycerol). Techniques for purification were identical to those previously described for purifying HIS-tagged wild-type P.a. RNase H2 (see U.S. Pat. No. 8,911,948).

The mutant enzymes were characterized to determine their functional activity using a previously described synthetic rhPCR assay (see U.S. Pat. No. 8,911,948). The enzymatic activity of each mutant relative to wild-type P.a. RNase H2 is shown in Table 3.

TABLE 3

| Mut ID # | Amino acid change | Mutant Amino Acid Sequence SEQ ID NO: | U/μg | % of wild-type activity | 1 mU = x fmol |
|---|---|---|---|---|---|
| | Wild-type RNase H2 | 125 | 17.3 | 100.0% | 2.1 |
| 1 | A9S | 1 | 5.2 | 30.1% | 7 |
| 2 | R11K | 2 | 5.2 | 30.1% | 7 |
| 3 | R11Q | 3 | 2.6 | 15.0% | 14 |
| 4 | G12A | 4 | 0.65 | 3.8% | 55.9 |
| 5 | G12T | 5 | 2.6 | 15.0% | 14 |
| 6 | G12C | 6 | 2.6 | 15.0% | 14 |
| 7 | P13S | 7 | 2.6 | 15.0% | 14 |
| 8 | P13T | 8 | 2.6 | 15.0% | 14 |
| 9 | P13E | 9 | 2.6 | 15.0% | 14 |
| 10 | V14L | 10 | 1.3 | 7.5% | 27.9 |
| 11 | V14F | 11 | 0.65 | 3.8% | 55.9 |
| 12 | G169A | 12 | 0.27 | 1.6% | 134.6 |
| 13 | P171G | 13 | 2.6 | 15.0% | 14 |
| 14 | S172T | 14 | 2.5 | 14.5% | 14.5 |
| 15 | S172G | 15 | 1.3 | 7.5% | 27.9 |
| 16 | S172I | 16 | 2.6 | 15.0% | 14 |
| 17 | S172H | 17 | 1.3 | 7.5% | 27.9 |
| 18 | D173E | 18 | 2.6 | 15.0% | 14 |
| 19 | K149R | 19 | 2.6 | 15.0% | 14 |
| 20 | A9S R11K | 20 | 5.2 | 30.1% | 7 |
| 21 | R11A | 21 | 0.028 | 0.2% | 1297.5 |
| 22 | S172Q | 22 | 0.65 | 3.8% | 55.9 |

Once activity was determined, the mutant RNase enzymes were further tested using the previous described digital rhPCR RNP assay.

For each 20 μl reaction volume, 420 fmol (21 nM) of each RNase H2 enzyme was added to a mix containing 1× ddPCR Supermix for Probes (No dUTP) (Bio-Rad Laboratories, Inc., Hercules, Calif.), 900 nM of blocked or unblocked RNP primers, 250 nM probe, and 5×10⁴ copies GBLOCK® RNase P template (Integrated DNA Technologies (IDT), Coralville, Iowa). Reactions containing unblocked primers served as controls to ensure viability of the digital rhPCR system.

Figure 2:
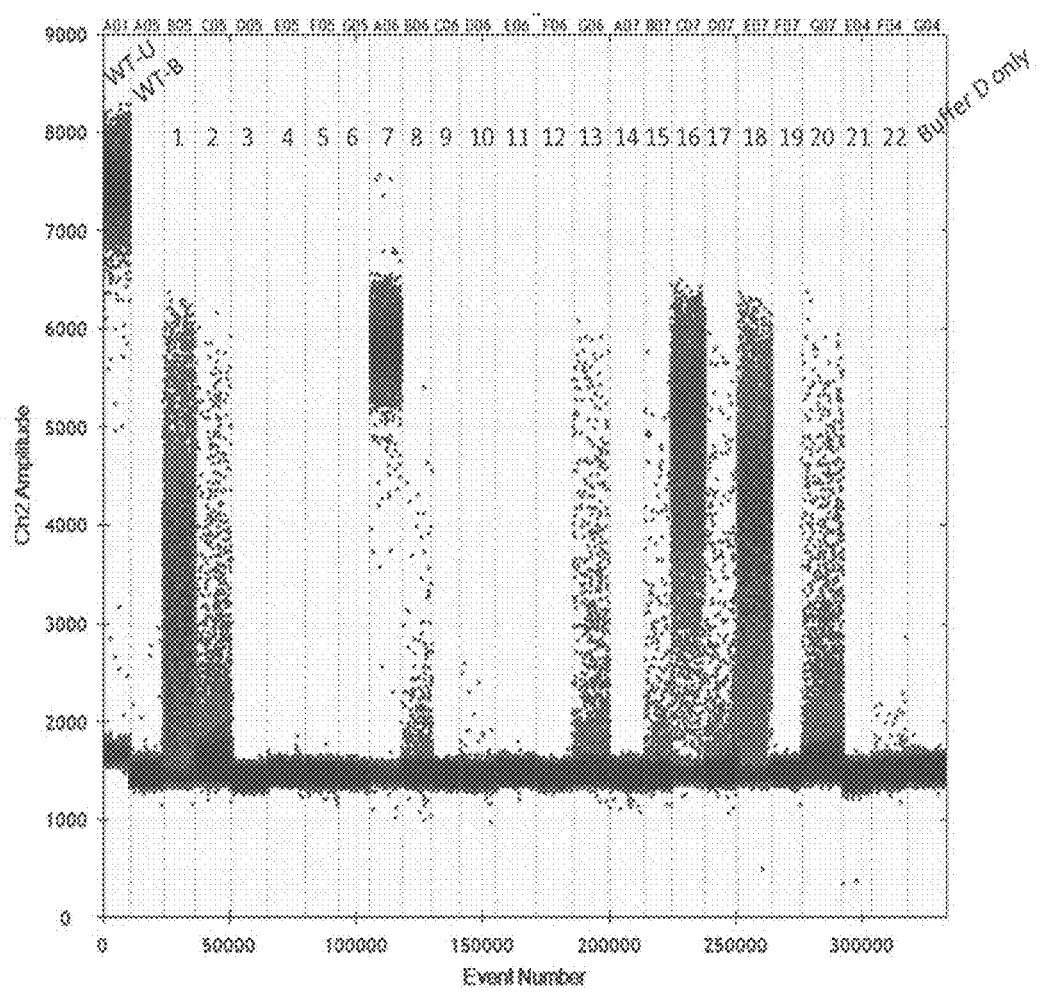
FIG. 2 is a plot showing wild-type (WT) and mutant RNase H2 enzyme activities in a digital droplet rhPCR system using the QX-200™ DROPLET DIGITAL™ (DDPCR™) system (Bio-Rad). An RNase P (RNP) assay was run using either unblocked or blocked rhPrimers, and 420 fmol (21 nM) of each RNase H2 enzyme. Only the results with the wild-type enzyme are shown for the unblocked primers (WT-U). The results with blocked rhPrimers are shown for both the wild-type (WT-B) and the mutant enzymes (numbered lanes).

The samples were emulsified using the Bio-Rad® Automated Droplet Generator™ (Bio-Rad® Laboratories, Inc., Hercules, Calif.) system, which generated 20,000 uniform nanoliter-sized water-in-oil droplets within each sample. The target DNA was randomly distributed among the droplets, and each droplet served to partition the reactions. The fraction of PCR-positive droplets was used to quantify the target nucleic acid according to the Poisson distribution. Digital rhPCR was then performed using the primers and probes listed in Table 1, and each of the 20,000 droplets was analyzed for an increase in fluorescence intensity on a Bio-Rad® QX-200™ Droplet Digital™ Reader. An increase in fluorescence intensity indicated a positive reaction, while no fluorescence indicated that amplification of the target nucleic acid did not occur. The fluorescence intensity was then plotted for each droplet (event number) using the QUANTASOFT™ v1.7 software (Bio-Rad® Laboratories, Inc., Hercules, Calif.). Reactions with unblocked primers (U) exhibited tight bands with high fluorescent expression, indicative of successful amplification of the template DNA. The results of this assay are shown in FIG. 2. Almost no amplification of the RNASE P template occurred in the reaction mixtures containing blocked primers and wild-type RNase H2 (WT-B, relative to reactions that contained unblocked primers), consistent with the results shown in FIG. 1. However, several reactions containing mutated RNase H2 enzymes showed an improvement in amplification efficacy; in particular, mutants A9S (SEQ ID NO: 1), R11K (SEQ ID NO: 2), P13S (SEQ ID NO: 7), P13T (SEQ ID NO: 8), P171G (SEQ ID NO: 13), S172G (SEQ ID NO: 15), S172I (SEQ ID NO: 16), S172H (SEQ ID NO: 17), D173E (SEQ ID NO: 18), and A9S R11K (SEQ ID NO: 20) exhibited greater amplification of the RNASE P template as compared to reactions containing the wild-type RNase H2 enzyme.

Similar to the results shown in FIG. 1, successful reactions with mutant RNase H2 enzymes manifested as a band of positive reactions with high fluorescence intensities. Of the mutant enzymes tested, P13S (SEQ ID NO: 7) exhibited the highest level of activity, producing a distinct band that exhibited a fluorescent signal intensity nearing that of the unblocked control reactions. Additionally, the quantitative value obtained for the RNASE P template was similar between the P13S mutant and that of the wild-type RNase H2 enzyme (2450 copies/µl, data not shown), indicating that successful amplification of the product was achieved by both the wild-type and the mutant enzymes.

Example 3

This example describes the effect of different concentrations of a mutant P.a. RNase H2 enzyme in an emulsion droplet digital PCR (ddPCR) assay.

To further evaluate the functionality of the P13S RNase H2 mutant, a titration of this enzyme ranging from 420 fmoles (21 nM) to 26 fmoles (1.3 nM) was performed, and the activity of each dilution was evaluated using an RNP assay in a digital rhPCR system.

For each 20 µl reaction volume, either 420 fmol (21 nM), 210 fmol (10.5 nM), 105 fmol (5.25 nM), 52 fmol (2.6 nM), or 26 fmol (1.3 nM) of the P13S mutant RNase H2 enzyme was added to a mix containing 1× ddPCR Supermix for Probes (No dUTP) (Bio-Rad Laboratories, Inc., Hercules, Calif.), 900 nM of blocked or unblocked RNP primers, 250 nM probe, and $5\times10^4$ copies GBLOCK® RNase P template (Integrated DNA Technologies (IDT), Coralville, Iowa). Reactions containing unblocked primers served as controls to ensure viability of the digital rhPCR system.

The samples were then emulsified using the Bio-Rad® Automated Droplet Generator™ (Bio-Rad® Laboratories, Inc., Hercules, Calif.) system, which generated up to 20,000 uniform nanoliter-sized water-in-oil droplets within each sample. The target DNA was randomly distributed among the droplets, and each droplet served to partition the reactions. The fraction of PCR-positive droplets was used to quantify the target nucleic acid according to the Poisson distribution. Digital rhPCR was then performed using the primers and probes listed in Table 1, and each of the 20,000 droplets was analyzed for an increase in fluorescence intensity on a Bio-Rad® QX-200™ Droplet Digital™ Reader. An increase in fluorescence intensity indicated a positive reaction, while no fluorescence indicated that amplification of the target nucleic acid did not occur. The fluorescence intensity was then plotted for each droplet (event number) using the QUANTASOFT® v1.7 software (Bio-Rad® Laboratories, Inc., Hercules, Calif.).

Figure 3:
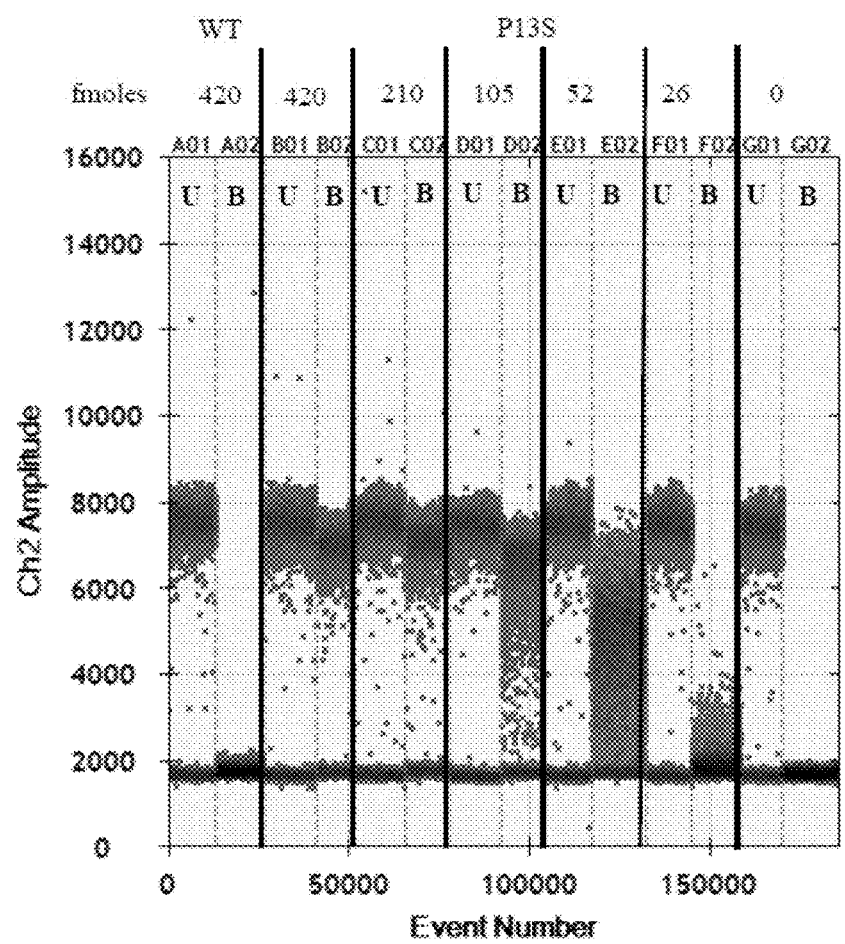
FIG. 3 is a plot showing the titration of P13S mutant RNase H2 in a digital droplet rhPCR system. The RNase H2 enzyme P13S was titrated from 420 fmoles to 26 fmoles and evaluated with an RNase P (RNP) assay with either standard unblocked (U) primers or blocked (B) rhPrimers.

The results of this experiment are shown in FIG. 3. The signal intensity of the PCR reaction was decreased in samples containing blocked RNP primers (B) compared to those with unblocked primers (U); however, the P13S mutant (SEQ ID NO: 7) exhibited successful amplification of the RNP template with 420 and 210 fmoles (21 and 10.5 nM, respectively), and good concentration calls were obtained down to 105 fmoles (5.25 nM) of enzyme. Beginning at 105 fmoles of the P13S mutant enzyme, the amplification efficacy of the reaction began to decline, as indicated by a widening band of fluorescent intensities. Efficacy continued to decline at 52 fmoles and 26 fmoles. These results demonstrate that P13S performs ideally when present in a reaction at greater than 210 fmoles.

The results of this example demonstrate that nucleic acid sequences can be amplified in an RNase H-dependent PCR reaction using a mutant *Pyrococcus abyssi* (P.a.) RNase H2 enzyme in accordance with the inventive method. Additionally, the P13S mutant (SEQ ID NO: 7) is effective at lower concentrations.

Example 4

This example demonstrates the use of additional P.a. RNase H2 mutant enzymes in an emulsion-based digital droplet PCR assay.

A total of 26 mutant RNase H2 enzymes were created by using standard site-directed mutagenesis in an emulsion system (see Weiner M., et al., *Gene*, 151:119-123 (1994)) and oligonucleotide primers as listed in Table 4. Sequences were codon optimized for *E. coli* using the Integrated DNA Technologies Codon Optimization web tool. These mutants were expressed in *E. coli*, purified by NiNTA chromatography, and re-suspended in Buffer F, as described above. Each mutant enzyme contained at least one amino acid substitution. In Table 4, the site of the substitution is designated by the residue number, preceded by the original amino acid, and proceeded by the substituted amino acid. The corresponding nucleic acid codon of the substituted amino acid is shown in uppercase, while all other DNA bases are shown in lower case.

TABLE 4

| Mutant ID # | Amino acid changes | Mutant Amino Acid Sequence SEQ ID NO: | Sense Mutagenesis Oligonucleotide SEQ ID NO: | Antisense Mutagenesis Oligonucleotide SEQ ID NO: |
| --- | --- | --- | --- | --- |
| 7 | P13S | 7 | 40 | 41 |
| 23 | Q48R | 70 | 99 | 100 |
| 24 | K149T | 71 | 101 | 102 |
| 25 | D199Y | 72 | 103 | 104 |
| 26 | D199N | 73 | 105 | 106 |
| 27 | D199G | 74 | 107 | 108 |
| 28 | D199E | 75 | 109 | 110 |
| 29 | D199V | 76 | 111 | 112 |
| 30 | M80L | 77 | 113 | 114 |
| 31 | F218L | 78 | 115 | 116 |
| 32 | P13S A107V | 79 | 40, 117 | 41, 118 |
| 33 | P13S D199Y | 80 | 40, 103 | 41, 104 |
| 34 | Q48R D199N | 81 | 98, 105 | 99, 106 |
| 35 | Q48R A107V | 82 | 98, 117 | 99, 118 |
| 36 | A107V K149T | 83 | 117, 101 | 118, 102 |
| 37 | A107V D199Y | 84 | 117, 103 | 118, 104 |
| 38 | A107V D199N | 85 | 117, 105 | 118, 106 |
| 39 | A107V D199G | 86 | 117, 107 | 118, 108 |
| 40 | A107V D199E | 87 | 117, 109 | 118, 110 |

TABLE 4-continued

| Mutant ID # | Amino acid changes | Mutant Amino Acid Sequence SEQ ID NO: | Sense Mutagenesis Oligonucleotide SEQ ID NO: | Antisense Mutagenesis Oligonucleotide SEQ ID NO: |
|---|---|---|---|---|
| 41 | M80L F218L | 88 | 113, 115 | 114, 116 |
| 42 | M80L A107V F218L | 89 | 113, 117, 115 | 114, 118, 116 |
| 43 | A107V | 90 | 117 | 118 |
| 44 | G12S | 91 | 119 | 120 |
| 45 | G10S | 92 | 121 | 122 |
| 46 | E157K | 93 | 123 | 124 |
| 47 | G12S A107V | 94 | 119, 117 | 120, 118 |

The functional activity of these mutants was first characterized in a digital rhPCR system using an RNP assay. Each of the mutants was tested in a reaction that contained 420 fmol of enzyme and either blocked or unblocked RNP primers. For each 20 µl reaction volume, either 420 fmol (21 nM) of each mutant RNase H2 enzyme was added to a separate reaction mix also containing 1× ddPCR Supermix for Probes (No dUTP) (Bio-Rad Laboratories, Inc., Hercules, Calif.), 900 nM of blocked or unblocked RNP primers, 250 nM probe, and $5 \times 10^4$ copies GBLOCK® RNase P template (Integrated DNA Technologies (IDT), Coralville, Iowa). Reactions containing unblocked primers served as controls to ensure viability of the digital rhPCR system.

Figure 4:
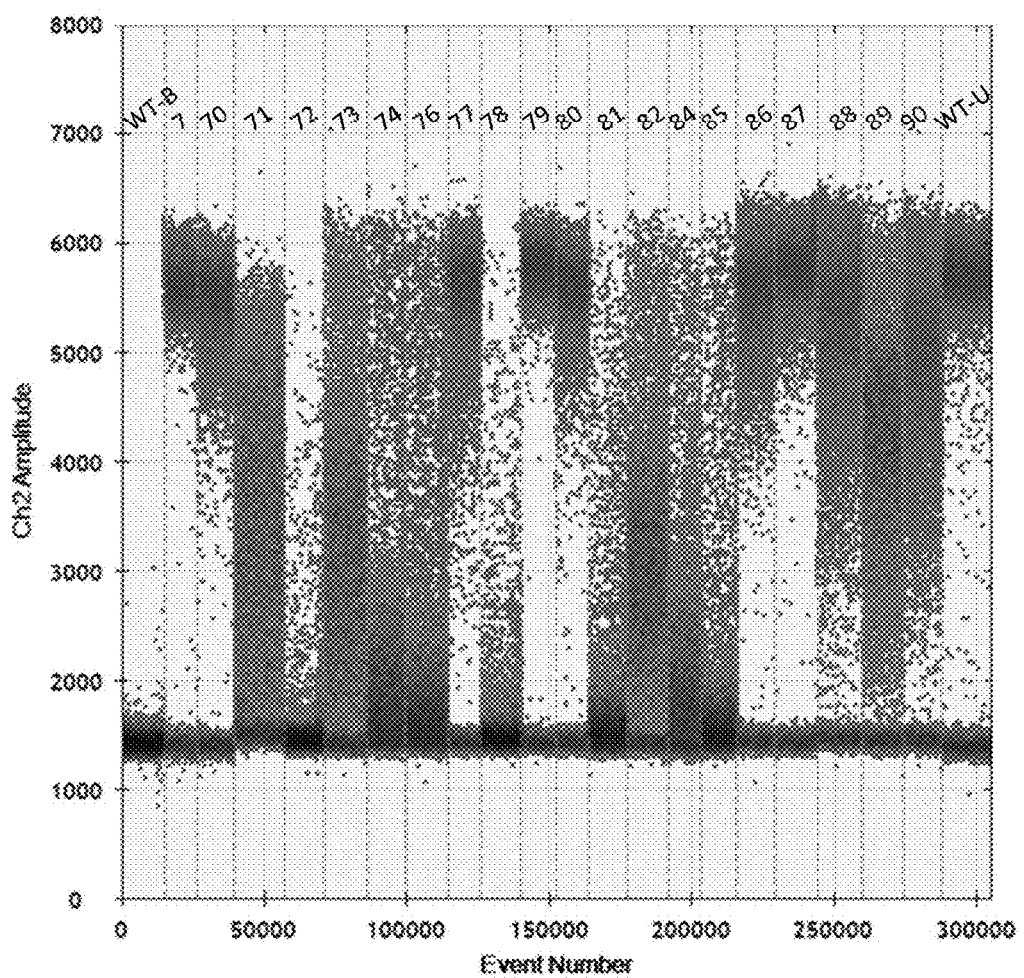
FIG. 4 compares the wild-type RNase H2 and emulsion-based evolution derived mutant RNase H2 enzymes in a digital drop PCR system using the QX200™ Droplet Reader (Bio-Rad). An RNase P (RNP) assay was run using either standard unblocked (U) primers or blocked (B) rhPrimers with 420 fmol of each mutant. The unblocked sample with the wild-type mutant is shown as a reference.

The samples were then emulsified using the Bio-Rad® Automated Droplet Generator™ (Bio-Rad® Laboratories, Inc., Hercules, Calif.) system, which generated 20,000 uniform nanoliter-sized water-in-oil droplets within each sample. The target DNA was randomly distributed among the droplets, and each droplet served to partition the reactions. The fraction of PCR-positive droplets was used to quantify the target nucleic acid according to the Poisson distribution. Digital rhPCR was then performed using the primers and probes listed in Table 1, and each of the 20,000 droplets was analyzed for an increase in fluorescence intensity on a Bio-Rad® QX-200™ Droplet Digital™ Reader. An increase in fluorescence intensity indicated a positive reaction, while no fluorescence indicated that amplification of the target nucleic acid did not occur. The fluorescence intensity was then plotted for each droplet (event number) using the QUANTASOFT™ v1.7 software (Bio-Rad® Laboratories, Inc., Hercules, Calif.). The results are shown in FIG. 4.

The activity of each mutant is listed in Table 5, and is presented relative to the activity level of wild-type P.a. RNase H2. From these experiments, the RNase H2 mutants P13S (SEQ ID NO: 7), Q48R (SEQ ID NO: 70), M80L (SEQ ID NO: 77), P13S_A107V (SEQ ID NO: 79), P13S_D199Y (SEQ ID NO: 80), A107V_D199G (SEQ ID NO: 86) and A107V_D199E (SEQ ID NO: 87) were identified as top performers.

TABLE 5

| Mutant ID # | Specific AA changes | SEQ ID NO: | U/µg | % of WT activity | 1 mU = x fmol |
|---|---|---|---|---|---|
| — | Wild-type RNase H2 | 125 | 17.3 | 100.0% | 2.1 |
| 7 | P13S | 7 | 5.2 | 30.1% | 7.0 |
| 23 | Q48R | 70 | 17.3 | 100.0% | 2.1 |
| 24 | K149T | 71 | 0.059 | 0.3% | 615.8 |
| 25 | D199Y | 72 | 17.3 | 100.0% | 2.1 |
| 26 | D199N | 73 | 26 | 150.3% | 1.4 |
| 27 | D199G | 74 | 26 | 150.3% | 1.4 |
| 28 | D199E | 75 | 17.3 | 100.0% | 2.1 |
| 29 | D199V | 76 | 20 | 115.6% | 1.8 |
| 30 | M80L | 77 | 26.2 | 151.4% | 1.4 |
| 31 | F218L | 78 | 40.4 | 233.5% | 0.9 |
| 32 | P13S A107V | 79 | 13 | 75.1% | 2.8 |
| 33 | P13S D199Y | 80 | 13 | 75.1% | 2.8 |
| 34 | Q48R D199N | 81 | 26 | 150.3% | 1.4 |
| 35 | Q48R A107V | 82 | 26 | 150.3% | 1.4 |
| 36 | A107V K149T | 83 | 0.65 | 3.8% | 55.9 |
| 37 | A107V D199Y | 84 | 26 | 150.3% | 1.4 |
| 38 | A107V D199N | 85 | 26 | 150.3% | 1.4 |
| 39 | A107V D199G | 86 | 17.3 | 100.0% | 2.1 |
| 40 | A107V D199E | 87 | 17.3 | 100.0% | 2.1 |
| 41 | M80L F218L | 88 | 13 | 75.1% | 2.8 |
| 42 | M80L A107V F218L | 89 | 20 | 115.6% | 1.8 |
| 43 | A107V | 90 | 20.00 | 115.6% | 1.8 |
| 44 | G12S | 91 | 0.15 | 0.9% | 238.9 |
| 45 | G10S | 92 | 0.22 | 1.3% | 166.3 |
| 46 | E157K | 93 | 20.00 | 115.6% | 1.8 |
| 47 | G12S A107V | 94 | 2.60 | 15.0% | 14.0 |

The results of this example confirm that P.a. RNase H2 mutant enzymes can be used in an emulsion-based digital droplet PCR assay.

Example 5

This example demonstrates the activity of wild-type RNase H2 enzymes obtained or derived from additional species in an emulsion-based digital droplet PCR assay.

Wild-type RNase H2 enzymes were synthesized and/or purified from *Pyrococcus furiosis* (SEQ ID NO: 95), *Pyrococcus horikoshii* (SEQ ID NO: 96), and the archaeal species *Thermococcus kodakarensis* (SEQ ID NO: 97) and *Thermococcus litoralis* (SEQ ID NO: 98), which have greater sequence divergence from *Pyrococcus*. A comparison of the RNase H2 amino acid sequences (see FIG. 5) revealed that both *Thermococcus* species have a native Q48R amino acid sequence and that *T. kodakarensis* has an additional native leucine amino acid at position 80 (equivalent to M80L in P.a. RNase H2).

Wild-type RNase H2 sequences for each enzyme were obtained as synthetic sequences and codon optimized for *E. coli* using the Integrated DNA Technologies (IDT) Codon Optimization web tool (www.idtdna.com/CodonOpt). The wild-type RNase H2 sequences were expressed in *E. coli*, purified by Ni-NTA affinity chromatography, and dialyzed in Buffer F (20 mM Tris-HCl pH 8.4, 100 mM KCl, 0.1 mM EDTA, 0.1% Triton X-100, and 50% glycerol) as previously described for purification of wild-type P.a. RNase H2 (see U.S. Pat. No. 8,911,948). Protein concentrations were independently verified using Bradford and bicinchoninic acid (BCA) assays, using standard protocols described by the manufacturers. The recombinant proteins were tested for RNase and DNase contamination using DNASE ALERT® and RNASE ALERT® kits (Integrated DNA Technologies, Inc., Coralville, Iowa).

To determine whether the wild-type proteins from *Pyrococcus furiosis*, *Pyrococcus horikoshii*, *Thermococcus kodakarensis*, and *Thermococcus litoralis* showed improved activity in rh-ddPCR, functionality was assessed using an RNase P assay as described above (see Table 1, SEQ ID Nos: 23-27). Reactions were carried out in 96-well plate format and contained 1×ddPCR™ Supermix (Bio-Rad Laboratories, Inc., Hercules, Calif.) for probes (no dUTP), 900 nM blocked or unblocked primers, 250 nM HEX probe, and 5×10$^4$ copies RNase P GBLOCK® template (Integrated DNA Technologies, Inc., Coralville, Iowa). RNase H2 enzymes were diluted in Buffer D and 420 fmol were added to a final volume of 20 µl. Emulsions were generated with the Bio-Rad Automated Droplet Generator™ system (Bio-Rad Laboratories, Inc., Hercules, Calif.). Droplets were analyzed using the Bio-Rad QX200™ Digital Drop Reader (Bio-Rad Laboratories, Inc., Hercules, Calif.) following PCR amplification.

Figure 6:
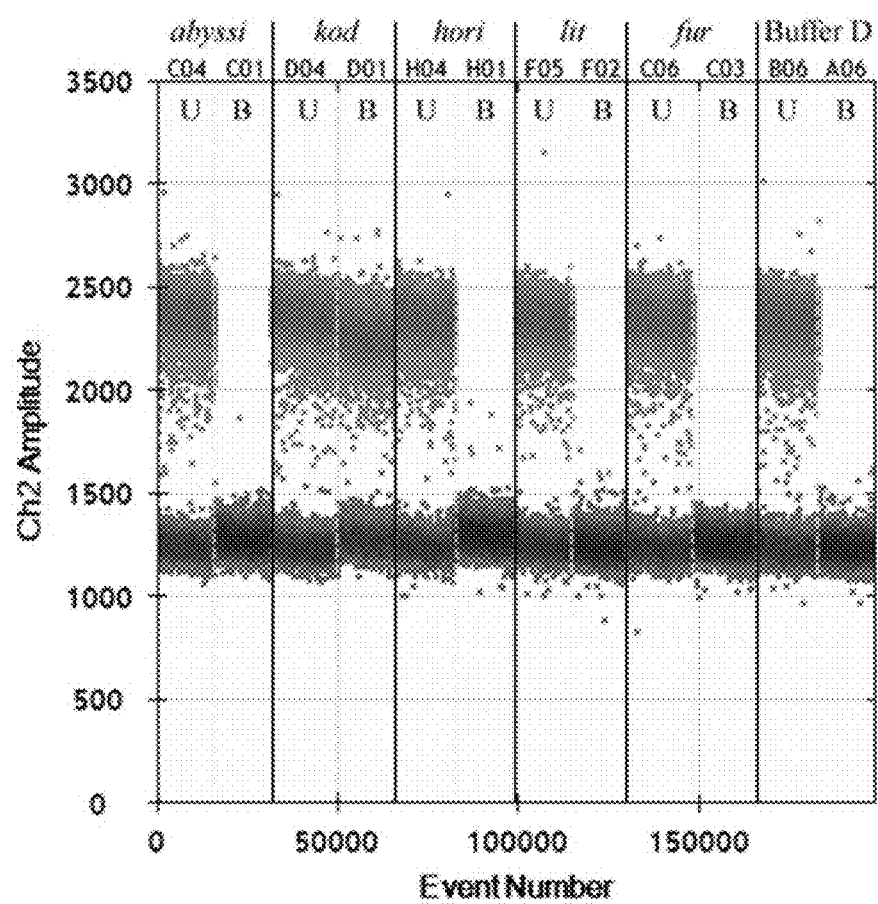
FIG. 6 is a plot from a QX-200™ DROPLET DIGITAL™ (DDPCR™) system (Bio-Rad Laboratories, Inc., Hercules, Calif.) showing a comparison of wild-type RNase H2 isolated from *P. abyssi, T. kodakarensis, P. horikoshii, T.*

As demonstrated above, the wild-type P.a. did not support amplification from the blocked primers at 420 fmol (see FIG. 6). The closely related wild-type P. fur and P. hori also did not support amplification at 420 fmol. While the wild-type T. lit did not demonstrate activity at 420 fmol, the wild-type T. kod (containing native Q48R and M80L mutations) displayed activity at 420 fmol, with a signal intensity similar to the unblocked primer control, as shown in FIG. 6.

A titration of T. kod RNase H2 from 840 fmol to 52.5 fmol (the equivalent of 400 mU to 25 mU of wild-type P.a.) was tested in rh ddPCR to further assess the enzyme activity, as shown in FIG. 7. A titration of P.a. RNase H2 from 840 fmol to 210 fmol (400 mU to 100 mU) was included. While the wild-type P.a. enzyme was inactive at 210 fmol, the wild-type T. kod enzyme supported efficient amplification with signal intensity similar to the unblocked control at the tested enzyme concentrations.

These results confirm that wild-type RNase H2 enzymes from P. fur, P. hori, and T. lit are not effective in an emulsion droplet digital PCR system, and that wild-type T. kod is effective at lowered concentrations.

Example 6

This example demonstrates the use of RNase H2 mutant enzymes derived from P. fur, P. hori, T. kod, and T. lit in an emulsion-based digital droplet PCR assay.

To determine whether the equivalents of P.a. P13S, Q48R, M80L, A107V and P13S A107V mutations improved activity in an emulsion in alternative RNase H2 enzymes, these mutations were introduced into the P. fur, P. hori, T. lit, and T. kod RNase H2 proteins by site-directed mutagenesis (see Weiner et al., *Gene*, 151:119-123 (1994)) using the primers listed in Table 6. Mutant RNase H enzyme sequences were codon optimized for expression in *E. coli* using the Integrated DNA Technologies Codon Optimization web tool (www.idtdna.com/CodonOpt). Each mutant enzyme contained at least one amino acid substitution. As shown in Table 6, each mutant was designated according to the amino acid residue number where the substitution occurred, preceded by the original amino acid, and proceeded by the substituted amino acid.

TABLE 6

| Mutant ID | Mutant Species | Amino acid change | Mutant Amino Acid Sequence SEQ ID NO: | Sense Mutagenesis Oligonucleotide SEQ ID NO: | Antisense Mutagenesis Oligonucleotide SEQ ID NO: |
|---|---|---|---|---|---|
| 48 | P. fur | P13S | 126 | 139 | 140 |
| 49 | P. fur | E48R | 127 | 141 | 142 |
| 50 | P. fur | M80L | 128 | 143 | 144 |
| 51 | P. fur | A107V | 129 | 145 | 146 |
| 52 | P. fur | P13S A107V | 130 | 139, 145 | 140, 146 |
| 53 | P. hori | Q48R | 131 | 149 | 150 |
| 54 | P. hori | M80L | 132 | 151 | 152 |
| 55 | P. hori | A107V | 133 | 153 | 154 |
| 56 | T. kod | P13S | 134 | 155 | 156 |
| 57 | T. kod | A107V | 135 | 157 | 158 |
| 58 | T. kod | P13S A107V | 136 | 155, 157 | 156, 158 |
| 59 | T. lit | M80L | 137 | 161 | 162 |
| 60 | T. lit | A107V | 138 | 163 | 164 |
| 61 | P. abs | P13S Q48R M80L A107V | 165 | 40, 99, 113, 117 | 41, 100, 114, 118 |

The RNase H mutants were expressed in *E. coli*, purified by NiNTA chromatography, and re-suspended in Buffer F (20 mM Tris-HCl pH 8.4, 100 mM KCl, 0.1 M EDTA, 0.1% Triton X-100, and 50% glycerol). Techniques for purification were identical to those previously described for purifying HIS-tagged wild-type P.a. RNase H2 (see U.S. Pat. No. 8,911,948).

Protein concentrations were independently verified using Bradford and BCA assays according to the manufacturer's instructions. Proteins were also tested for RNase and DNase contamination using DNASE ALERT® and RNASE ALERT® kits (Integrated DNA Technologies, Inc., Coralville, Iowa). Some mutant proteins exhibited low levels of RNase contamination. As a result, 5 U of SUPERASE-IN™ RNase Inhibitor (Thermo Fisher Scientific, Waltham, Mass.) was included in all rh ddPCR reactions. SUPERASE-IN™ does not inhibit RNase H2 activity and blocks background RNase activity.

For each 20 µl reaction volume, 420 fmol (21 nM) of each RNase H2 enzyme was added to a mix containing 1× ddPCR Supermix for Probes (No dUTP) (Bio-Rad Laboratories, Inc., Hercules, Calif.), 900 nM of blocked or unblocked RNP primers, 250 nM probe, 5 U of SUPERASE-IN™, and 5×10$^4$ copies GBLOCK® RNase P template (Integrated DNA Technologies (IDT), Coralville, Iowa). Reactions containing unblocked primers served as controls to ensure viability of the digital rhPCR system.

The samples were emulsified using the Bio-Rad AUTODG™ (Bio-Rad Laboratories, Inc., Hercules, Calif.) system, which generated 20,000 uniform nanoliter-sized water-in-oil droplets within each sample. The target DNA was randomly distributed among the droplets, and each droplet served to partition the reactions. The fraction of PCR-positive droplets was used to quantify the target nucleic acid according to the Poisson distribution. Digital rhPCR was then performed using the primers and probes listed in Table 1, and each of the 20,000 droplets was analyzed for an increase in fluorescence intensity on a QX-200™ DROPLET DIGITAL™ Reader (Bio-Rad Laboratories, Inc., Hercules, Calif.). An increase in fluorescence intensity indicated a positive reaction, while no fluorescence indicated that amplification of the target nucleic acid did not occur. The fluorescence intensity was then plotted for each droplet (event number) using the QUANTASOFT™ v1.7 software (Bio-Rad® Laboratories, Inc., Hercules, Calif.). Reactions with unblocked primers (U) exhibited tight bands with high fluorescent expression, indicative of successful amplification of the template DNA.

Comparisons were made with the wild-type RNase H2 for each mutant set to assess any improvement conferred by the P.a. mutations. With the exception of T. lit (see FIG. 8), enhanced activity was observed in each wild-type enzyme background. In particular, improved activity was observed in the P. fur P13S (SEQ ID NO: 126) and P13S A107V (SEQ ID NO: 130) mutants, as shown in FIG. 9. Cleavage and subsequent amplification activity was observed in the tested P. hori mutants Q48R (SEQ ID NO: 131), M80L (SEQ ID NO: 132), and A107V (SEQ ID NO: 133), with signal intensities similar to the unblocked primer controls, as shown in FIG. 10. Cleavage and subsequent amplification activity was observed in T. kod mutants P13S (SEQ ID NO: 134), A107V (SEQ ID NO: 135), and P13S A107 (SEQ ID NO: 136), with signal intensities greater than wild-type mutants, and amplification occurring with reduced amounts of enzyme input, as shown in FIG. 11.

The results of this example confirm that P. fur, P. hori, and T. kod. RNase H2 mutant enzymes can be used in an emulsion-based digital droplet PCR assay.

Example 7

This example demonstrates the use of additional P.a. mutants in an emulsion-based digital droplet PCR assay.

A P.a. P13S Q48R M80L A107V (SEQ ID NO: 165) quadruple mutant was generated to compare activity to the T. kod P13S A107V (SEQ ID NO 136) mutant described in Example 6. The P.a. quadruple mutant was created using standard site-directed mutagenesis of the P.a. P13S A107V mutant described above using the primers listed in Table 6 to introduce Q48R and M80L, for a total of four rounds of site-directed mutagenesis. The protein was purified as described above. Protein concentration was independently verified using Bradford and BCA assays, and RNase and DNase contamination was tested using DNASE ALERT® and RNASE ALERT® kits (Integrated DNA Technologies, Inc., Coralville, Iowa).

The activity of the P.a. P13S Q48R M80L A107V mutant (SEQ ID NO: 136) was tested using the rh-ddPCR RNase P assay as previously described, including 5 U of SUPERASE-IN™. A titration of the mutant enzymes from 4200 fmol to 4.2 fmol (the equivalent of 2000 mU to 2 mU of wild-type P.a.) was compared to the activity of the wild-type P.a. at 4200 and 420 fmol, as shown in FIG. 12. The P.a. P13S Q48R M80L A107V mutant (SEQ ID NO: 136) displayed activity down to 42 fmol, but no activity at 4.2 fmol.

The results of this example demonstrate that the P.a. P13S Q48R M80L A107V mutant can support cleavage in a ddPCR environment.

Example 8

This example describes a method of detecting homology directed repair (HDR) using RNase H mutants described herein.

To detect HDR events generated from a targeted endonuclease using RNase H-dependent ddPCR, a total of three rhPCR assays targeting a desired modification site utilizing rhPrimers, one specific for the desired changes, one for the sequence of the wild type sequence, and one specific for the product of a blunt insertion of the HDR template, are designed. A locus-specific reverse primer that will amplify both the wild type and edited template also is designed. In addition, an emulsion-competent RNase H2 cleavable cycling probe (CpT) is designed to serve as a control assay for the detection of both edited and non-edited DNA.

The first set of rhPrimers are designed to detect the presence of the wild type template in an emulsion reaction. These rhPrimers are designed with the cleavable moiety located one or two bases after the most common cleavage site for the targetable endonuclease (usually 3 bases before the PAM recognition domain in Cas9). The rhPrimers are cleaved by an emulsion-competent RNase H2 enzyme, such as those described herein, when they successfully bind to a wild type template, but not when they bind to an HDR or non-homologous end joining (NHEJ) edited template. This allows for easy discrimination against editing events which may occur, while still retaining specificity for the wild type template.

The second set of rhPrimers are designed to detect HDR editing events. These rhPrimers are specific for the HDR donor template and are designed, like the wild type specific primers, with the cleavable moiety located one or two bases after the start of the edited sequence, to most accurately distinguish between the HDR and wild type templates.

The third set of rhPrimers are designed to detect a blunt insertion of the HDR template. These rhPrimers are specifically designed to generate additional signal intensity from the HDR editing signal channel via recognition of sequence duplication created by the blunt insertion.

Each of the wild type or insert-specific primers are designed to possess a universal forward primer and one of two different fluorescent probe binding domains located on the 5' end of the primer. These universal domains allow for complementary probes to bind to the amplicon upon removal of the 3' blocks by the RNase H2 enzyme and amplification by the DNA polymerase. The 5' exonuclease activity of the polymerase will degrade the detection probe generating the fluorescent signal for the wild type or HDR determination.

The CpT assay is designed to detect the presence of the template whether or not the other primers amplify. This will serve to detect the presence or absence of DNA in each emulsion droplet. If template is present, the RNase H2 enzyme will cleave the probe, generating a fluorescent signal. The probe is designed so that its $T_m$ is high enough for it to bind to the template while whole, but denatures when cleaved by the emulsion-competent RNase H2 enzyme. The desired $T_m$ for this probe therefore is about 60° C. in most reaction settings.

The described primers and probes are combined in a suitable emulsion PCR mix, and emulsion droplets are made using methods known to those of skill in the art. Thermal cycling and fluorescence quantification is then performed, allowing for template amplification and RNase H2 cleavage. In the reaction mix during amplification, the cycling probe binds to each template in the reaction, allowing for the separation of the droplets that contain templates from the droplets that do not. The droplets that contain template will allow for cleavage of the cycling probe, and generation of fluorescent signal. While this is occurring, wild type or target-specific rhPrimers bind to the template present in each individual emulsion droplet. The rhPrimers are then cleaved by the RNase H2 enzyme, which is present in the droplet as well. The DNA polymerase extends from the newly unblocked primers, incorporating the 5' universal forward primer and probe binding domains into the newly generated amplicons. The universal forward primers will then bind to their complementary binding domains, and degrade the detection probes. This will provide a fluorescent signal corresponding to either the wild type or the desired HDR template, depending on which is present in the droplet. If a blunt insertion of the HDR template occurs by the NHEJ machinery, additional fluorescence intensity will distinguish this event from a correct HDR insertion. This signal will be combined with the fluorescence obtained from the cycling probe to generate the final signal intensity. Finally, if an NHEJ event occurs rather than the desired HDR event, then only the cycling probe will bind, and be cleaved. Using this technique, desired HDR events can be separated from NHEJ events and HDR template blunt insertion in a single reaction.

All references, including publications, patent applications, and patents, cited herein, are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. The present disclosure also contemplates other embodiments "comprising," "consisting of," and "consisting essentially of," the embodiments or elements presented herein, whether explicitly set forth or not. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for performing an RNase H2-mediated cleavage of one or more nucleic acid sequences of interest, the method comprising:
   (a) providing a sample comprising one or more nucleic acid sequences of interest;
   (b) providing an RNase H2 enzyme selected from:
      (i) a mutant *Pyrococcus abyssi* (P.a) RNase H2 enzyme consisting of an amino acid sequence selected from SEQ ID NO: 1, SEQ ID NO: 2, SEQ ID NO:7, SEQ ID NO:8, SEQ ID NO:13, SEQ ID NO:15, SEQ ID NO: 16, SEQ ID NO:17, SEQ ID NO:18, SEQ ID NO:20, SEQ ID NO: 70, SEQ ID NO: 71, SEQ ID NO: 73, SEQ ID NO: 74, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 90, and SEQ ID NO: 165;
      (ii) a mutant *Pyrococcus furiosis* (P. fur) RNase H2 enzyme consisting of an amino acid sequence selected from SEQ ID NO: 126, SEQ ID NO: 127, SEQ ID NO: 128, SEQ ID NO: 129, and SEQ ID NO: 130;
      (iii) a mutant *Pyrococcus horikoshii* (P. hon) RNase H2 enzyme consisting of an amino acid sequence selected from SEQ ID NO: 131, SEQ ID NO: 132, and SEQ ID NO: 133;
      (iv) a mutant *Thermococcus kodakarensis* (T. kod) RNase H2 enzyme consisting of an amino acid sequence selected from SEQ ID NO: 134, SEQ ID NO: 135, and SEQ ID NO:136; or
      (v) a mutant *Thermococcus litoralis* (T. lit) RNase H2 enzyme consisting of the amino acid sequence of SEQ ID NO: 137 or SEQ ID NO: 138; and
   (c) performing RNase H2-mediated cleavage reaction on the one or more nucleic acid sequences of interest whereupon the one or more nucleic acid sequences of interest are cleaved.

2. The method of claim 1, wherein the RNase H2-mediated cleavage reaction is performed as part of an RNase H-dependent PCR (rhPCR) reaction, a loop-mediated isothermal amplification (LAMP) reaction, or cycling probe technology (CPT).

3. The method of claim 1, wherein the RNase H2-mediated cleavage reaction is performed as part of an RNase H-dependent PCR (rhPCR) reaction in a digital PCR system.

4. The method of claim 3, wherein the digital PCR system is an emulsion droplet digital PCR (ddPCR) system.

5. The method of claim 1, wherein the RNase H2 enzyme is a mutant *Pyrococcus abyssi* (P.a) RNase H2 enzyme consisting of an amino acid sequence selected from SEQ ID NO: 1, SEQ ID NO: 2, SEQ ID NO:7, SEQ ID NO:8, SEQ ID NO:13, SEQ ID NO:15, SEQ ID NO: 16, SEQ ID NO:17, SEQ ID NO:18, SEQ ID NO:20, SEQ ID NO: 70, SEQ ID NO: 71, SEQ ID NO: 73, SEQ ID NO: 74, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 84, SEQ ID NO: 85, SEQ ID NO: 86, SEQ ID NO: 87, SEQ ID NO: 88, SEQ ID NO: 89, SEQ ID NO: 90, and SEQ ID NO: 165.

6. The method of claim 1, wherein the sample comprises one or more nucleic acid sequences of interest obtained from one or more cells.

7. The method of claim 6, wherein the one or more cells are animal cells.

8. The method of claim 7, wherein the one or more cells are mammalian cells.

9. The method of claim 6, wherein the one or more cells are obtained from a subject.

10. The method of claim 6, wherein the one or more cells are obtained from an in vitro culture.

11. The method of claim 1, wherein the sample comprises one or more nucleic, acid sequences of interest obtained from one or more of blood, plasma, serum, cerebrospinal fluid, semen, urine, or amniotic fluid.

12. The method of claim 1, wherein the one or more nucleic acids are synthetically generated.

13. A method of performing an RNase H2-mediated cleavage of one or more nucleic acid sequences of interest comprising:
   (a) providing a sample comprising one or more nucleic acid sequences of interest;
   (b) providing a *Thermococcus kodakarensis* (T. kod) RNase H2 enzyme consisting of the amino acid sequence of SEQ ID NO: 97; and
   (c) performing an RNase H2-mediated cleavage reaction on the one or more nucleic acid sequences of interest, whereupon the one or more nucleic acid sequences of interest are cleaved.

\* \* \* \* \*

SEQUENCE LISTING

```
<160> NUMBER OF SEQ ID NOS: 165

<210> SEQ ID NO 1
<211> LENGTH: 224
<212> TYPE: PRT
<213> ORGANISM: Artificial sequence
<220> FEATURE:
<223> OTHER INFORMATION: Synthetic
```

<400> SEQUENCE: 1

Met Lys Val Ala Gly Ala Asp Glu Ser Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 2
<211> LENGTH: 224
<212> TYPE: PRT
<213> ORGANISM: Artificial sequence
<220> FEATURE:
<223> OTHER INFORMATION: Synthetic

<400> SEQUENCE: 2

Met Lys Val Ala Gly Ala Asp Glu Ala Gly Lys Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

```
Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220
```

<210> SEQ ID NO 3
<211> LENGTH: 224
<212> TYPE: PRT
<213> ORGANISM: Artificial sequence
<220> FEATURE:
<223> OTHER INFORMATION: Synthetic

<400> SEQUENCE: 3

```
Met Lys Val Ala Gly Ala Asp Glu Ala Gly Gln Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
                100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220
```

<210> SEQ ID NO 4
<211> LENGTH: 224
<212> TYPE: PRT
<213> ORGANISM: Artificial sequence
<220> FEATURE:
<223> OTHER INFORMATION: Synthetic

<400> SEQUENCE: 4

```
Met Lys Val Ala Gly Ala Asp Glu Ala Gly Arg Ala Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220
```

<210> SEQ ID NO 5
<211> LENGTH: 224
<212> TYPE: PRT
<213> ORGANISM: Artificial sequence
<220> FEATURE:
<223> OTHER INFORMATION: Synthetic

<400> SEQUENCE: 5

```
Met Lys Val Ala Gly Ala Asp Glu Ala Gly Arg Thr Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140
```

```
Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
        210                 215                 220
```

<210> SEQ ID NO 6
<211> LENGTH: 224
<212> TYPE: PRT
<213> ORGANISM: Artificial sequence
<220> FEATURE:
<223> OTHER INFORMATION: Synthetic

<400> SEQUENCE: 6

```
Met Lys Val Ala Gly Ala Asp Glu Ala Gly Arg Cys Pro Val Ile Gly
1               5                   10                  15

Pro Leu Val Ile Val Ala Ala Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
        210                 215                 220
```

<210> SEQ ID NO 7
<211> LENGTH: 224
<212> TYPE: PRT
<213> ORGANISM: Artificial sequence
<220> FEATURE:
<223> OTHER INFORMATION: Synthetic

<400> SEQUENCE: 7

Met Lys Val Ala Gly Ala Asp Glu Ala Gly Arg Gly Ser Val Ile Gly

```
  1               5                  10                 15
Pro Leu Val Ile Val Ala Ala Val Val Glu Glu Asp Lys Ile Arg Ser
            20                 25                 30
Leu Thr Lys Leu Gly Val Lys Asp Ser Lys Gln Leu Thr Pro Ala Gln
            35                 40                 45
Arg Glu Lys Leu Phe Asp Glu Ile Val Lys Val Leu Asp Asp Tyr Ser
     50                 55                 60
Val Val Ile Val Ser Pro Gln Asp Ile Asp Gly Arg Lys Gly Ser Met
 65                 70                 75                 80
Asn Glu Leu Glu Val Glu Asn Phe Val Lys Ala Leu Asn Ser Leu Lys
                85                 90                 95
Val Lys Pro Glu Val Ile Tyr Ile Asp Ser Ala Asp Val Lys Ala Glu
            100                105                110
Arg Phe Ala Glu Asn Ile Arg Ser Arg Leu Ala Tyr Glu Ala Lys Val
            115                120                125
Val Ala Glu His Lys Ala Asp Ala Lys Tyr Glu Ile Val Ser Ala Ala
            130                135                140
Ser Ile Leu Ala Lys Val Ile Arg Asp Arg Glu Ile Glu Lys Leu Lys
145                150                155                160
Ala Glu Tyr Gly Asp Phe Gly Ser Gly Tyr Pro Ser Asp Pro Arg Thr
                165                170                175
Lys Lys Trp Leu Glu Glu Trp Tyr Ser Lys His Gly Asn Phe Pro Pro
            180                185                190
Ile Val Arg Arg Thr Trp Asp Thr Ala Lys Lys Ile Glu Glu Lys Phe
            195                200                205
Lys Arg Ala Gln Leu Thr Leu Asp Asn Phe Leu Lys Arg Phe Arg Asn
     210                215                220

<210> SEQ ID NO 8
<211> LENGTH: 224
<212> TYPE: PRT
<213> ORGANISM: Artificial sequence
<220> FEATURE:
<223> OTHER INFORMATION: Synthetic

<400> SEQUENCE: 8

Met Lys Val Ala Gly Ala Asp Glu Ala Gly Arg Gly Thr Val Ile Gly
 1               5                  10                 15
Pro Leu Val Ile Val Ala Ala Val Val Glu Glu Asp Lys Ile Arg Ser
            20                 25                 30
Leu Thr Lys Leu Gly Val Lys Asp Ser Lys Gln Leu Thr Pro Ala Gln
            35                 40                 45
Arg Glu Lys Leu Phe Asp Glu Ile Val Lys Val Leu Asp Asp Tyr Ser
     50                 55                 60
Val Val Ile Val Ser Pro Gln Asp Ile Asp Gly Arg Lys Gly Ser Met
 65                 70                 75                 80
Asn Glu Leu Glu Val Glu Asn Phe Val Lys Ala Leu Asn Ser Leu Lys
                85                 90                 95
Val Lys Pro Glu Val Ile Tyr Ile Asp Ser Ala Asp Val Lys Ala Glu
            100                105                110
Arg Phe Ala Glu Asn Ile Arg Ser Arg Leu Ala Tyr Glu Ala Lys Val
            115                120                125
Val Ala Glu His Lys Ala Asp Ala Lys Tyr Glu Ile Val Ser Ala Ala
            130                135                140
Ser Ile Leu Ala Lys Val Ile Arg Asp Arg Glu Ile Glu Lys Leu Lys
```

```
                145                 150                 155                 160
Ala Glu Tyr Gly Asp Phe Gly Ser Gly Tyr Pro Ser Asp Pro Arg Thr
                    165                 170                 175

Lys Lys Trp Leu Glu Glu Trp Tyr Ser Lys His Gly Asn Phe Pro Pro
                180                 185                 190

Ile Val Arg Arg Thr Trp Asp Thr Ala Lys Lys Ile Glu Glu Lys Phe
                    195                 200                 205

Lys Arg Ala Gln Leu Thr Leu Asp Asn Phe Leu Lys Arg Phe Arg Asn
            210                 215                 220
```

<210> SEQ ID NO 9
<211> LENGTH: 224
<212> TYPE: PRT
<213> ORGANISM: Artificial sequence
<220> FEATURE:
<223> OTHER INFORMATION: Synthetic

<400> SEQUENCE: 9

```
Met Lys Val Ala Gly Ala Asp Glu Ala Gly Arg Gly Glu Val Ile Gly
1               5                   10                  15

Pro Leu Val Ile Val Ala Ala Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
                100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                    165                 170                 175

Lys Lys Trp Leu Glu Glu Trp Tyr Ser Lys His Gly Asn Phe Pro Pro
                180                 185                 190

Ile Val Arg Arg Thr Trp Asp Thr Ala Lys Lys Ile Glu Glu Lys Phe
                    195                 200                 205

Lys Arg Ala Gln Leu Thr Leu Asp Asn Phe Leu Lys Arg Phe Arg Asn
            210                 215                 220
```

<210> SEQ ID NO 10
<211> LENGTH: 224
<212> TYPE: PRT
<213> ORGANISM: Artificial sequence
<220> FEATURE:
<223> OTHER INFORMATION: Synthetic

<400> SEQUENCE: 10

```
Met Lys Val Ala Gly Ala Asp Glu Ala Gly Arg Gly Pro Leu Ile Gly
1               5                   10                  15
```

-continued

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 11
<211> LENGTH: 224
<212> TYPE: PRT
<213> ORGANISM: Artificial sequence
<220> FEATURE:
<223> OTHER INFORMATION: Synthetic

<400> SEQUENCE: 11

Met Lys Val Ala Gly Ala Asp Glu Ala Gly Arg Gly Pro Phe Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

```
Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
    210                 215                 220

<210> SEQ ID NO 12
<211> LENGTH: 224
<212> TYPE: PRT
<213> ORGANISM: Artificial sequence
<220> FEATURE:
<223> OTHER INFORMATION: Synthetic

<400> SEQUENCE: 12

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Ala Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
    210                 215                 220

<210> SEQ ID NO 13
<211> LENGTH: 224
<212> TYPE: PRT
<213> ORGANISM: Artificial sequence
<220> FEATURE:
<223> OTHER INFORMATION: Synthetic

<400> SEQUENCE: 13

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30
```

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Gly Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
            210                 215                 220

<210> SEQ ID NO 14
<211> LENGTH: 224
<212> TYPE: PRT
<213> ORGANISM: Artificial sequence
<220> FEATURE:
<223> OTHER INFORMATION: Synthetic

<400> SEQUENCE: 14

Met Lys Val Ala Gly Ala Asp Glu Ala Gly Arg Gly Pro Val Ile Gly
 1               5                  10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Thr Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
            210                 215                 220

<210> SEQ ID NO 15
<211> LENGTH: 224
<212> TYPE: PRT
<213> ORGANISM: Artificial sequence
<220> FEATURE:
<223> OTHER INFORMATION: Synthetic

<400> SEQUENCE: 15

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Gly Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
            210                 215                 220

<210> SEQ ID NO 16
<211> LENGTH: 224
<212> TYPE: PRT
<213> ORGANISM: Artificial sequence
<220> FEATURE:
<223> OTHER INFORMATION: Synthetic

<400> SEQUENCE: 16

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln

Arg Glu Lys Leu Phe Asp Glu Ile Val Lys Val Leu Asp Asp Tyr Ser
         50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ile Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Ile Glu Glu Lys Phe
            195                 200                 205

Lys Arg Ala Gln Leu Thr Leu Asp Asn Phe Leu Lys Arg Phe Arg Asn
210                 215                 220

<210> SEQ ID NO 17
<211> LENGTH: 224
<212> TYPE: PRT
<213> ORGANISM: Artificial sequence
<220> FEATURE:
<223> OTHER INFORMATION: Synthetic

<400> SEQUENCE: 17

Met Lys Val Ala Gly Ala Asp Glu Ala Gly Arg Gly Pro Val Ile Gly
 1               5                  10                  15

Pro Leu Val Ile Val Ala Ala Val Val Glu Glu Asp Lys Ile Arg Ser
                 20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
         50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro His Asp Pro Arg Thr
                165                 170                 175

Lys Lys Trp Leu Glu Glu Trp Tyr Ser Lys His Gly Asn Phe Pro Pro 180                 185                 190
Ile Val Arg Arg Thr Trp Asp Thr Ala Lys Lys Ile Glu Glu Lys Phe
                195                 200                 205

Lys Arg Ala Gln Leu Thr Leu Asp Asn Phe Leu Lys Arg Phe Arg Asn
            210                 215                 220

<210> SEQ ID NO 18
<211> LENGTH: 224
<212> TYPE: PRT
<213> ORGANISM: Artificial sequence
<220> FEATURE:
<223> OTHER INFORMATION: Synthetic

<400> SEQUENCE: 18

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
                100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 19
<211> LENGTH: 224
<212> TYPE: PRT
<213> ORGANISM: Artificial sequence
<220> FEATURE:
<223> OTHER INFORMATION: Synthetic

<400> SEQUENCE: 19

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

```
Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
             100                 105                 110

Arg Phe Ala Glu Asn Ile Arg Ser Arg Leu Ala Tyr Glu Ala Lys Val
             115                 120                 125

Val Ala Glu His Lys Ala Asp Ala Lys Tyr Glu Ile Val Ser Ala Ala
         130                 135                 140

Ser Ile Leu Ala Arg Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                 165                 170                 175

Lys Lys Trp Leu Glu Glu Trp Tyr Ser Lys His Gly Asn Phe Pro Pro
             180                 185                 190

Ile Val Arg Arg Thr Trp Asp Thr Ala Lys Lys Ile Glu Glu Lys Phe
             195                 200                 205

Lys Arg Ala Gln Leu Thr Leu Asp Asn Phe Leu Lys Arg Phe Arg Asn
             210                 215                 220

<210> SEQ ID NO 20
<211> LENGTH: 224
<212> TYPE: PRT
<213> ORGANISM: Artificial sequence
<220> FEATURE:
<223> OTHER INFORMATION: Synthetic

<400> SEQUENCE: 20

Met Lys Val Ala Gly Ala Asp Glu Ala Gly Lys Gly Pro Val Ile Gly
  1               5                  10                  15

Pro Leu Val Ile Val Ala Ala Val Val Glu Glu Asp Lys Ile Arg Ser
                 20                  25                  30

Leu Thr Lys Leu Gly Val Lys Asp Ser Lys Gln Leu Thr Pro Ala Gln
             35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
             100                 105                 110

Arg Phe Ala Glu Asn Ile Arg Ser Arg Leu Ala Tyr Glu Ala Lys Val
             115                 120                 125

Val Ala Glu His Lys Ala Asp Ala Lys Tyr Glu Ile Val Ser Ala Ala
         130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                 165                 170                 175

Lys Lys Trp Leu Glu Glu Trp Tyr Ser Lys His Gly Asn Phe Pro Pro
             180                 185                 190
```

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
    210                 215                 220

<210> SEQ ID NO 21
<211> LENGTH: 224
<212> TYPE: PRT
<213> ORGANISM: Artificial sequence
<220> FEATURE:
<223> OTHER INFORMATION: Synthetic

<400> SEQUENCE: 21

Met Lys Val Ala Gly Ala Asp Glu Ala Gly Ala Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Gly Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 22
<211> LENGTH: 224
<212> TYPE: PRT
<213> ORGANISM: Artificial sequence
<220> FEATURE:
<223> OTHER INFORMATION: Synthetic

<400> SEQUENCE: 22

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

```
Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Gln Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
210                 215                 220
```

<210> SEQ ID NO 23
<211> LENGTH: 19
<212> TYPE: DNA
<213> ORGANISM: Artificial sequence
<220> FEATURE:
<223> OTHER INFORMATION: Synthetic

<400> SEQUENCE: 23
gcggagggaa gctcatcag                                          19

<210> SEQ ID NO 24
<211> LENGTH: 22
<212> TYPE: DNA
<213> ORGANISM: Artificial sequence
<220> FEATURE:
<223> OTHER INFORMATION: Synthetic

<400> SEQUENCE: 24
ccctagtctc agaccttccc aa                                      22

<210> SEQ ID NO 25
<211> LENGTH: 24
<212> TYPE: DNA
<213> ORGANISM: Artificial sequence
<220> FEATURE:
<223> OTHER INFORMATION: Synthetic

<400> SEQUENCE: 25
ccacgagctg agtgcgtcct gtca                                    24

<210> SEQ ID NO 26
<211> LENGTH: 25
<212> TYPE: DNA
<213> ORGANISM: Artificial sequence
<220> FEATURE:
<223> OTHER INFORMATION: Synthetic

<400> SEQUENCE: 26
gcggagggaa gctcatcagu ggggg                                   25

<210> SEQ ID NO 27
<211> LENGTH: 28
<212> TYPE: DNA
<213> ORGANISM: Artificial sequence
<220> FEATURE:
<223> OTHER INFORMATION: Synthetic

<400> SEQUENCE: 27
ccctagtctc agaccttccc aagggaca                              28

<210> SEQ ID NO 28
<211> LENGTH: 52
<212> TYPE: DNA
<213> ORGANISM: Artificial sequence
<220> FEATURE:
<223> OTHER INFORMATION: Synthetic

<400> SEQUENCE: 28
atgaaagttg caggtgcaga tgaatccggt cgtggtccag ttattggtcc gc    52

<210> SEQ ID NO 29
<211> LENGTH: 52
<212> TYPE: DNA
<213> ORGANISM: Artificial sequence
<220> FEATURE:
<223> OTHER INFORMATION: Synthetic

<400> SEQUENCE: 29
gcggaccaat aactggacca cgaccggatt catctgcacc tgcaactttc at    52

<210> SEQ ID NO 30
<211> LENGTH: 53
<212> TYPE: DNA
<213> ORGANISM: Artificial sequence
<220> FEATURE:
<223> OTHER INFORMATION: Synthetic

<400> SEQUENCE: 30
agttgcaggt gcagatgaag ctggtaaggg tccagttatt ggtccgctgg tta   53

<210> SEQ ID NO 31
<211> LENGTH: 53
<212> TYPE: DNA
<213> ORGANISM: Artificial sequence
<220> FEATURE:
<223> OTHER INFORMATION: Synthetic

<400> SEQUENCE: 31
taaccagcgg accaataact ggaccettac cagcttcatc tgcacctgca act   53

<210> SEQ ID NO 32
<211> LENGTH: 53
<212> TYPE: DNA
<213> ORGANISM: Artificial sequence
<220> FEATURE:
<223> OTHER INFORMATION: Synthetic

<400> SEQUENCE: 32
agttgcaggt gcagatgaag ctggtcaggg tccagttatt ggtccgctgg tta   53

<210> SEQ ID NO 33
<211> LENGTH: 53
<212> TYPE: DNA
<213> ORGANISM: Artificial sequence
<220> FEATURE:
<223> OTHER INFORMATION: Synthetic

```
<400> SEQUENCE: 33
taaccagcgg accaataact ggaccctgac cagcttcatc tgcacctgca act          53

<210> SEQ ID NO 34
<211> LENGTH: 53
<212> TYPE: DNA
<213> ORGANISM: Artificial sequence
<220> FEATURE:
<223> OTHER INFORMATION: Synthetic

<400> SEQUENCE: 34
tgcaggtgca gatgaagctg gtcgtgcccc agttattggt ccgctggtta ttg          53

<210> SEQ ID NO 35
<211> LENGTH: 53
<212> TYPE: DNA
<213> ORGANISM: Artificial sequence
<220> FEATURE:
<223> OTHER INFORMATION: Synthetic

<400> SEQUENCE: 35
caataaccag cggaccaata actggggcac gaccagcttc atctgcacct gca          53

<210> SEQ ID NO 36
<211> LENGTH: 53
<212> TYPE: DNA
<213> ORGANISM: Artificial sequence
<220> FEATURE:
<223> OTHER INFORMATION: Synthetic

<400> SEQUENCE: 36
tgcaggtgca gatgaagctg gtcgtacacc agttattggt ccgctggtta ttg          53

<210> SEQ ID NO 37
<211> LENGTH: 53
<212> TYPE: DNA
<213> ORGANISM: Artificial sequence
<220> FEATURE:
<223> OTHER INFORMATION: Synthetic

<400> SEQUENCE: 37
caataaccag cggaccaata actggtgtac gaccagcttc atctgcacct gca          53

<210> SEQ ID NO 38
<211> LENGTH: 53
<212> TYPE: DNA
<213> ORGANISM: Artificial sequence
<220> FEATURE:
<223> OTHER INFORMATION: Synthetic

<400> SEQUENCE: 38
tgcaggtgca gatgaagctg gtcgttgtcc agttattggt ccgctggtta ttg          53

<210> SEQ ID NO 39
<211> LENGTH: 53
<212> TYPE: DNA
<213> ORGANISM: Artificial sequence
<220> FEATURE:
<223> OTHER INFORMATION: Synthetic

<400> SEQUENCE: 39
caataaccag cggaccaata actggacaac gaccagcttc atctgcacct gca          53

<210> SEQ ID NO 40
```

<210> SEQ ID NO 40
<211> LENGTH: 53
<212> TYPE: DNA
<213> ORGANISM: Artificial sequence
<220> FEATURE:
<223> OTHER INFORMATION: Synthetic

<400> SEQUENCE: 40
aggtgcagat gaagctggtc gtggttcagt tattggtccg ctggttattg ttg    53

<210> SEQ ID NO 41
<211> LENGTH: 53
<212> TYPE: DNA
<213> ORGANISM: Artificial sequence
<220> FEATURE:
<223> OTHER INFORMATION: Synthetic

<400> SEQUENCE: 41
caacaataac cagcggacca ataactgaac cacgaccagc ttcatctgca cct    53

<210> SEQ ID NO 42
<211> LENGTH: 53
<212> TYPE: DNA
<213> ORGANISM: Artificial sequence
<220> FEATURE:
<223> OTHER INFORMATION: Synthetic

<400> SEQUENCE: 42
aggtgcagat gaagctggtc gtggtacggt tattggtccg ctggttattg ttg    53

<210> SEQ ID NO 43
<211> LENGTH: 53
<212> TYPE: DNA
<213> ORGANISM: Artificial sequence
<220> FEATURE:
<223> OTHER INFORMATION: Synthetic

<400> SEQUENCE: 43
caacaataac cagcggacca ataaccgtac cacgaccagc ttcatctgca cct    53

<210> SEQ ID NO 44
<211> LENGTH: 53
<212> TYPE: DNA
<213> ORGANISM: Artificial sequence
<220> FEATURE:
<223> OTHER INFORMATION: Synthetic

<400> SEQUENCE: 44
aggtgcagat gaagctggtc gtggtgaagt tattggtccg ctggttattg ttg    53

<210> SEQ ID NO 45
<211> LENGTH: 53
<212> TYPE: DNA
<213> ORGANISM: Artificial sequence
<220> FEATURE:
<223> OTHER INFORMATION: Synthetic

<400> SEQUENCE: 45
caacaataac cagcggacca ataacttcac cacgaccagc ttcatctgca cct    53

<210> SEQ ID NO 46
<211> LENGTH: 53
<212> TYPE: DNA
<213> ORGANISM: Artificial sequence
<220> FEATURE:
<223> OTHER INFORMATION: Synthetic

<400> SEQUENCE: 46
tgcagatgaa gctggtcgtg gtccactcat tggtccgctg gttattgttg ctg             53

<210> SEQ ID NO 47
<211> LENGTH: 53
<212> TYPE: DNA
<213> ORGANISM: Artificial sequence
<220> FEATURE:
<223> OTHER INFORMATION: Synthetic

<400> SEQUENCE: 47
cagcaacaat aaccagcgga ccaatgagtg gaccacgacc agcttcatct gca             53

<210> SEQ ID NO 48
<211> LENGTH: 53
<212> TYPE: DNA
<213> ORGANISM: Artificial sequence
<220> FEATURE:
<223> OTHER INFORMATION: Synthetic

<400> SEQUENCE: 48
tgcagatgaa gctggtcgtg gtccatttat tggtccgctg gttattgttg ctg             53

<210> SEQ ID NO 49
<211> LENGTH: 53
<212> TYPE: DNA
<213> ORGANISM: Artificial sequence
<220> FEATURE:
<223> OTHER INFORMATION: Synthetic

<400> SEQUENCE: 49
cagcaacaat aaccagcgga ccaataaatg gaccacgacc agcttcatct gca             53

<210> SEQ ID NO 50
<211> LENGTH: 53
<212> TYPE: DNA
<213> ORGANISM: Artificial sequence
<220> FEATURE:
<223> OTHER INFORMATION: Synthetic

<400> SEQUENCE: 50
agccgaatac ggtgattttg gttccgcata cccgtctgat ccgcgtacta aga             53

<210> SEQ ID NO 51
<211> LENGTH: 53
<212> TYPE: DNA
<213> ORGANISM: Artificial sequence
<220> FEATURE:
<223> OTHER INFORMATION: Synthetic

<400> SEQUENCE: 51
tcttagtacg cggatcagac gggtatgcgg aaccaaaatc accgtattcg gct             53

<210> SEQ ID NO 52
<211> LENGTH: 53
<212> TYPE: DNA
<213> ORGANISM: Artificial sequence
<220> FEATURE:
<223> OTHER INFORMATION: Synthetic

<400> SEQUENCE: 52
atacggtgat tttggttccg gttacgggtc tgatccgcgt actaagaaat ggc             53

<210> SEQ ID NO 53
<211> LENGTH: 53
<212> TYPE: DNA

```
<213> ORGANISM: Artificial sequence
<220> FEATURE:
<223> OTHER INFORMATION: Synthetic

<400> SEQUENCE: 53
gccatttctt agtacgcgga tcagacccgt aaccggaacc aaaatcaccg tat          53

<210> SEQ ID NO 54
<211> LENGTH: 53
<212> TYPE: DNA
<213> ORGANISM: Artificial sequence
<220> FEATURE:
<223> OTHER INFORMATION: Synthetic

<400> SEQUENCE: 54
cggtgatttt ggttccggtt acccgaccga tccgcgtact aagaaatggc tgg          53

<210> SEQ ID NO 55
<211> LENGTH: 53
<212> TYPE: DNA
<213> ORGANISM: Artificial sequence
<220> FEATURE:
<223> OTHER INFORMATION: Synthetic

<400> SEQUENCE: 55
ccagccattt cttagtacgc ggatcggtcg ggtaaccgga accaaaatca ccg          53

<210> SEQ ID NO 56
<211> LENGTH: 53
<212> TYPE: DNA
<213> ORGANISM: Artificial sequence
<220> FEATURE:
<223> OTHER INFORMATION: Synthetic

<400> SEQUENCE: 56
cggtgatttt ggttccggtt acccgggaga tccgcgtact aagaaatggc tgg          53

<210> SEQ ID NO 57
<211> LENGTH: 53
<212> TYPE: DNA
<213> ORGANISM: Artificial sequence
<220> FEATURE:
<223> OTHER INFORMATION: Synthetic

<400> SEQUENCE: 57
ccagccattt cttagtacgc ggatctcccg ggtaaccgga accaaaatca ccg          53

<210> SEQ ID NO 58
<211> LENGTH: 53
<212> TYPE: DNA
<213> ORGANISM: Artificial sequence
<220> FEATURE:
<223> OTHER INFORMATION: Synthetic

<400> SEQUENCE: 58
cggtgatttt ggttccggtt acccgattga tccgcgtact aagaaatggc tgg          53

<210> SEQ ID NO 59
<211> LENGTH: 53
<212> TYPE: DNA
<213> ORGANISM: Artificial sequence
<220> FEATURE:
<223> OTHER INFORMATION: Synthetic

<400> SEQUENCE: 59
ccagccattt cttagtacgc ggatcaatcg ggtaaccgga accaaaatca ccg          53
```

<210> SEQ ID NO 60
<211> LENGTH: 53
<212> TYPE: DNA
<213> ORGANISM: Artificial sequence
<220> FEATURE:
<223> OTHER INFORMATION: Synthetic

<400> SEQUENCE: 60
cggtgatttt ggttccggtt acccgcatga tccgcgtact aagaaatggc tgg       53

<210> SEQ ID NO 61
<211> LENGTH: 53
<212> TYPE: DNA
<213> ORGANISM: Artificial sequence
<220> FEATURE:
<223> OTHER INFORMATION: Synthetic

<400> SEQUENCE: 61
ccagccattt cttagtacgc ggatcatgcg ggtaaccgga accaaaatca ccg       53

<210> SEQ ID NO 62
<211> LENGTH: 53
<212> TYPE: DNA
<213> ORGANISM: Artificial sequence
<220> FEATURE:
<223> OTHER INFORMATION: Synthetic

<400> SEQUENCE: 62
tgattttggt tccggttacc cgtctgagcc gcgtactaag aaatggctgg aag       53

<210> SEQ ID NO 63
<211> LENGTH: 53
<212> TYPE: DNA
<213> ORGANISM: Artificial sequence
<220> FEATURE:
<223> OTHER INFORMATION: Synthetic

<400> SEQUENCE: 63
cttccagcca tttcttagta cgcggctcag acgggtaacc ggaaccaaaa tca       53

<210> SEQ ID NO 64
<211> LENGTH: 53
<212> TYPE: DNA
<213> ORGANISM: Artificial sequence
<220> FEATURE:
<223> OTHER INFORMATION: Synthetic

<400> SEQUENCE: 64
cgtatccgca gcctctatcc tggcacgcgt tatccgtgac cgcgagatcg aaa       53

<210> SEQ ID NO 65
<211> LENGTH: 53
<212> TYPE: DNA
<213> ORGANISM: Artificial sequence
<220> FEATURE:
<223> OTHER INFORMATION: Synthetic

<400> SEQUENCE: 65
tttcgatctc gcggtcacgg ataacgcgtg ccaggataga ggctgcggat acg       53

<210> SEQ ID NO 66
<211> LENGTH: 53
<212> TYPE: DNA
<213> ORGANISM: Artificial sequence
<220> FEATURE:

<223> OTHER INFORMATION: Synthetic

<400> SEQUENCE: 66
agttgcaggt gcagatgaag ctggtgccgg tccagttatt ggtccgctgg tta          53

<210> SEQ ID NO 67
<211> LENGTH: 53
<212> TYPE: DNA
<213> ORGANISM: Artificial sequence
<220> FEATURE:
<223> OTHER INFORMATION: Synthetic

<400> SEQUENCE: 67
taaccagcgg accataact ggaccggcac cagcttcatc tgcacctgca act            53

<210> SEQ ID NO 68
<211> LENGTH: 53
<212> TYPE: DNA
<213> ORGANISM: Artificial sequence
<220> FEATURE:
<223> OTHER INFORMATION: Synthetic

<400> SEQUENCE: 68
cggtgatttt ggttccggtt acccgcagga tccgcgtact aagaaatggc tgg          53

<210> SEQ ID NO 69
<211> LENGTH: 53
<212> TYPE: DNA
<213> ORGANISM: Artificial sequence
<220> FEATURE:
<223> OTHER INFORMATION: Synthetic

<400> SEQUENCE: 69
ccagccattt cttagtacgc ggatcctgcg ggtaaccgga accaaaatca ccg          53

<210> SEQ ID NO 70
<211> LENGTH: 224
<212> TYPE: PRT
<213> ORGANISM: Artificial sequence
<220> FEATURE:
<223> OTHER INFORMATION: Synthetic

<400> SEQUENCE: 70

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Arg
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 71
<211> LENGTH: 224
<212> TYPE: PRT
<213> ORGANISM: Artificial sequence
<220> FEATURE:
<223> OTHER INFORMATION: Synthetic

<400> SEQUENCE: 71

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Thr Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 72
<211> LENGTH: 224
<212> TYPE: PRT
<213> ORGANISM: Artificial sequence
<220> FEATURE:
<223> OTHER INFORMATION: Synthetic

<400> SEQUENCE: 72

Met Lys Val Ala Gly Ala Asp Glu Ala Gly Arg Gly Pro Val Ile Gly
1               5                   10                  15

Pro Leu Val Ile Val Ala Ala Val Glu Glu Asp Lys Ile Arg Ser
              20                  25                  30

Leu Thr Lys Leu Gly Val Lys Asp Ser Lys Gln Leu Thr Pro Ala Gln
         35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
             100                 105                 110

Arg Phe Ala Glu Asn Ile Arg Ser Arg Leu Ala Tyr Glu Ala Lys Val
         115                 120                 125

Val Ala Glu His Lys Ala Asp Ala Lys Tyr Glu Ile Val Ser Ala Ala
130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                 165                 170                 175

Lys Lys Trp Leu Glu Glu Trp Tyr Ser Lys His Gly Asn Phe Pro Pro
             180                 185                 190

Ile Val Arg Arg Thr Trp Tyr Thr Ala Lys Lys Ile Glu Glu Lys Phe
         195                 200                 205

Lys Arg Ala Gln Leu Thr Leu Asp Asn Phe Leu Lys Arg Phe Arg Asn
210                 215                 220

<210> SEQ ID NO 73
<211> LENGTH: 224
<212> TYPE: PRT
<213> ORGANISM: Artificial sequence
<220> FEATURE:
<223> OTHER INFORMATION: Synthetic

<400> SEQUENCE: 73

Met Lys Val Ala Gly Ala Asp Glu Ala Gly Arg Gly Pro Val Ile Gly
1               5                   10                  15

Pro Leu Val Ile Val Ala Ala Val Glu Glu Asp Lys Ile Arg Ser
              20                  25                  30

Leu Thr Lys Leu Gly Val Lys Asp Ser Lys Gln Leu Thr Pro Ala Gln
         35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
             100                 105                 110

Arg Phe Ala Glu Asn Ile Arg Ser Arg Leu Ala Tyr Glu Ala Lys Val
         115                 120                 125

Val Ala Glu His Lys Ala Asp Ala Lys Tyr Glu Ile Val Ser Ala Ala
130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asn Thr Ala Lys Lys Ile Glu Glu Lys Phe
            195                 200                 205

Lys Arg Ala Gln Leu Thr Leu Asp Asn Phe Leu Lys Arg Phe Arg Asn
        210                 215                 220

<210> SEQ ID NO 74
<211> LENGTH: 224
<212> TYPE: PRT
<213> ORGANISM: Artificial sequence
<220> FEATURE:
<223> OTHER INFORMATION: Synthetic

<400> SEQUENCE: 74

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Gly Thr Ala Lys Lys Ile Glu Glu Lys Phe
            195                 200                 205

Lys Arg Ala Gln Leu Thr Leu Asp Asn Phe Leu Lys Arg Phe Arg Asn
        210                 215                 220

<210> SEQ ID NO 75
<211> LENGTH: 224
<212> TYPE: PRT
<213> ORGANISM: Artificial sequence
<220> FEATURE:
<223> OTHER INFORMATION: Synthetic

<400> SEQUENCE: 75

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser 20                  25                  30
Leu Thr Lys Leu Gly Val Lys Asp Ser Lys Gln Leu Thr Pro Ala Gln
                35                  40                  45
Arg Glu Lys Leu Phe Asp Glu Ile Val Lys Val Leu Asp Asp Tyr Ser
         50                  55                  60
Val Val Ile Val Ser Pro Gln Asp Ile Asp Gly Arg Lys Gly Ser Met
 65                  70                  75                  80
Asn Glu Leu Glu Val Glu Asn Phe Val Lys Ala Leu Asn Ser Leu Lys
                 85                  90                  95
Val Lys Pro Glu Val Ile Tyr Ile Asp Ser Ala Asp Val Lys Ala Glu
                100                 105                 110
Arg Phe Ala Glu Asn Ile Arg Ser Arg Leu Ala Tyr Glu Ala Lys Val
                115                 120                 125
Val Ala Glu His Lys Ala Asp Ala Lys Tyr Glu Ile Val Ser Ala Ala
                130                 135                 140
Ser Ile Leu Ala Lys Val Ile Arg Asp Arg Glu Ile Glu Lys Leu Lys
145                 150                 155                 160
Ala Glu Tyr Gly Asp Phe Gly Ser Gly Tyr Pro Ser Asp Pro Arg Thr
                165                 170                 175
Lys Lys Trp Leu Glu Glu Trp Tyr Ser Lys His Gly Asn Phe Pro Pro
                180                 185                 190
Ile Val Arg Arg Thr Trp Glu Thr Ala Lys Lys Ile Glu Glu Lys Phe
                195                 200                 205
Lys Arg Ala Gln Leu Thr Leu Asp Asn Phe Leu Lys Arg Phe Arg Asn
                210                 215                 220

<210> SEQ ID NO 76
<211> LENGTH: 224
<212> TYPE: PRT
<213> ORGANISM: Artificial sequence
<220> FEATURE:
<223> OTHER INFORMATION: Synthetic

<400> SEQUENCE: 76

Met Lys Val Ala Gly Ala Asp Glu Ala Gly Arg Gly Pro Val Ile Gly
 1               5                  10                  15
Pro Leu Val Ile Val Ala Ala Val Val Glu Glu Asp Lys Ile Arg Ser
                20                  25                  30
Leu Thr Lys Leu Gly Val Lys Asp Ser Lys Gln Leu Thr Pro Ala Gln
                35                  40                  45
Arg Glu Lys Leu Phe Asp Glu Ile Val Lys Val Leu Asp Asp Tyr Ser
         50                  55                  60
Val Val Ile Val Ser Pro Gln Asp Ile Asp Gly Arg Lys Gly Ser Met
 65                  70                  75                  80
Asn Glu Leu Glu Val Glu Asn Phe Val Lys Ala Leu Asn Ser Leu Lys
                 85                  90                  95
Val Lys Pro Glu Val Ile Tyr Ile Asp Ser Ala Asp Val Lys Ala Glu
                100                 105                 110
Arg Phe Ala Glu Asn Ile Arg Ser Arg Leu Ala Tyr Glu Ala Lys Val
                115                 120                 125
Val Ala Glu His Lys Ala Asp Ala Lys Tyr Glu Ile Val Ser Ala Ala
                130                 135                 140
Ser Ile Leu Ala Lys Val Ile Arg Asp Arg Glu Ile Glu Lys Leu Lys
145                 150                 155                 160
Ala Glu Tyr Gly Asp Phe Gly Ser Gly Tyr Pro Ser Asp Pro Arg Thr

```
                165                 170                 175
Lys Lys Trp Leu Glu Glu Trp Tyr Ser Lys His Gly Asn Phe Pro Pro
            180                 185                 190

Ile Val Arg Arg Thr Trp Val Thr Ala Lys Lys Ile Glu Glu Lys Phe
            195                 200                 205

Lys Arg Ala Gln Leu Thr Leu Asp Asn Phe Leu Lys Arg Phe Arg Asn
            210                 215                 220

<210> SEQ ID NO 77
<211> LENGTH: 224
<212> TYPE: PRT
<213> ORGANISM: Artificial sequence
<220> FEATURE:
<223> OTHER INFORMATION: Synthetic

<400> SEQUENCE: 77

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Leu
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
            210                 215                 220

<210> SEQ ID NO 78
<211> LENGTH: 224
<212> TYPE: PRT
<213> ORGANISM: Artificial sequence
<220> FEATURE:
<223> OTHER INFORMATION: Synthetic

<400> SEQUENCE: 78

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30
```

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Leu Leu Lys Arg Phe Arg Asn
        210                 215                 220

<210> SEQ ID NO 79
<211> LENGTH: 224
<212> TYPE: PRT
<213> ORGANISM: Artificial sequence
<220> FEATURE:
<223> OTHER INFORMATION: Synthetic

<400> SEQUENCE: 79

Met Lys Val Ala Gly Ala Asp Glu Ala Gly Arg Gly Ser Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

```
Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
210                 215                 220

<210> SEQ ID NO 80
<211> LENGTH: 224
<212> TYPE: PRT
<213> ORGANISM: Artificial sequence
<220> FEATURE:
<223> OTHER INFORMATION: Synthetic

<400> SEQUENCE: 80

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
210                 215                 220

<210> SEQ ID NO 81
<211> LENGTH: 224
<212> TYPE: PRT
<213> ORGANISM: Artificial sequence
<220> FEATURE:
<223> OTHER INFORMATION: Synthetic

<400> SEQUENCE: 81

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Arg
        35                  40                  45
```

```
Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asn Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220
```

<210> SEQ ID NO 82
<211> LENGTH: 224
<212> TYPE: PRT
<213> ORGANISM: Artificial sequence
<220> FEATURE:
<223> OTHER INFORMATION: Synthetic

<400> SEQUENCE: 82

```
Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Arg
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190
```

Ile Val Arg Arg Thr Trp Asp Thr Ala Lys Lys Ile Glu Glu Lys Phe
                195                 200                 205

Lys Arg Ala Gln Leu Thr Leu Asp Asn Phe Leu Lys Arg Phe Arg Asn
    210                 215                 220

<210> SEQ ID NO 83
<211> LENGTH: 224
<212> TYPE: PRT
<213> ORGANISM: Artificial sequence
<220> FEATURE:
<223> OTHER INFORMATION: Synthetic

<400> SEQUENCE: 83

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
                100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Thr Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
                195                 200                 205

Lys Arg Ala Gln Leu Thr Leu Asp Asn Phe Leu Lys Arg Phe Arg Asn
    210                 215                 220

<210> SEQ ID NO 84
<211> LENGTH: 224
<212> TYPE: PRT
<213> ORGANISM: Artificial sequence
<220> FEATURE:
<223> OTHER INFORMATION: Synthetic

<400> SEQUENCE: 84

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser

```
            50                  55                  60
Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Tyr Thr Ala Lys Lys Ile Glu Glu Lys Phe
            195                 200                 205

Lys Arg Ala Gln Leu Thr Leu Asp Asn Phe Leu Lys Arg Phe Arg Asn
            210                 215                 220

<210> SEQ ID NO 85
<211> LENGTH: 224
<212> TYPE: PRT
<213> ORGANISM: Artificial sequence
<220> FEATURE:
<223> OTHER INFORMATION: Synthetic

<400> SEQUENCE: 85

Met Lys Val Ala Gly Ala Asp Glu Ala Gly Arg Gly Pro Val Ile Gly
  1               5                  10                  15

Pro Leu Val Ile Val Ala Ala Val Val Glu Glu Asp Lys Ile Arg Ser
                 20                  25                  30

Leu Thr Lys Leu Gly Val Lys Asp Ser Lys Gln Leu Thr Pro Ala Gln
             35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asn Thr Ala Lys Lys Ile Glu Glu Lys Phe
```

```
                 195                 200                 205
Lys Arg Ala Gln Leu Thr Leu Asp Asn Phe Leu Lys Arg Phe Arg Asn
    210                 215                 220

<210> SEQ ID NO 86
<211> LENGTH: 224
<212> TYPE: PRT
<213> ORGANISM: Artificial sequence
<220> FEATURE:
<223> OTHER INFORMATION: Synthetic

<400> SEQUENCE: 86

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Gly Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 87
<211> LENGTH: 224
<212> TYPE: PRT
<213> ORGANISM: Artificial sequence
<220> FEATURE:
<223> OTHER INFORMATION: Synthetic

<400> SEQUENCE: 87

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60
```

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Glu Thr Ala Lys Lys Ile Glu Glu Lys Phe
            195                 200                 205

Lys Arg Ala Gln Leu Thr Leu Asp Asn Phe Leu Lys Arg Phe Arg Asn
210                 215                 220

<210> SEQ ID NO 88
<211> LENGTH: 224
<212> TYPE: PRT
<213> ORGANISM: Artificial sequence
<220> FEATURE:
<223> OTHER INFORMATION: Synthetic

<400> SEQUENCE: 88

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
50                  55                  60

Val Val Ile Val Ser Pro Gln Asp Ile Asp Gly Arg Lys Gly Ser Leu
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Leu
            195                 200                 205

```
Lys Arg Ala Gln Leu Thr Leu Asp Asn Leu Leu Lys Arg Phe Arg Asn
    210                 215                 220
```

<210> SEQ ID NO 89
<211> LENGTH: 224
<212> TYPE: PRT
<213> ORGANISM: Artificial sequence
<220> FEATURE:
<223> OTHER INFORMATION: Synthetic

<400> SEQUENCE: 89

```
Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Leu
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Leu
        195                 200                 205

Lys Arg Ala Gln Leu Thr Leu Asp Asn Leu Leu Lys Arg Phe Arg Asn
    210                 215                 220
```

<210> SEQ ID NO 90
<211> LENGTH: 224
<212> TYPE: PRT
<213> ORGANISM: Artificial sequence
<220> FEATURE:
<223> OTHER INFORMATION: Synthetic

<400> SEQUENCE: 90

```
Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80
```

```
Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 91
<211> LENGTH: 224
<212> TYPE: PRT
<213> ORGANISM: Artificial sequence
<220> FEATURE:
<223> OTHER INFORMATION: Synthetic

<400> SEQUENCE: 91

Met Lys Val Ala Gly Ala Asp Glu Ala Gly Arg Ser Pro Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220
```

<210> SEQ ID NO 92
<211> LENGTH: 224
<212> TYPE: PRT
<213> ORGANISM: Artificial sequence
<220> FEATURE:
<223> OTHER INFORMATION: Synthetic

<400> SEQUENCE: 92

Met Lys Val Ala Gly Ala Asp Glu Ala Ser Arg Gly Pro Val Ile Gly
1               5                   10                  15

Pro Leu Val Ile Val Ala Ala Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

<210> SEQ ID NO 93
<211> LENGTH: 224
<212> TYPE: PRT
<213> ORGANISM: Artificial sequence
<220> FEATURE:
<223> OTHER INFORMATION: Synthetic

<400> SEQUENCE: 93

Met Lys Val Ala Gly Ala Asp Glu Ala Gly Arg Gly Pro Val Ile Gly
1               5                   10                  15

Pro Leu Val Ile Val Ala Ala Val Glu Glu Asp Lys Ile Arg Ser
            20                  25                  30

Leu Thr Lys Leu Gly Val Lys Asp Ser Lys Gln Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys

```
                    85                  90                  95
Val Lys Pro Glu Val Ile Tyr Ile Asp Ser Ala Asp Val Lys Ala Glu
                100                 105                 110

Arg Phe Ala Glu Asn Ile Arg Ser Arg Leu Ala Tyr Glu Ala Lys Val
                115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Lys Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
                180                 185                 190

Ile Val Arg Arg Thr Trp Asp Thr Ala Lys Lys Ile Glu Glu Lys Phe
                195                 200                 205

Lys Arg Ala Gln Leu Thr Leu Asp Asn Phe Leu Lys Arg Phe Arg Asn
            210                 215                 220
```

<210> SEQ ID NO 94
<211> LENGTH: 224
<212> TYPE: PRT
<213> ORGANISM: Artificial sequence
<220> FEATURE:
<223> OTHER INFORMATION: Synthetic

<400> SEQUENCE: 94

```
Met Lys Val Ala Gly Ala Asp Glu Ala Ser Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Val Asp Val Lys Ala Glu
                100                 105                 110

Arg Phe Ala Glu Asn Ile Arg Ser Arg Leu Ala Tyr Glu Ala Lys Val
                115                 120                 125

Val Ala Glu His Lys Ala Asp Ala Lys Tyr Glu Ile Val Ser Ala Ala
            130                 135                 140

Ser Ile Leu Ala Lys Val Ile Arg Asp Arg Glu Ile Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
                180                 185                 190

Ile Val Arg Arg Thr Trp Asp Thr Ala Lys Lys Ile Glu Glu Lys Phe
                195                 200                 205

Lys Arg Ala Gln Leu Thr Leu Asp Asn Phe Leu Lys Arg Phe Arg Asn
            210                 215                 220
```

<210> SEQ ID NO 95
<211> LENGTH: 224
<212> TYPE: PRT
<213> ORGANISM: Pyrococcus furiosis

<400> SEQUENCE: 95

```
Met Lys Ile Gly Gly Ile Asp Glu Ala Gly Arg Gly Pro Ala Ile Gly
1               5                   10                  15

Pro Leu Val Val Ala Thr Val Val Asp Glu Lys Asn Ile Glu Lys
            20                  25                  30

Leu Arg Asn Ile Gly Val Lys Asp Ser Lys Gln Leu Thr Pro His Glu
        35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
    130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220
```

<210> SEQ ID NO 96
<211> LENGTH: 220
<212> TYPE: PRT
<213> ORGANISM: Pyrococcus horikoshii

<400> SEQUENCE: 96

```
Met Lys Val Ala Gly Val Asp Glu Ala Gly Arg Gly Pro Val Ile Gly
1               5                   10                  15

Pro Leu Val Ile Gly Val Ala Val Ile Asp Glu Lys Asn Ile Glu Arg
            20                  25                  30

Leu Arg Asp Ile Gly Val Lys Asp Ser Lys Gln Leu Thr Pro Gly Gln
        35                  40                  45

Arg Glu Lys Leu Phe Ser Lys Leu Ile Asp Ile Leu Asp Asp Tyr Tyr
    50                  55                  60

Val Leu Leu Val Thr Pro Lys Glu Ile Asp Glu Arg His His Ser Met
65                  70                  75                  80

Asn Glu Leu Glu Ala Glu Lys Phe Val Val Ala Leu Asn Ser Leu Arg
                85                  90                  95

Ile Lys Pro Gln Lys Ile Tyr Val Asp Ser Ala Asp Val Asp Pro Lys
            100                 105                 110

Arg Phe Ala Ser Leu Ile Lys Ala Gly Leu Lys Tyr Glu Ala Thr Val
```

```
            115                 120                 125
Ile Ala Glu His Lys Ala Asp Ala Lys Tyr Glu Ile Val Ser Ala Ala
            130                 135                 140
Ser Ile Ile Ala Lys Val Thr Arg Asp Arg Glu Ile Glu Lys Leu Lys
145                 150                 155                 160
Gln Lys Tyr Gly Glu Phe Gly Ser Gly Tyr Pro Ser Asp Pro Arg Thr
                        165                 170                 175
Lys Glu Trp Leu Glu Glu Tyr Tyr Lys Gln Tyr Gly Asp Phe Pro Pro
                180                 185                 190
Ile Val Arg Arg Thr Trp Glu Thr Ala Arg Lys Ile Glu Glu Arg Phe
                195                 200                 205
Arg Lys Asn Gln Leu Thr Leu Asp Lys Phe Leu Lys
                210                 215                 220
```

<210> SEQ ID NO 97
<211> LENGTH: 228
<212> TYPE: PRT
<213> ORGANISM: Thermococcus kodakarensis

<400> SEQUENCE: 97

```
Met Lys Ile Ala Gly Ile Asp Glu Ala Gly Arg Gly Pro Val Ile Gly
1               5                   10                  15
Pro Met Val Ile Ala Ala Val Val Asp Glu Asn Ser Leu Pro Lys
                20                  25                  30
Leu Glu Glu Leu Lys Val Arg Asp Ser Lys Lys Leu Thr Pro Lys Arg
            35                  40                  45
Arg Glu Lys Leu Phe Asn Glu Ile Leu Gly Val Leu Asp Asp Tyr Val
50                  55                  60
Ile Leu Glu Leu Pro Pro Asp Val Ile Gly Ser Arg Glu Gly Thr Leu
65                  70                  75                  80
Asn Glu Phe Glu Val Glu Asn Phe Ala Lys Ala Leu Asn Ser Leu Lys
                85                  90                  95
Val Lys Pro Asp Val Ile Tyr Ala Asp Ala Ala Asp Val Asp Glu Glu
            100                 105                 110
Arg Phe Ala Arg Glu Leu Gly Glu Arg Leu Asn Phe Glu Ala Glu Val
        115                 120                 125
Val Ala Lys His Lys Ala Asp Asp Ile Phe Pro Val Val Ser Ala Ala
            130                 135                 140
Ser Ile Leu Ala Lys Val Thr Arg Asp Arg Ala Val Glu Lys Leu Lys
145                 150                 155                 160
Glu Glu Tyr Gly Glu Ile Gly Ser Gly Tyr Pro Ser Asp Pro Arg Thr
                165                 170                 175
Arg Ala Phe Leu Glu Asn Tyr Tyr Arg Glu His Gly Glu Phe Pro Pro
                180                 185                 190
Ile Val Arg Lys Gly Trp Lys Thr Leu Lys Lys Ile Ala Glu Lys Val
                195                 200                 205
Glu Ser Glu Lys Lys Ala Glu Glu Arg Gln Ala Thr Leu Asp Arg Tyr
            210                 215                 220
Phe Arg Lys Val
225
```

<210> SEQ ID NO 98
<211> LENGTH: 224
<212> TYPE: PRT
<213> ORGANISM: Thermococcus litoralis -continued

<400> SEQUENCE: 98

Met Lys Leu Gly Gly Ile Asp Glu Ala Gly Arg Gly Pro Val Ile Gly
1               5                   10                  15

Pro Leu Val Ile Ala Ala Val Val Asp Glu Ser Arg Met Gln Glu
            20                  25                  30

Leu Glu Ala Leu Gly Val Lys Asn Ser Lys Lys Leu Thr Pro Lys Arg
        35                  40                  45

Arg Glu Glu Leu Phe Glu Glu Ile Val Gln Ile Val Asp Asp His Val
    50                  55                  60

Ile Ile Gln Leu Ser Pro Glu Glu Ile Asp Gly Arg Asp Gly Thr Met
65                  70                  75                  80

Asn Glu Leu Glu Ile Glu Asn Phe Ala Lys Ala Leu Asn Ser Leu Lys
                85                  90                  95

Val Lys Pro Asp Val Leu Tyr Ile Asp Ala Ala Asp Val Lys Glu Lys
            100                 105                 110

Arg Phe Gly Asp Ile Ile Gly Glu Arg Leu Ser Phe Ser Pro Lys Ile
        115                 120                 125

Ile Ala Glu His Lys Ala Asp Ser Lys Tyr Ile Pro Val Ala Ala Ala
    130                 135                 140

Ser Ile Leu Ala Lys Val Thr Arg Asp Arg Ala Ile Glu Lys Leu Lys
145                 150                 155                 160

Glu Leu Tyr Gly Glu Ile Gly Ser Gly Tyr Pro Ser Asp Pro Asn Thr
                165                 170                 175

Arg Arg Phe Leu Glu Glu Tyr Tyr Lys Ala His Gly Glu Phe Pro Pro
            180                 185                 190

Ile Val Arg Lys Ser Trp Lys Thr Leu Arg Lys Ile Glu Glu Lys Leu
        195                 200                 205

Lys Ala Lys Lys Thr Gln Pro Thr Ile Leu Asp Phe Leu Lys Lys Pro
    210                 215                 220

<210> SEQ ID NO 99
<211> LENGTH: 54
<212> TYPE: DNA
<213> ORGANISM: Artificial sequence
<220> FEATURE:
<223> OTHER INFORMATION: Synthetic

<400> SEQUENCE: 99
gactccaaac agctgacccc ggcgcgccgt gaaaaactgt tcgatgaaat cgta            54

<210> SEQ ID NO 100
<211> LENGTH: 51
<212> TYPE: DNA
<213> ORGANISM: Artificial sequence
<220> FEATURE:
<223> OTHER INFORMATION: Synthetic

<400> SEQUENCE: 100
aacaataacc agcggaccaa taaccgaacc acgaccagct tcatctgcac c               51

<210> SEQ ID NO 101
<211> LENGTH: 51
<212> TYPE: DNA
<213> ORGANISM: Artificial sequence
<220> FEATURE:
<223> OTHER INFORMATION: Synthetic

<400> SEQUENCE: 101
gtatccgcag cctctatcct ggcaaccgtt atccgtgacc gcgagatcga a               51

<210> SEQ ID NO 102
<211> LENGTH: 51
<212> TYPE: DNA
<213> ORGANISM: Artificial sequence
<220> FEATURE:
<223> OTHER INFORMATION: Synthetic

<400> SEQUENCE: 102
ttcgatctcg cggtcacgga taacggttgc caggatagag gctgcggata c        51

<210> SEQ ID NO 103
<211> LENGTH: 51
<212> TYPE: DNA
<213> ORGANISM: Artificial sequence
<220> FEATURE:
<223> OTHER INFORMATION: Synthetic

<400> SEQUENCE: 103
ccgccgatcg tgcgtcgtac ttggtatact gcaaagaaaa tcgaagaaaa a        51

<210> SEQ ID NO 104
<211> LENGTH: 51
<212> TYPE: DNA
<213> ORGANISM: Artificial sequence
<220> FEATURE:
<223> OTHER INFORMATION: Synthetic

<400> SEQUENCE: 104
tttttcttcg attttctttg cagtatacca agtacgacgc acgatcggcg g        51

<210> SEQ ID NO 105
<211> LENGTH: 51
<212> TYPE: DNA
<213> ORGANISM: Artificial sequence
<220> FEATURE:
<223> OTHER INFORMATION: Synthetic

<400> SEQUENCE: 105
ccgccgatcg tgcgtcgtac ttggaatact gcaaagaaaa tcgaagaaaa a        51

<210> SEQ ID NO 106
<211> LENGTH: 51
<212> TYPE: DNA
<213> ORGANISM: Artificial sequence
<220> FEATURE:
<223> OTHER INFORMATION: Synthetic

<400> SEQUENCE: 106
tttttcttcg attttctttg cagtattcca agtacgacgc acgatcggcg g        51

<210> SEQ ID NO 107
<211> LENGTH: 51
<212> TYPE: DNA
<213> ORGANISM: Artificial sequence
<220> FEATURE:
<223> OTHER INFORMATION: Synthetic

<400> SEQUENCE: 107
ccgccgatcg tgcgtcgtac ttggggtact gcaaagaaaa tcgaagaaaa a        51

<210> SEQ ID NO 108
<211> LENGTH: 51
<212> TYPE: DNA
<213> ORGANISM: Artificial sequence
<220> FEATURE:

-continued

<223> OTHER INFORMATION: Synthetic

<400> SEQUENCE: 108 ttttcttcg attttctttg cagtacccca agtacgacgc acgatcggcg g        51

<210> SEQ ID NO 109
<211> LENGTH: 51
<212> TYPE: DNA
<213> ORGANISM: Artificial sequence
<220> FEATURE:
<223> OTHER INFORMATION: Synthetic

<400> SEQUENCE: 109
ccgccgatcg tgcgtcgtac ttgggagact gcaaagaaaa tcgaagaaaa a        51

<210> SEQ ID NO 110
<211> LENGTH: 51
<212> TYPE: DNA
<213> ORGANISM: Artificial sequence
<220> FEATURE:
<223> OTHER INFORMATION: Synthetic

<400> SEQUENCE: 110 ttttcttcg attttctttg cagtctccca agtacgacgc acgatcggcg g        51

<210> SEQ ID NO 111
<211> LENGTH: 51
<212> TYPE: DNA
<213> ORGANISM: Artificial sequence
<220> FEATURE:
<223> OTHER INFORMATION: Synthetic

<400> SEQUENCE: 111
ccgccgatcg tgcgtcgtac ttgggttact gcaaagaaaa tcgaagaaaa a        51

<210> SEQ ID NO 112
<211> LENGTH: 51
<212> TYPE: DNA
<213> ORGANISM: Artificial sequence
<220> FEATURE:
<223> OTHER INFORMATION: Synthetic

<400> SEQUENCE: 112 ttttcttcg attttctttg cagtaaccca agtacgacgc acgatcggcg g        51

<210> SEQ ID NO 113
<211> LENGTH: 51
<212> TYPE: DNA
<213> ORGANISM: Artificial sequence
<220> FEATURE:
<223> OTHER INFORMATION: Synthetic

<400> SEQUENCE: 113
gacattgacg gtcgtaaggg cagcctgaac gaactggagg tagaaaactt c        51

<210> SEQ ID NO 114
<211> LENGTH: 51
<212> TYPE: DNA
<213> ORGANISM: Artificial sequence
<220> FEATURE:
<223> OTHER INFORMATION: Synthetic

<400> SEQUENCE: 114
gaagttttct acctccagtt cgttcaggct gcccttacga ccgtcaatgt c        51

<210> SEQ ID NO 115
<211> LENGTH: 51
<212> TYPE: DNA
<213> ORGANISM: Artificial sequence
<220> FEATURE:
<223> OTHER INFORMATION: Synthetic

<400> SEQUENCE: 115
cgtgcgcagc tgaccctgga caacttactg aagcgttttc gcaacaagct t        51

<210> SEQ ID NO 116
<211> LENGTH: 51
<212> TYPE: DNA
<213> ORGANISM: Artificial sequence
<220> FEATURE:
<223> OTHER INFORMATION: Synthetic

<400> SEQUENCE: 116
aagcttgttg cgaaaacgct tcagtaagtt gtccagggtc agctgcgcac g        51

<210> SEQ ID NO 117
<211> LENGTH: 53
<212> TYPE: DNA
<213> ORGANISM: Artificial sequence
<220> FEATURE:
<223> OTHER INFORMATION: Synthetic

<400> SEQUENCE: 117
gccggaagtt atttacattg attccgttga tgttaaagct gaacgtttcg ctg      53

<210> SEQ ID NO 118
<211> LENGTH: 53
<212> TYPE: DNA
<213> ORGANISM: Artificial sequence
<220> FEATURE:
<223> OTHER INFORMATION: Synthetic

<400> SEQUENCE: 118
cagcgaaacg ttcagcttta acatcaacgg aatcaatgta ataacttcc ggc       53

<210> SEQ ID NO 119
<211> LENGTH: 54
<212> TYPE: DNA
<213> ORGANISM: Artificial sequence
<220> FEATURE:
<223> OTHER INFORMATION: Synthetic

<400> SEQUENCE: 119
tgcaggtgca gatgaagctg gtcgttctcc agttattggt ccgctggtta ttgt     54

<210> SEQ ID NO 120
<211> LENGTH: 54
<212> TYPE: DNA
<213> ORGANISM: Artificial sequence
<220> FEATURE:
<223> OTHER INFORMATION: Synthetic

<400> SEQUENCE: 120
acaataacca gcggaccaat aactggagaa cgaccagctt catctgcacc tgca     54

<210> SEQ ID NO 121
<211> LENGTH: 53
<212> TYPE: DNA
<213> ORGANISM: Artificial sequence
<220> FEATURE:
<223> OTHER INFORMATION: Synthetic

<400> SEQUENCE: 121
gaaagttgca ggtgcagatg aagcttctcg tggtccagtt attggtccgc tgg            53

<210> SEQ ID NO 122
<211> LENGTH: 53
<212> TYPE: DNA
<213> ORGANISM: Artificial sequence
<220> FEATURE:
<223> OTHER INFORMATION: Synthetic

<400> SEQUENCE: 122
ccagcggacc aataactgga ccacgagaag cttcatctgc acctgcaact ttc            53

<210> SEQ ID NO 123
<211> LENGTH: 49
<212> TYPE: DNA
<213> ORGANISM: Artificial sequence
<220> FEATURE:
<223> OTHER INFORMATION: Synthetic

<400> SEQUENCE: 123
aaaagttatc cgtgaccgcg agatcaagaa gctgaaagcc gaatacggt                 49

<210> SEQ ID NO 124
<211> LENGTH: 52
<212> TYPE: DNA
<213> ORGANISM: Artificial sequence
<220> FEATURE:
<223> OTHER INFORMATION: Synthetic

<400> SEQUENCE: 124
atcaccgtat tcggctttca gcttcttgat ctcgcggtca cggataactt tt             52

<210> SEQ ID NO 125
<211> LENGTH: 224
<212> TYPE: PRT
<213> ORGANISM: Artificial sequence
<220> FEATURE:
<223> OTHER INFORMATION: Synthetic

<400> SEQUENCE: 125

```
Met Lys Val Ala Gly Ala Asp Glu Ala Gly Arg Gly Pro Val Ile Gly
 1               5                  10                  15

Pro Leu Val Ile Val Ala Ala Val Val Glu Glu Asp Lys Ile Arg Ser
             20                  25                  30

Leu Thr Lys Leu Gly Val Lys Asp Ser Lys Gln Leu Thr Pro Ala Gln
         35                  40                  45

Arg Glu Lys Leu Phe Asp Glu Ile Val Lys Val Leu Asp Asp Tyr Ser
     50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Glu Val Ile Tyr Ile Asp Ser Ala Asp Val Lys Ala Glu
            100                 105                 110

Arg Phe Ala Glu Asn Ile Arg Ser Arg Leu Ala Tyr Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160
```

```
Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Asn Phe Leu Lys Arg Phe Arg Asn
            210                 215                 220

<210> SEQ ID NO 126
<211> LENGTH: 224
<212> TYPE: PRT
<213> ORGANISM: Artificial sequence
<220> FEATURE:
<223> OTHER INFORMATION: Synthetic

<400> SEQUENCE: 126

Met Lys Ile Gly Gly Ile Asp Glu Ala Gly Arg Gly Ser Ala Ile Gly
1               5                   10                  15

Pro Leu Val Val Ala Thr Val Val Asp Glu Lys Asn Ile Glu Lys
            20                  25                  30

Leu Arg Asn Ile Gly Val Lys Asp Ser Lys Gln Leu Thr Pro His Glu
            35                  40                  45

Arg Lys Asn Leu Phe Ser Gln Ile Thr Ser Ile Ala Asp Asp Tyr Lys
            50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
            115                 120                 125

Ile Ala Glu His Lys Ala Asp Ala Lys Tyr Pro Val Val Ser Ala Ala
            130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
            165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
            195                 200                 205

Lys Ala Lys Lys Ser Gln Leu Thr Leu Asp Lys Phe Phe Lys Lys Pro
            210                 215                 220

<210> SEQ ID NO 127
<211> LENGTH: 224
<212> TYPE: PRT
<213> ORGANISM: Artificial sequence
<220> FEATURE:
<223> OTHER INFORMATION: Synthetic

<400> SEQUENCE: 127

Met Lys Ile Gly Gly Ile Asp Glu Ala Gly Arg Gly Pro Ala Ile Gly
1               5                   10                  15

Pro Leu Val Val Ala Thr Val Val Asp Glu Lys Asn Ile Glu Lys
```

```
            20                  25                  30
Leu Arg Asn Ile Gly Val Lys Asp Ser Lys Gln Leu Thr Pro His Arg
            35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
        130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220
```

<210> SEQ ID NO 128
<211> LENGTH: 224
<212> TYPE: PRT
<213> ORGANISM: Artificial sequence
<220> FEATURE:
<223> OTHER INFORMATION: Synthetic

<400> SEQUENCE: 128

```
Met Lys Ile Gly Gly Ile Asp Glu Ala Gly Arg Gly Pro Ala Ile Gly
1               5                   10                  15

Pro Leu Val Val Ala Thr Val Val Asp Glu Lys Asn Ile Glu Lys
            20                  25                  30

Leu Arg Asn Ile Gly Val Lys Asp Ser Lys Gln Leu Thr Pro His Glu
            35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Leu
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
        130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
```

```
                165                 170                 175
Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220

<210> SEQ ID NO 129
<211> LENGTH: 224
<212> TYPE: PRT
<213> ORGANISM: Artificial sequence
<220> FEATURE:
<223> OTHER INFORMATION: Synthetic

<400> SEQUENCE: 129

Met Lys Ile Gly Gly Ile Asp Glu Ala Gly Arg Gly Pro Ala Ile Gly
1               5                  10                  15

Pro Leu Val Val Ala Thr Val Val Asp Glu Lys Asn Ile Glu Lys
            20                  25                  30

Leu Arg Asn Ile Gly Val Lys Asp Ser Lys Gln Leu Thr Pro His Glu
        35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Val Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
    130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220

<210> SEQ ID NO 130
<211> LENGTH: 224
<212> TYPE: PRT
<213> ORGANISM: Artificial sequence
<220> FEATURE:
<223> OTHER INFORMATION: Synthetic

<400> SEQUENCE: 130

Met Lys Ile Gly Gly Ile Asp Glu Ala Gly Arg Gly Ser Ala Ile Gly
1               5                  10                  15

Pro Leu Val Val Ala Thr Val Val Asp Glu Lys Asn Ile Glu Lys
            20                  25                  30
```

```
Leu Arg Asn Ile Gly Val Lys Asp Ser Lys Gln Leu Thr Pro His Glu
         35                  40                  45

Arg Lys Asn Leu Phe Ser Gln Ile Thr Ser Ile Ala Asp Asp Tyr Lys
 50                  55                  60

Ile Val Ile Val Ser Pro Glu Ile Asp Asn Arg Ser Gly Thr Met
 65                  70                  75                  80

Asn Glu Leu Glu Val Glu Lys Phe Ala Leu Ala Leu Asn Ser Leu Gln
                 85                  90                  95

Ile Lys Pro Ala Leu Ile Tyr Ala Asp Ala Val Asp Val Asp Ala Asn
            100                 105                 110

Arg Phe Ala Ser Leu Ile Glu Arg Arg Leu Asn Tyr Lys Ala Lys Ile
            115                 120                 125

Ile Ala Glu His Lys Ala Asp Ala Lys Tyr Pro Val Val Ser Ala Ala
        130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Pro
    210                 215                 220

<210> SEQ ID NO 131
<211> LENGTH: 220
<212> TYPE: PRT
<213> ORGANISM: Artificial sequence
<220> FEATURE:
<223> OTHER INFORMATION: Synthetic

<400> SEQUENCE: 131

Met Lys Val Ala Gly Val Asp Glu Ala Gly Arg Gly Pro Val Ile Gly
 1               5                  10                  15

Pro Leu Val Ile Gly Val Ala Val Ile Asp Glu Lys Asn Ile Glu Arg
                20                  25                  30

Leu Arg Asp Ile Gly Val Lys Asp Ser Lys Gln Leu Thr Pro Gly Arg
         35                  40                  45

Arg Glu Lys Leu Phe Ser Lys Leu Ile Asp Ile Leu Asp Asp Tyr Tyr
 50                  55                  60

Val Leu Leu Val Thr Pro Lys Glu Ile Asp Glu Arg His His Ser Met
 65                  70                  75                  80

Asn Glu Leu Glu Ala Glu Lys Phe Val Val Ala Leu Asn Ser Leu Arg
                 85                  90                  95

Ile Lys Pro Gln Lys Ile Tyr Val Asp Ser Ala Asp Val Asp Pro Lys
            100                 105                 110

Arg Phe Ala Ser Leu Ile Lys Ala Gly Leu Lys Tyr Glu Ala Thr Val
            115                 120                 125

Ile Ala Glu His Lys Ala Asp Ala Lys Tyr Glu Ile Val Ser Ala Ala
        130                 135                 140

Ser Ile Ile Ala Lys Val Thr Arg Asp Arg Glu Ile Glu Lys Leu Lys
145                 150                 155                 160

Gln Lys Tyr Gly Glu Phe Gly Ser Gly Tyr Pro Ser Asp Pro Arg Thr
                165                 170                 175
```

```
Lys Glu Trp Leu Glu Glu Tyr Tyr Lys Gln Tyr Gly Asp Phe Pro Pro
            180                 185                 190

Ile Val Arg Arg Thr Trp Glu Thr Ala Arg Lys Ile Glu Glu Arg Phe
        195                 200                 205

Arg Lys Asn Gln Leu Thr Leu Asp Lys Phe Leu Lys
    210                 215                 220

<210> SEQ ID NO 132
<211> LENGTH: 220
<212> TYPE: PRT
<213> ORGANISM: Artificial Sequence
<220> FEATURE:
<223> OTHER INFORMATION: Synthetic

<400> SEQUENCE: 132

Met Lys Val Ala Gly Val Asp Glu Ala Gly Arg Gly Pro Val Ile Gly
1               5                   10                  15

Pro Leu Val Ile Gly Val Ala Val Ile Asp Glu Lys Asn Ile Glu Arg
            20                  25                  30

Leu Arg Asp Ile Gly Val Lys Asp Ser Lys Gln Leu Thr Pro Gly Gln
        35                  40                  45

Arg Glu Lys Leu Phe Ser Lys Leu Ile Asp Ile Leu Asp Asp Tyr Tyr
50                  55                  60

Val Leu Leu Val Thr Pro Lys Glu Ile Asp Glu Arg His His Ser Leu
65                  70                  75                  80

Asn Glu Leu Glu Ala Glu Lys Phe Val Val Ala Leu Asn Ser Leu Arg
                85                  90                  95

Ile Lys Pro Gln Lys Ile Tyr Val Asp Ser Ala Asp Val Asp Pro Lys
            100                 105                 110

Arg Phe Ala Ser Leu Ile Lys Ala Gly Leu Lys Tyr Glu Ala Thr Val
        115                 120                 125

Ile Ala Glu His Lys Ala Asp Ala Lys Tyr Glu Ile Val Ser Ala Ala
    130                 135                 140

Ser Ile Ile Ala Lys Val Thr Arg Asp Arg Glu Ile Glu Lys Leu Lys
145                 150                 155                 160

Gln Lys Tyr Gly Glu Phe Gly Ser Gly Tyr Pro Ser Asp Pro Arg Thr
                165                 170                 175

Lys Glu Trp Leu Glu Glu Tyr Tyr Lys Gln Tyr Gly Asp Phe Pro Pro
            180                 185                 190

Ile Val Arg Arg Thr Trp Glu Thr Ala Arg Lys Ile Glu Glu Arg Phe
        195                 200                 205

Arg Lys Asn Gln Leu Thr Leu Asp Lys Phe Leu Lys
    210                 215                 220

<210> SEQ ID NO 133
<211> LENGTH: 220
<212> TYPE: PRT
<213> ORGANISM: Artificial Sequence
<220> FEATURE:
<223> OTHER INFORMATION: Synthetic

<400> SEQUENCE: 133

Met Lys Val Ala Gly Val Asp Glu Ala Gly Arg Gly Pro Val Ile Gly
1               5                   10                  15

Pro Leu Val Ile Gly Val Ala Val Ile Asp Glu Lys Asn Ile Glu Arg
            20                  25                  30

Leu Arg Asp Ile Gly Val Lys Asp Ser Lys Gln Leu Thr Pro Gly Gln
        35                  40                  45
```

```
Arg Glu Lys Leu Phe Ser Lys Leu Ile Asp Ile Leu Asp Asp Tyr Tyr
         50                  55                  60

Val Leu Leu Val Thr Pro Lys Glu Ile Asp Glu Arg His His Ser Met
 65                  70                  75                  80

Asn Glu Leu Glu Ala Glu Lys Phe Val Val Ala Leu Asn Ser Leu Arg
                 85                  90                  95

Ile Lys Pro Gln Lys Ile Tyr Val Asp Ser Val Asp Val Asp Pro Lys
                100                 105                 110

Arg Phe Ala Ser Leu Ile Lys Ala Gly Leu Lys Tyr Glu Ala Thr Val
                115                 120                 125

Ile Ala Glu His Lys Ala Asp Ala Lys Tyr Glu Ile Val Ser Ala Ala
        130                 135                 140

Ser Ile Ile Ala Lys Val Thr Arg Asp Arg Glu Ile Glu Lys Leu Lys
145                 150                 155                 160

Gln Lys Tyr Gly Glu Phe Gly Ser Gly Tyr Pro Ser Asp Pro Arg Thr
                165                 170                 175

Lys Glu Trp Leu Glu Glu Tyr Tyr Lys Gln Tyr Gly Asp Phe Pro Pro
                180                 185                 190

Ile Val Arg Arg Thr Trp Glu Thr Ala Arg Lys Ile Glu Glu Arg Phe
                195                 200                 205

Arg Lys Asn Gln Leu Thr Leu Asp Lys Phe Leu Lys
        210                 215                 220

<210> SEQ ID NO 134
<211> LENGTH: 228
<212> TYPE: PRT
<213> ORGANISM: Artificial Sequence
<220> FEATURE:
<223> OTHER INFORMATION: Synthetic

<400> SEQUENCE: 134

Met Lys Ile Ala Gly Ile Asp Glu Ala Gly Arg Gly Ser Val Ile Gly
 1               5                  10                  15

Pro Met Val Ile Ala Ala Val Val Val Asp Glu Asn Ser Leu Pro Lys
                20                  25                  30

Leu Glu Glu Leu Lys Val Arg Asp Ser Lys Lys Leu Thr Pro Lys Arg
            35                  40                  45

Arg Glu Lys Leu Phe Asn Glu Ile Leu Gly Val Leu Asp Asp Tyr Val
         50                  55                  60

Ile Leu Glu Leu Pro Pro Asp Val Ile Gly Ser Arg Glu Gly Thr Leu
 65                  70                  75                  80

Asn Glu Phe Glu Val Glu Asn Phe Ala Lys Ala Leu Asn Ser Leu Lys
                 85                  90                  95

Val Lys Pro Asp Val Ile Tyr Ala Asp Ala Ala Asp Val Asp Glu Glu
                100                 105                 110

Arg Phe Ala Arg Glu Leu Gly Glu Arg Leu Asn Phe Glu Ala Glu Val
                115                 120                 125

Val Ala Lys His Lys Ala Asp Asp Ile Phe Pro Val Val Ser Ala Ala
        130                 135                 140

Ser Ile Leu Ala Lys Val Thr Arg Asp Arg Ala Val Glu Lys Leu Lys
145                 150                 155                 160

Glu Glu Tyr Gly Glu Ile Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
                180                 185                 190
```

```
Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
    210                 215                 220

Phe Arg Lys Val
225

<210> SEQ ID NO 135
<211> LENGTH: 228
<212> TYPE: PRT
<213> ORGANISM: Artificial Sequence
<220> FEATURE:
<223> OTHER INFORMATION: Synthetic

<400> SEQUENCE: 135

Met Lys Ile Ala Gly Ile Asp Glu Ala Gly Arg Gly Pro Val Ile Gly
1               5                   10                  15

Pro Met Val Ile Ala Ala Val Val Val Asp Glu Asn Ser Leu Pro Lys
                20                  25                  30

Leu Glu Glu Leu Lys Val Arg Asp Ser Lys Lys Leu Thr Pro Lys Arg
            35                  40                  45

Arg Glu Lys Leu Phe Asn Glu Ile Leu Gly Val Leu Asp Asp Tyr Val
        50                  55                  60

Ile Leu Glu Leu Pro Pro Asp Val Ile Gly Ser Arg Glu Gly Thr Leu
65                  70                  75                  80

Asn Glu Phe Glu Val Glu Asn Phe Ala Lys Ala Leu Asn Ser Leu Lys
                85                  90                  95

Val Lys Pro Asp Val Ile Tyr Ala Asp Ala Val Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
    130                 135                 140

Ser Ile Leu Ala Lys Val Thr Arg Asp Arg Ala Val Glu Lys Leu Lys
145                 150                 155                 160

Glu Glu Tyr Gly Glu Ile Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
    210                 215                 220

Phe Arg Lys Val
225

<210> SEQ ID NO 136
<211> LENGTH: 228
<212> TYPE: PRT
<213> ORGANISM: Artificial Sequence
<220> FEATURE:
<223> OTHER INFORMATION: Synthetic

<400> SEQUENCE: 136

Met Lys Ile Ala Gly Ile Asp Glu Ala Gly Arg Gly Ser Val Ile Gly
1               5                   10                  15

Pro Met Val Ile Ala Ala Val Val Val Asp Glu Asn Ser Leu Pro Lys
```

-continued

```
                 20                  25                  30
Leu Glu Glu Leu Lys Val Arg Asp Ser Lys Leu Thr Pro Lys Arg
             35                  40                  45
Arg Glu Lys Leu Phe Asn Glu Ile Leu Gly Val Leu Asp Asp Tyr Val
 50                  55                  60
Ile Leu Glu Leu Pro Asp Val Ile Gly Ser Arg Glu Gly Thr Leu
 65                  70                  75                  80
Asn Glu Phe Glu Val Glu Asn Phe Ala Lys Ala Leu Asn Ser Leu Lys
                 85                  90                  95
Val Lys Pro Asp Val Ile Tyr Ala Asp Ala Val Asp Val Asp Glu Glu
             100                 105                 110
Arg Phe Ala Arg Glu Leu Gly Glu Arg Leu Asn Phe Glu Ala Glu Val
             115                 120                 125
Val Ala Lys His Lys Ala Asp Asp Ile Phe Pro Val Val Ser Ala Ala
             130                 135                 140
Ser Ile Leu Ala Lys Val Thr Arg Asp Arg Ala Val Glu Lys Leu Lys
145                 150                 155                 160
Glu Glu Tyr Gly Glu Ile Gly Ser Gly Tyr Pro Ser Asp Pro Arg Thr
                 165                 170                 175
Arg Ala Phe Leu Glu Asn Tyr Tyr Arg Glu His Gly Glu Phe Pro Pro
             180                 185                 190
Ile Val Arg Lys Gly Trp Lys Thr Leu Lys Lys Ile Ala Glu Lys Val
             195                 200                 205
Glu Ser Glu Lys Lys Ala Glu Glu Arg Gln Ala Thr Leu Asp Arg Tyr
             210                 215                 220
Phe Arg Lys Val
225

<210> SEQ ID NO 137
<211> LENGTH: 224
<212> TYPE: PRT
<213> ORGANISM: Artificial Sequence
<220> FEATURE:
<223> OTHER INFORMATION: Synthetic

<400> SEQUENCE: 137

Met Lys Leu Gly Gly Ile Asp Glu Ala Gly Arg Gly Pro Val Ile Gly
 1               5                  10                  15
Pro Leu Val Ile Ala Ala Val Val Val Asp Glu Ser Arg Met Gln Glu
                 20                  25                  30
Leu Glu Ala Leu Gly Val Lys Asn Ser Lys Lys Leu Thr Pro Lys Arg
             35                  40                  45
Arg Glu Glu Leu Phe Glu Ile Val Gln Ile Val Asp Asp His Val
 50                  55                  60
Ile Ile Gln Leu Ser Pro Glu Glu Ile Asp Gly Arg Asp Gly Thr Leu
 65                  70                  75                  80
Asn Glu Leu Glu Ile Glu Asn Phe Ala Lys Ala Leu Asn Ser Leu Lys
                 85                  90                  95
Val Lys Pro Asp Val Leu Tyr Ile Asp Ala Ala Asp Val Lys Glu Lys
             100                 105                 110
Arg Phe Gly Asp Ile Ile Gly Glu Arg Leu Ser Phe Ser Pro Lys Ile
             115                 120                 125
Ile Ala Glu His Lys Ala Asp Ser Lys Tyr Ile Pro Val Ala Ala Ala
             130                 135                 140
Ser Ile Leu Ala Lys Val Thr Arg Asp Arg Ala Ile Glu Lys Leu Lys
```

```
                145                 150                 155                 160
Glu Leu Tyr Gly Glu Ile Gly Ser Gly Tyr Pro Ser Asp Pro Asn Thr
                    165                 170                 175
Arg Arg Phe Leu Glu Glu Tyr Tyr Lys Ala His Gly Glu Phe Pro Pro
                    180                 185                 190
Ile Val Arg Lys Ser Trp Lys Thr Leu Arg Lys Ile Glu Glu Lys Leu
                    195                 200                 205
Lys Ala Lys Lys Thr Gln Pro Thr Ile Leu Asp Phe Leu Lys Lys Pro
                    210                 215                 220

<210> SEQ ID NO 138
<211> LENGTH: 224
<212> TYPE: PRT
<213> ORGANISM: Artificial Sequence
<220> FEATURE:
<223> OTHER INFORMATION: Synthetic

<400> SEQUENCE: 138

Met Lys Leu Gly Gly Ile Asp Glu Ala Gly Arg Gly Pro Val Ile Gly
1               5                   10                  15
Pro Leu Val Ile Ala Ala Val Val Asp Glu Ser Arg Met Gln Glu
                    20                  25                  30
Leu Glu Ala Leu Gly Val Lys Asn Ser Lys Lys Leu Thr Pro Lys Arg
                    35                  40                  45
Arg Glu Glu Leu Phe Glu Glu Ile Val Gln Ile Val Asp Asp His Val
                    50                  55                  60
Ile Ile Gln Leu Ser Pro Glu Glu Ile Asp Gly Arg Asp Gly Thr Met
65                  70                  75                  80
Asn Glu Leu Glu Ile Glu Asn Phe Ala Lys Ala Leu Asn Ser Leu Lys
                    85                  90                  95
Val Lys Pro Asp Val Leu Tyr Ile Asp Ala Val Asp Val Lys Glu Lys
                    100                 105                 110
Arg Phe Gly Asp Ile Ile Gly Glu Arg Leu Ser Phe Ser Pro Lys Ile
                    115                 120                 125
Ile Ala Glu His Lys Ala Asp Ser Lys Tyr Ile Pro Val Ala Ala Ala
                    130                 135                 140
Ser Ile Leu Ala Lys Val Thr Arg Asp Arg Ala Ile Glu Lys Leu Lys
145                 150                 155                 160
Glu Leu Tyr Gly Glu Ile Gly Ser Gly Tyr Pro Ser Asp Pro Asn Thr
                    165                 170                 175
Arg Arg Phe Leu Glu Glu Tyr Tyr Lys Ala His Gly Glu Phe Pro Pro
                    180                 185                 190
Ile Val Arg Lys Ser Trp Lys Thr Leu Arg Lys Ile Glu Glu Lys Leu
                    195                 200                 205
Lys Ala Lys Lys Thr Gln Pro Thr Ile Leu Asp Phe Leu Lys Lys Pro
                    210                 215                 220

<210> SEQ ID NO 139
<211> LENGTH: 53
<212> TYPE: DNA
<213> ORGANISM: Artificial Sequence
<220> FEATURE:
<223> OTHER INFORMATION: Synthetic

<400> SEQUENCE: 139
tggcatcgac gaagccggcc gtggtagcgc gatcggtccg ctggtagtag cta          53
```

<210> SEQ ID NO 140
<211> LENGTH: 53
<212> TYPE: DNA
<213> ORGANISM: Artificial Sequence
<220> FEATURE:
<223> OTHER INFORMATION: Synthetic

<400> SEQUENCE: 140
tagctactac cagcggaccg atcgcgctac cacggccggc ttcgtcgatg cca    53

<210> SEQ ID NO 141
<211> LENGTH: 53
<212> TYPE: DNA
<213> ORGANISM: Artificial Sequence
<220> FEATURE:
<223> OTHER INFORMATION: Synthetic

<400> SEQUENCE: 141
agactccaaa cagctgacgc cgcaccgtcg taaaaacctg ttttcccaga tca    53

<210> SEQ ID NO 142
<211> LENGTH: 53
<212> TYPE: DNA
<213> ORGANISM: Artificial Sequence
<220> FEATURE:
<223> OTHER INFORMATION: Synthetic

<400> SEQUENCE: 142
tgatctggga aaacaggttt ttacgacggt gcggcgtcag ctgtttggag tct    53

<210> SEQ ID NO 143
<211> LENGTH: 53
<212> TYPE: DNA
<213> ORGANISM: Artificial Sequence
<220> FEATURE:
<223> OTHER INFORMATION: Synthetic

<400> SEQUENCE: 143
agaaattgac aaccgtagcg gtaccctgaa cgagctggaa gttgaaaaat tcg    53

<210> SEQ ID NO 144
<211> LENGTH: 53
<212> TYPE: DNA
<213> ORGANISM: Artificial Sequence
<220> FEATURE:
<223> OTHER INFORMATION: Synthetic

<400> SEQUENCE: 144 cgaattttc aacttccagc tcgttcaggg taccgctacg gttgtcaatt tct    53

<210> SEQ ID NO 145
<211> LENGTH: 53
<212> TYPE: DNA
<213> ORGANISM: Artificial Sequence
<220> FEATURE:
<223> OTHER INFORMATION: Synthetic

<400> SEQUENCE: 145
gccggctctg atctacgcag acgcagtgga tgttgatgca aaccgcttcg cat    53

<210> SEQ ID NO 146
<211> LENGTH: 53
<212> TYPE: DNA
<213> ORGANISM: Artificial Sequence
<220> FEATURE:
<223> OTHER INFORMATION: Synthetic

<400> SEQUENCE: 146
atgcgaagcg gtttgcatca acatccactg cgtctgcgta gatcagagcc ggc            53

<210> SEQ ID NO 147
<211> LENGTH: 53
<212> TYPE: DNA
<213> ORGANISM: Artificial Sequence
<220> FEATURE:
<223> OTHER INFORMATION: Synthetic

<400> SEQUENCE: 147
aggggtcgat gaagccgggc gcggatcagt catcggcccc ttagtgattg gcg            53

<210> SEQ ID NO 148
<211> LENGTH: 53
<212> TYPE: DNA
<213> ORGANISM: Artificial Sequence
<220> FEATURE:
<223> OTHER INFORMATION: Synthetic

<400> SEQUENCE: 148
cgccaatcac taaggggccg atgactgatc cgcgcccggc ttcatcgacc cct            53

<210> SEQ ID NO 149
<211> LENGTH: 53
<212> TYPE: DNA
<213> ORGANISM: Artificial Sequence
<220> FEATURE:
<223> OTHER INFORMATION: Synthetic

<400> SEQUENCE: 149
ggattccaag cagttaactc cgggccgtcg cgagaagttg ttcagtaaat tga            53

<210> SEQ ID NO 150
<211> LENGTH: 53
<212> TYPE: DNA
<213> ORGANISM: Artificial Sequence
<220> FEATURE:
<223> OTHER INFORMATION: Synthetic

<400> SEQUENCE: 150
tcaatttact gaacaacttc tcgcgacggc ccggagttaa ctgcttggaa tcc            53

<210> SEQ ID NO 151
<211> LENGTH: 53
<212> TYPE: DNA
<213> ORGANISM: Artificial Sequence
<220> FEATURE:
<223> OTHER INFORMATION: Synthetic

<400> SEQUENCE: 151
ggaaatcgac gaacgccacc atagcctgaa tgaattagaa gcagagaagt tcg            53

<210> SEQ ID NO 152
<211> LENGTH: 53
<212> TYPE: DNA
<213> ORGANISM: Artificial Sequence
<220> FEATURE:
<223> OTHER INFORMATION: Synthetic

<400> SEQUENCE: 152
cgaacttctc tgcttctaat tcattcaggc tatggtggcg ttcgtcgatt tcc            53

<210> SEQ ID NO 153
<211> LENGTH: 53

```
<212> TYPE: DNA
<213> ORGANISM: Artificial Sequence
<220> FEATURE:
<223> OTHER INFORMATION: Synthetic

<400> SEQUENCE: 153
gccccagaag atttatgttg actcagttga cgttgacccc aagcgttttg cct       53

<210> SEQ ID NO 154
<211> LENGTH: 53
<212> TYPE: DNA
<213> ORGANISM: Artificial Sequence
<220> FEATURE:
<223> OTHER INFORMATION: Synthetic

<400> SEQUENCE: 154
aggcaaaacg cttggggtca acgtcaactg agtcaacata aatcttctgg ggc       53

<210> SEQ ID NO 155
<211> LENGTH: 53
<212> TYPE: DNA
<213> ORGANISM: Artificial Sequence
<220> FEATURE:
<223> OTHER INFORMATION: Synthetic

<400> SEQUENCE: 155
tggcatcgat gaagccggcc gtggcagcgt aattggtcca atggttatcg ctg       53

<210> SEQ ID NO 156
<211> LENGTH: 53
<212> TYPE: DNA
<213> ORGANISM: Artificial Sequence
<220> FEATURE:
<223> OTHER INFORMATION: Synthetic

<400> SEQUENCE: 156
cagcgataac cattggacca attacgctgc cacggccggc ttcatcgatg cca       53

<210> SEQ ID NO 157
<211> LENGTH: 53
<212> TYPE: DNA
<213> ORGANISM: Artificial Sequence
<220> FEATURE:
<223> OTHER INFORMATION: Synthetic

<400> SEQUENCE: 157
accggacgta atctatgctg atgcggttga cgttgacgag gaacgttttg ccc       53

<210> SEQ ID NO 158
<211> LENGTH: 53
<212> TYPE: DNA
<213> ORGANISM: Artificial Sequence
<220> FEATURE:
<223> OTHER INFORMATION: Synthetic

<400> SEQUENCE: 158
gggcaaaacg ttcctcgtca acgtcaaccg catcagcata gattacgtcc ggt       53

<210> SEQ ID NO 159
<211> LENGTH: 53
<212> TYPE: DNA
<213> ORGANISM: Artificial Sequence
<220> FEATURE:
<223> OTHER INFORMATION: Synthetic

<400> SEQUENCE: 159
```

<210> SEQ ID NO 160
<211> LENGTH: 53
<212> TYPE: DNA
<213> ORGANISM: Artificial Sequence
<220> FEATURE:
<223> OTHER INFORMATION: Synthetic

<400> SEQUENCE: 160
ctgcaatcac cagcggtccg atgactgacc cgcgtccggc tcatcgata cct    53

<210> SEQ ID NO 161
<211> LENGTH: 53
<212> TYPE: DNA
<213> ORGANISM: Artificial Sequence
<220> FEATURE:
<223> OTHER INFORMATION: Synthetic

<400> SEQUENCE: 161
ggaaatcgac gggcgcgatg gcaccctgaa tgagttagaa attgaaaatt tcg    53

<210> SEQ ID NO 162
<211> LENGTH: 53
<212> TYPE: DNA
<213> ORGANISM: Artificial Sequence
<220> FEATURE:
<223> OTHER INFORMATION: Synthetic

<400> SEQUENCE: 162
cgaaattttc aatttctaac tcattcaggg tgccatcgcg cccgtcgatt tcc    53

<210> SEQ ID NO 163
<211> LENGTH: 53
<212> TYPE: DNA
<213> ORGANISM: Artificial Sequence
<220> FEATURE:
<223> OTHER INFORMATION: Synthetic

<400> SEQUENCE: 163
acccgatgtt ttatacatcg acgccgttga cgttaaggag aagcgttttg ggg    53

<210> SEQ ID NO 164
<211> LENGTH: 53
<212> TYPE: DNA
<213> ORGANISM: Artificial Sequence
<220> FEATURE:
<223> OTHER INFORMATION: Synthetic

<400> SEQUENCE: 164
ccccaaaacg cttctcctta acgtcaacgg cgtcgatgta taaacatcg ggt    53

<210> SEQ ID NO 165
<211> LENGTH: 224
<212> TYPE: PRT
<213> ORGANISM: Artificial Sequence
<220> FEATURE:
<223> OTHER INFORMATION: Synthetic

<400> SEQUENCE: 165

Met Lys Val Ala Gly Ala Asp Glu Ala Gly Arg Gly Ser Val Ile Gly
1               5                   10                  15

Pro Leu Val Ile Val Ala Ala Val Val Glu Glu Asp Lys Ile Arg Ser
            20                  25                  30

Leu Thr Lys Leu Gly Val Lys Asp Ser Lys Gln Leu Thr Pro Ala Arg

-continued

```
             35                  40                  45
Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Leu
65              70                  75                  80

Asn Glu Leu Glu Val Glu Asn Phe Val Lys Ala Leu Asn Ser Leu Lys
            85                  90                  95

Val Lys Pro Glu Val Ile Tyr Ile Asp Ser Val Asp Val Lys Ala Glu
            100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220
```